United States Patent [19]
Tang et al.

[11] Patent Number: 5,824,306
[45] Date of Patent: Oct. 20, 1998

[54] DIROFILARIA AND BRUGIA ANKYRIN PROTEINS, NUCLEIC ACID MOLECULES, AND USES THEREOF

[75] Inventors: Liang Tang; E. Scot Blehm, both of Fort Collins, Colo.

[73] Assignee: Heska Corporation, Fort Collins, Colo.

[21] Appl. No.: 31,485

[22] Filed: Feb. 26, 1998

Related U.S. Application Data

[62] Division of Ser. No. 847,429, Apr. 24, 1997.

[51] Int. Cl.$^6$ ............................. A61K 35/14; C07K 14/00
[52] U.S. Cl. ....................... 424/130.1; 514/2; 530/387.1; 530/350
[58] Field of Search .............................. 424/130.1; 514/2; 530/387.1, 350

Primary Examiner—Karen Cochrane Carlson
Attorney, Agent, or Firm—Heska Corporation

[57] ABSTRACT

The present invention relates to Dirofilaria ankyrin proteins and to Brugia ankyrin proteins; to Dirofilaria ankyrin nucleic acid molecules and to Brugia ankyrin nucleic acid molecules, including those that encode such ankyrin proteins; to antibodies raised against such ankyrin proteins; and to compounds that inhibit Dirofilaria or Brugia ankyrin function. The present invention also includes methods to identify and obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from diseases caused by parasitic helminths.

14 Claims, No Drawings

DIROFILARIA AND BRUGIA ANKYRIN PROTEINS, NUCLEIC ACID MOLECULES, AND USES THEREOF

This application is a divisional application of U.S. application Ser. No. 08/847,429, filed Apr. 24, 1997.

FIELD OF THE INVENTION

The present invention relates to Dirofilaria and Brugia ankyrin nucleic acid molecules, proteins encoded by such nucleic acid molecules, antibodies raised against such proteins, compounds capable of inhibiting the function of such proteins and methods to identify such inhibitors. The present invention also includes therapeutic compositions comprising such nucleic acid molecules, proteins, antibodies, and/or inhibitors, as well as their use to protect animals from diseases caused by parasitic helminths, such as heartworm disease, elephantiasis, and hydrocele.

BACKGROUND OF THE INVENTION

Parasitic helminth infections in animals, including humans, are typically treated by chemical drugs. One disadvantage with chemical drugs is that they must be administered often. For example, dogs susceptible to heartworm are typically treated monthly. Repeated administration of drugs, however, often leads to the development of resistant helminth strains that no longer respond to treatment. Furthermore, many of the chemical drugs cause harmful side effects in the animals being treated, and as larger doses become required due to the build up of resistance, the side effects become even greater. Moreover, a number of drugs only treat symptoms of a parasitic disease but are unable to prevent infection by the parasitic helminth.

An alternative method to prevent parasitic helminth infection includes administering a vaccine against a parasitic helminth. Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic helminths. Although a number of prominent antigens have been identified in several parasitic helminths, including in Dirofilaria and Brugia species, there is yet to be a commercially available vaccine developed for any parasitic helminth.

As an example of the complexity of parasitic helminths, the life cycle of *D. immitis*, the helminth that causes heartworm, includes a variety of life forms, each of which presents different targets, and challenges, for immunization. In a mosquito, *D. immitis* microfilariae go through two larval stages (L1 and L2) and become mature third stage larvae (L3), which can then be transmitted back to the dog when the mosquito takes a blood meal. In a dog, the L3 molt to the fourth larval stage (L4), and subsequently to the fifth stage, or immature adults. The immature adults migrate to the heart and pulmonary arteries, where they mature to adult heartworms. Adult heartworms are quite large and preferentially inhabit the heart and pulmonary arteries of an animal. Sexually mature adults, after mating, produce microfilariae which traverse capillary beds and circulate in the vascular system of the dog. In particular, heartworm is a major problem in dogs, which typically do not develop immunity upon infection (i.e., dogs can become reinfected even after being cured by chemotherapy). In addition, heartworm infection has been reported in cats, ferrets, and humans.

As such, there remains a need to identify efficacious compositions that protect animals against diseases caused by parasitic helminths such as *D. immitis* and *B. malayi*. Such compositions would preferably also protect animals from infection by such helminths.

The mechanisms and regulatory pathways involved in *D. immitis* migration and development are not clear. From infective L3 to mature adult, the nematode has to migrate and develop, with two molts, within its definitive host. It has been shown in the free living nematode, *Caenorhabditis elegans* (*C. elegans*), that the development of the larvae is regulated by environmental signals through chemosensory neurons. Blockage of signal transmission affects the development of the nematode (Bargmann, et al., 1991, *Science*, 251, 1243–1246). Many neuron-related genes have been identified in *C. elegans*. Mutations of the genes which control normal neuron function in *C. elegans* will not only affect the behavior of the nematode, but will also affect the development of the larvae and egg laying of mutated female worms. In parasitic nematodes, very little is known about mechanisms involved in the signal transmission and the developmental regulation of the parasites. However, host and tissue specificities in parasite infections suggest that parasitic nematodes might also need correct environmental signals for development.

Ankyrins are peripheral membrane proteins which have been found in erythrocyte, kidney and neuronal cells of mammals. Genes coding for three different mammalian ankyrins (ankyrin$_R$, ankyrin$_B$ and ankyrin$_G$) have been cloned. Ankyrin$_R$ was originally identified as part of the erythrocyte membrane skeleton, and was recently also localized to the plasma membrane of a subpopulation of post mitotic neurons in rat brain (Lambert, et al., 1993, *J. Neurosci.*, 13, 3725–3735). Ankyrin$_B$ is a developmentally regulated human brain protein which has two alternatively spliced isoforms with molecular masses of 220 kilodaltons (kD) and 440 kD (Kunimoto, et al., 1991, *J. Cell Biology*, 115, 1319–1331). Ankyrin$_G$ is a more recently isolated human gene that encodes two neural-specific ankyrin variants (480 kD and 270 kD), which have been localized to the axonal initial segment and node of Ranvier (Kordeli, et al., 1995, *J. Biol. Chem.*, 270, 2352–2359). Studies on mammalian ankyrins indicate that ankyrins bind a variety of proteins which have functions involved with the anion exchanger (Drenckhahn, et al., 1988, *Science*, 230, 1287–1289), Na+/K±ATPase, amiloride-sensitive sodium channel in kidney (Smith, et al., 1991, *Proc. Natl. Acad. Sci. U.S.A.*, 88, 6971–6975), voltage dependent sodium channel of the brain and the neuromuscular junction (Srinivasan, et al., 1988, *Nature*, 333, 177–180), and nervous system cell adhesion molecules (Davis, et al., 1994, *J. Biol. Chem.*, 269, 27163–27166).

Analyses of mammalian ankyrins have revealed that these large proteins are divided into three functional domains. These include an N-terminal membrane-binding domain of about 89–95 kD, a spectrin binding domain of about 62 kD, and a C-terminal regulatory domain of about 50–55 kD. The membrane-binding domain is primarily comprised of tandem repeats of about 33 amino acids each. This domain usually has about 22–24 copies of these repeats. The repeat units appear to function in binding to membrane proteins such as anion exchangers, sodium channels, and certain adhesion molecules. The spectrin-binding domain, as the name implies, functions in binding to the spectrin-based cytoskeleton of cells positioned inside the plasma membrane. Finally, the regulatory domain, which is the most variant domain among the different ankyrins that have been studied, appears to function in as a repressor and/or an activator of the protein-binding activities of the other two domains. Some of the variability seen in this domain among different ankyrin species appears to be the result of alternative splicing of nascent transcripts. For a review of ankyrin structure and function, see, for example, Bennett, 1992, *J. Biol. Chem.,* 267, 8703–8706. Bennett, ibid., is incorporated herein by reference in its entirety.

An ankyrin gene (UNC-44) has also been identified in the free living nematode, *C. elegans.* Mutation of UNC-44 affects the development and function of the nervous system (Otsuka et al., 1995, *J. Cell Biology,* 129, 1081–1092). More recently, a cDNA encoding a 90-kilodalton (kD) neuronal protein, E1, which is reported to be an ankyrin-related protein, has been cloned from the filariid nematode, *Onchocerca volvulus* (*O. volvulus*), a human parasite. The cDNA was identified by using immuno-screening with antisera collected from putatively immune individuals from an endemic area of onchocerciasis. Localization studies by immunohistochemical assay indicated that the *O. volvulus* E1 native protein was localized to the nerve ring, the neuronal cell bodies, and the basal labyrinth within the extracellular clefts of the hypodermis in the adult nematode (Erttmann et al., 1996a, *J. Biol. Chem.,* 271, 1645–1650). This 462-amino acid *O. volvulus* protein is reported to be full length.

SUMMARY OF THE INVENTION

The present invention relates to a novel product and a process to protect animals against parasitic helminth infection (e.g., prevent and/or treat such an infection). According to the present invention there are provided Dirofilaria and Brugia ankyrin proteins and mimetopes thereof; Dirofilaria and Brugia ankyrin nucleic acid molecules, including those that encode such proteins; antibodies raised against such ankyrin proteins (i.e., anti-Dirofilaria and anti-Brugia ankyrin antibodies); and compounds that inhibit the function of parasitic helminth ankyrins (i.e, inhibitory compounds).

The present invention also includes methods to obtain and/or identify such proteins, nucleic acid molecules, antibodies and inhibitory compounds. Also included in the present invention are therapeutic compositions comprising such proteins, nucleic acid molecules, antibodies, and/or inhibitory compounds, as well as use of such therapeutic compositions to protect animals from diseases caused by parasitic helminths.

One embodiment of the present invention is an isolated nucleic acid molecule that includes either a Dirofilaria ankyrin nucleic acid molecule, preferably a *Dirofilaria immitis* (*D. immitis*) ankyrin nucleic acid molecule, or a Brugia ankyrin nucleic acid molecule, preferably a *Brugia malayi* (*B. malayi*) ankyrin nucleic acid molecule. Such nucleic acid molecules are referred to as ankyrin nucleic acid molecules. A *D. immitis* ankyrin nucleic acid molecule preferably includes nucleic acid sequence SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:1, SEQ ID NO:13, SEQ ID NO:14, SEQ ID NO:16, SEQ ID NO:17, SEQ ID NO:18, SEQ ID NO:19, SEQ ID NO:21, SEQ ID NO:22, SEQ ID NO:24, SEQ ID NO:25, SEQ ID NO:26, SEQ ID NO:27, SEQ ID NO:29, SEQ ID NO:30, SEQ ID NO:31, SEQ ID NO:32, SEQ ID NO:34, SEQ ID NO:35, and/or SEQ ID NO:36, and a *B. malayi* ankyrin nucleic acid molecule preferably includes nucleic acid sequence SEQ ID NO:37, SEQ ID NO:38, SEQ ID NO:40, and/or SEQ ID NO:41.

In one embodiment, a preferred *D. immitis* or *B. malayi* ankyrin nucleic acid molecule comprises a coding region of at least about 1500 nucleotides, preferably at least about 3000 nucleotides, even more preferably at least about 4500 nucleotides, which is capable of encoding an ankyrin protein of at least about 500 amino acids in length, preferably at least about 1000 amino acids in length, even more preferably at least about 1500 amino acids in length. In another embodiment, a preferred *D. immitis* or *B. malayi* ankyrin nucleic acid molecule comprises a full-length coding region which encodes a full-length ankyrin protein.

The present invention also relates to recombinant molecules, recombinant viruses and recombinant cells that include an isolated ankyrin nucleic acid molecule of the present invention. Also included are methods to produce such nucleic acid molecules, recombinant molecules, recombinant viruses and recombinant cells.

Another embodiment of the present invention includes either a Dirofilaria or a Brugia ankyrin protein, or a protein that includes a Dirofilaria or a Brugia ankyrin protein. Preferred ankyrin proteins include *D. immitis* ankyrin proteins or *B. malayi* ankyrin proteins. A preferred *D. immitis* ankyrin protein comprises amino acid sequence SEQ ID NO:2, SEQ ID NO:7, SEQ ID NO:12, SEQ ID NO:15, SEQ ID NO:20, SEQ ID NO:23, SEQ ID NO:28, and/or SEQ ID NO:33, and a preferred *B. malayi* ankyrin protein comprises amino acid sequence SEQ ID NO:38.

In one embodiment, a preferred *D. immitis* or *B. malayi* ankyrin protein comprises an amino acid sequence of at least about 500 amino acids in length, preferably at least about 1000 amino acids in length, even more preferably at least about 1500 amino acids in length. In another embodiment, a preferred *D. immitis* or *B. malayi* ankyrin protein comprises a full-length protein, i.e., a protein encoded by a full-length coding region.

The present invention also relates to: mimetopes of either Dirofilaria or Brugia ankyrin proteins, preferably to mimetopes of either *D. immitis* and *B. malayi* ankyrin proteins; isolated antibodies that selectively bind to either Dirofilaria or Brugia ankyrin proteins or mimetopes thereof; and inhibitors of Dirofilaria or Brugia ankyrin protein function. Also included are methods, including recombinant methods, to produce proteins, mimetopes, antibodies, and inhibitors of the present invention.

Yet another embodiment of the present invention is a therapeutic composition that is capable of protecting an animal from disease caused by a parasitic helminth. Such a therapeutic composition includes one or more of the following protective compounds: a Dirofilaria or a Brugia ankyrin protein or a mimetope thereof; an isolated Dirofilaria or Brugia ankyrin nucleic acid molecule; an isolated antibody that selectively binds to a Dirofilaria or a Brugia ankyrin protein; and/or a compound capable of inhibiting ankyrin function identified by its ability to inhibit either Dirofilaria or a Brugia ankyrin function. A preferred therapeutic composition of the present invention also includes an excipient, an adjuvant and/or a carrier. Preferred ankyrin nucleic acid molecule therapeutic compositions of the present invention include genetic vaccines, recombinant virus vaccines and recombinant cell vaccines. Also included in the present invention is a method to protect an animal from disease caused by a parasitic helminth, comprising the step of administering to the animal a therapeutic composition of the present invention.

DETAILED DESCRIPTION OF THE INVENTION

The present invention provides for isolated Dirofilaria and Brugia ankyrin proteins, isolated Dirofilaria and Brugia ankyrin nucleic acid molecules, antibodies directed against Dirofilaria and Brugia ankyrin proteins, and compounds able to inhibit parasitic helminth ankyrin function (i.e., inhibitory compounds). As used herein, the terms isolated Dirofilaria ankyrin proteins, isolated Brugia ankyrin proteins, isolated Dirofilaria ankyrin nucleic acid molecules, and isolated Brugia ankyrin nucleic acid molecules refers to ankyrin proteins and ankyrin nucleic acid molecules derived from parasitic helminths of the genera Dirofilaria and Brugia and, as such, can be obtained from their natural source, or can be produced using, for example, recombinant nucleic acid technology or chemical synthesis. Also included in the present invention is the use of these proteins, nucleic acid molecules, antibodies, and inhibitory compounds as therapeutic compositions to protect animals from parasitic helminth diseases as well as in other applications, such as those disclosed below.

The biological functions of ankyrin-related proteins in filariid nematodes are not known. However, inhibiting normal functions of the nervous system in parasitic nematodes might cause neurons to become insensitive to exogenous signals and lead to defects in the development of the parasite. While not being bound by theory, the possible link between neuronal proteins and the development of parasitic nematodes indicates that neuronal proteins, such as ankyrins, could be potential candidates for the development of a vaccine against parasitic nematode infections.

Dirofilaria and Brugia ankyrin proteins and nucleic acid molecules of the present invention have utility because they represent novel targets for anti-parasite vaccines and drugs. The products and processes of the present invention are advantageous because they enable the inhibition of parasite developmental and migratory pathways that involve ankyrin. While not being bound by theory, it is believed that nematode ankyrin-like proteins might affect the development and function of the nematode nervous system, rendering neurons insensitive to exogenous signals involved in migration and development.

Isolation of *D. immitis* and *B. malayi* ankyrin nucleic acid molecules and proteins of the present invention was surprising even in view of the reported *O. volvulus* E1 nucleic acid molecule and protein disclosed by Erttmann, et al., 1996a, ibid., and the reported *C. elegans* UNC-44 nucleic acid molecule and protein disclosed by Otsuka, et al., ibid. As described in more detail in the Examples, it was very difficult to isolate *D. immitis* ankyrin nucleic acid molecules, despite the knowledge of these reported *O. volvulus* and *C. elegans* nucleic acid sequences. Moreover, Erttmann, et al., 1996b, *Trop. Med. Int. Health,* 1, 558–574, teaches away from a *D. immitis* analog of the *O. volvulus* E1 protein, in that the reference discloses that affinity-purified rabbit antibodies raised against the *O. volvulus* E1 protein do not react with *D. immitis* by immunohistochemical analysis (see Erttmann, et al., 1996b, ibid., Table 2).

Furthermore, isolated *D. immitis* and *B. malayi* ankyrin nucleic acid molecules and proteins of the present invention, and particularly *D. immitis* and *B. malayi* ankyrin nucleic acid molecules containing full-length coding regions and full-length *D. immitis* and *B. malayi* ankyrin proteins, are distinct from the *O. volvulus* E1 nucleic acid molecule and protein disclosed by Erttmann, et al., 1996a, ibid. For example, the inventors disclose herein a *D. immitis* ankyrin cDNA molecule of about 5503 nucleotides that encodes a full-length protein of about 1745 amino acids, and has a predicted size of about 191.7 kD. This nucleic acid molecule and protein are in dramatic contrast to the reported *O. volvulus* full-length E1 protein of 462 amino acids (i.e., only about 26% the size of the *D. immitis* full-length protein), and the reported *O. volvulus* E1 full-length cDNA molecule of 2043 nucleotides encoding that protein (i.e. only about 37% the size of the *D. immitis* full-length nucleic acid molecule). The *B. malayi* ankyrin nucleic acid molecule disclosed herein, encoding a non-full-length ankyrin protein, spans a region of the *B. malayi* ankyrin gene that has no similarity to the *O. volvulus* E1 nucleic acid molecule and protein, i.e., the *B. malayi* nucleic acid molecule disclosed herein is in a region 5' to the region that would correspond to the *O. volvulus* E1 nucleic acid molecule and protein.

One embodiment of the present invention is an isolated protein that includes a Dirofilaria ankyrin protein or a Brugia ankyrin protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, an isolated ankyrin protein of the present invention (i.e., a Dirofilaria ankyrin protein or a Brugia ankyrin protein) can be a full-length protein or any homolog of such a protein. An isolated protein of the present invention, including a homolog, can be identified in a straight-forward manner by the protein's ability to elicit an immune response against a Dirofilaria ankyrin protein or a Brugia ankyrin protein. Examples of Dirofilaria and Brugia ankyrin homologs include Dirofilaria and Brugia ankyrin proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of eliciting an immune response against a Dirofilaria or Brugia ankyrin protein, and/or of binding to an antibody directed against a Dirofilaria or Brugia ankyrin protein. That is, when the homolog is administered to an animal as an immunogen, using techniques known to those skilled in the art, the animal will produce an immune response against at least one epitope of a natural Dirofilaria or Brugia ankyrin protein. The ability of a protein to effect an immune response can be measured using techniques known to those skilled in the art. As used herein, the term "epitope" refers to the smallest portion of a protein or other antigen capable of selectively binding to the antigen binding site of an antibody or a T-cell receptor. It is well accepted by those skilled in the art that the minimal size of a protein epitope is about six to seven amino acids.

Dirofilaria and Brugia ankyrin protein homologs can be the result of natural allelic variation or natural mutation. Dirofilaria and Brugia ankyrin protein homologs of the present invention can also be produced using techniques known in the art including, but not limited to, direct modifications to the protein or modifications to the gene encoding the protein using, for example, classic or recombinant DNA techniques to effect random or targeted mutagenesis.

Ankyrin proteins of the present invention are encoded by Dirofilaria ankyrin nucleic acid molecules or Brugia ankyrin nucleic acid molecules. As used herein, a Dirofilaria or Brugia ankyrin nucleic acid molecule includes nucleic acid sequences related to a natural Dirofilaria or Brugia ankyrin gene, and preferably, to a *D. immitis* or a *B. malayi* ankyrin gene. As used herein, a Dirofilaria or Brugia ankyrin gene includes all regions such as regulatory regions that control production of the Dirofilaria or Brugia ankyrin protein encoded by the gene (such as, but not limited to, transcription, translation or post-translation control regions) as well as the coding region itself, and any introns or non-translated coding regions. As used herein, a gene that "includes" or "comprises" a sequence may include that sequence in one contiguous array, or may include the sequence as fragmented exons. As used herein, the term "coding region" refers to a continuous linear array of nucleotides that translates into a protein. A full-length coding region is that coding region that is translated into a full-length, i.e., a complete protein as would be initially translated in its natural millieu, prior to any post-translational modifications. In one embodiment, a *D. immitis* ankyrin gene of the present invention includes the nucleic acid sequence SEQ ID NO:32, as well as the complement of SEQ ID NO:32. Nucleic acid sequence SEQ ID NO:32 represents the deduced sequence of the coding strand of a cDNA (complementary DNA) denoted herein as *D. immitis* ankyrin nucleic acid molecule nDiAnk$_{5503}$, the production of which is disclosed in the Examples. Nucleic acid molecule nDiAnk$_{5503}$ comprises an apparently full-length coding region. The complement of SEQ ID NO:32 (represented herein by SEQ ID NO:34) refers to the nucleic acid sequence of the strand complementary to the strand having SEQ ID NO:32, which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited. It should be noted that since nucleic acid sequencing technology is not entirely error-free, SEQ ID NO:32 (as well as other nucleic acid and protein sequences presented herein) represents an apparent nucleic acid sequence of the nucleic acid molecule encoding a *D. immitis* ankyrin protein of the present invention.

In another embodiment, a *D. immitis* ankyrin gene or nucleic acid molecule can be an allelic variant that includes a similar but not identical sequence to SEQ ID NO:32, SEQ ID NO:34, or any other *D. immitis* nucleic acid sequence cited herein. An allelic variant of a *D. immitis* ankyrin gene including SEQ ID NO:32 and SEQ ID NO:34, is a gene that occurs at essentially the same locus (or loci) in the genome as the gene including SEQ ID NO:32 and SEQ ID NO:34, but which, due to natural variations caused by, for example, mutation or recombination, has a similar but not identical sequence. Because natural selection typically selects against alterations that affect function, allelic variants usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Similarly, a *B. malayi* ankyrin gene or nucleic acid molecule can be an allelic variant that includes a similar but not identical sequence to SEQ ID NO:37 and SEQ ID NO:39. Allelic variants are well known to those skilled in the art and would be expected to be found within a given parasitic helminth such as Dirofilaria or Brugia, since the respective genomes are diploid, and sexual reproduction will result in the reassortment of alleles.

The minimal size of an ankyrin protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As used herein, "stringent hybridization conditions" refer to those experimental conditions under which nucleic acid molecules having similar nucleic acid sequences will anneal to each other. Stringent hybridization conditions typically permit the hybridization of nucleic acid molecules having at least about 70% nucleic acid sequence identity with the nucleic acid molecule being used as a probe in the hybridization reaction. Formulae to calculate the appropriate hybridization and wash conditions to achieve hybridization permitting 30% or less mis-match between two nucleic acid molecules are disclosed, for example, in Meinkoth et al, 1984, *Anal. Biochem* 138, 267–284; Meinkoth et al, ibid, is incorporated by reference herein in its entirety. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an ankyrin protein homolog of the present invention is from about 12 to about 18 nucleotides in length. Thus, the minimal size of an ankyrin protein homolog of the present invention is from about 4 to about 6 amino acids in length. There is no limit, other than a practical limit, on the maximal size of such a nucleic acid molecule in that the nucleic acid molecule can include a portion of a gene, an entire gene, or multiple genes, or portions thereof. The preferred size of a protein encoded by a nucleic acid molecule of the present invention depends on whether a full-length, fusion, multivalent, or functional portion of such a protein is desired.

A preferred Dirofilaria or Brugia ankyrin protein of the present invention is a compound that when administered to an animal in an effective manner, is capable of protecting that animal from disease caused by a parasitic helminth. In accordance with the present invention, the ability of an ankyrin protein of the present invention to protect an animal from disease by a parasitic helminth refers to the ability of that protein to, for example, treat, ameliorate and/or prevent disease caused by parasitic helminths. In one embodiment, a Dirofilaria or Brugia ankyrin protein of the present invention can elicit an immune response (including a humoral and/or cellular immune response) against a parasitic helminth.

Suitable parasites to target include any parasite that is essentially incapable of causing disease in an animal administered a Dirofilaria or Brugia ankyrin protein of the present invention. As such, parasites to target include any parasite that produces a protein having one or more epitopes that can be targeted by a humoral and/or cellular immune response against a Dirofilaria or Brugia ankyrin protein of the present invention and/or that can be targeted by an inhibitory compound that otherwise inhibits ankyrin function (e.g., a compound that binds to ankyrin thereby blocking parasite development and/or migration regulatory pathways), thereby resulting in the decreased ability of the parasite to cause disease in an animal. Preferred parasitic helminths to target include nematodes, cestodes, and trematodes, with nematodes being preferred. Preferred nematodes to target include filariid, ascarid, capillarid, strongylid, strongyloides, trichostrongyle, and trichurid nematodes. Particularly preferred nematodes are those of the genera Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris. Uncinaria, and Wuchereria. Preferred filariid nematodes include Dirofilaria, Onchocerca, Acanthocheilonema, Brugia, Dipetalonema, Loa, Parafilaria, Setaria, Stephanofilaria and Wuchereria filariid nematodes, with *D. immitis* and *B. malayi* being even more preferred.

The present invention also includes mimetopes of Dirofilaria and Brugia ankyrin proteins of the present invention. As used herein, a mimetope of a Dirofilaria or Brugia ankyrin protein of the present invention refers to any compound that is able to mimic the activity of such an ankyrin protein, often because the mimetope has a structure that mimics the particular ankyrin protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of a Dirofilaria or Brugia ankyrin protein of the present invention is a fusion protein that includes a Dirofilaria or Brugia ankyrin protein-containing domain attached to one or more fusion segments. Suitable fusion segments for use with the present invention include, but are not limited to, segments that can: enhance a protein's stability; act as an immunopotentiator to enhance an immune response against a Dirofilaria or Brugia ankyrin protein; and/or assist in purification of a Dirofilaria or Brugia ankyrin protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the Dirofilaria or Brugia ankyrin-containing domain of the protein and can be susceptible to cleavage in order to enable straight-forward recovery of a Dirofilaria or Brugia ankyrin protein. Fusion proteins are preferably produced by culturing a recombinant cell transformed with a fusion nucleic acid molecule that encodes a protein including the fusion segment attached to either the carboxyl and/or amino terminal end of a ankyrin-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. Examples of particularly preferred fusion proteins of the present invention include PHIS-PDiANK$_{288}$, PHIS-PDiANK$_{787}$, PHIS-PDiANK$_{422}$, and PHIS-PDiANK$_{864}$, production of which is disclosed herein.

In another embodiment, a Dirofilaria or Brugia ankyrin protein of the present invention also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds capable of protecting an animal from diseases caused, for example, by at least one infectious agent.

Examples of multivalent protective compounds include, but are not limited to, a Dirofilaria or Brugia ankyrin protein of the present invention attached to one or more compounds protective against one or more other infectious agents, particularly an agent that infects humans, cats, dogs, cattle and/or horses, such as, but not limited to: viruses (e.g., adenoviruses, caliciviruses, coronaviruses, distemper viruses, hepatitis viruses, herpesviruses, immunodeficiency viruses, infectious peritonitis viruses, leukemia viruses, oncogenic viruses, panleukopenia viruses, papilloma viruses, parainfluenza viruses, parvoviruses, rabies viruses, and reoviruses, as well as other cancer-causing or cancer-related viruses); bacteria (e.g., Actinomyces, Bacillus, Bacteroides, Bordetella, Bartonella, Borrelia, Brucella, Campylobacter, Capnocytophaga, Clostridium, Corynebacterium, Coxiella, Dermatophilus, Enterococcus, Ehrlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia; fungi and fungal-related microorganisms (e.g., Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha; and other parasites (e.g., Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, as well as helminth parasites, such as those disclosed herein). In one embodiment, a Dirofilaria or Brugia ankyrin protein of the present invention is attached to one or more additional compounds protective against heartworm disease, elephantiasis, or hydrocele. In another embodiment, one or more protective compounds, such as those listed above, can be included in a multivalent vaccine comprising a Dirofilaria or Brugia ankyrin protein of the present invention and one or more other protective molecules as separate compounds.

A preferred isolated protein of the present invention is a protein encoded by at least one of the following nucleic acid molecules: $nDiAnk_{937}$, $nDiAnk_{936}$, $nDiAnk_{1029}$, $nDiAnk_{810}$, $nDiAnk_{600}$, $nDiAnkl_{1228}$, $nDiAnk_{1227}$, $nDiAnk_{573}$, $nDiAnk_{911}$, $nDiAnk_{909}$, $nDiAnk_{1096}$, $nDiAnk_{1044}$, $nDiAnk_{5503}$, $nDiAnk_{5235}$, $nBmAnk_{908}$, and $nBmAnk_{906}$, or allelic variants of any of these nucleic acid molecules. Another preferred isolated protein is encoded by a nucleic acid molecule the having nucleic acid sequence SEQ ID NO: 1, SEQ ID NO:4, SEQ ID NO:6, SEQ ID NO:9, SEQ ID NO:11, SEQ ID NO:14, SEQ ID NO:17, SEQ ID NO:19, SEQ ID NO:22, SEQ ID NO:25, SEQ ID NO:27, SEQ ID NO:30, SEQ ID NO:32, SEQ ID NO:35, SEQ ID NO:38 and/or SEQ ID NO:40; or an allelic variant of such a nucleic acid molecule.

Translation of SEQ ID NO: 1, the coding strand of $nDiAnk_{937}$, yields a protein of about 312 amino acids, denoted herein as $PDiAnk_{312}$, the amino acid sequence of which is presented in SEQ ID NO:2, assuming a first in-frame codon extending from nucleotide 1 to nucleotide 3 of SEQ ID NO:1. The coding region encoding $PDiAnk_{312}$ is presented herein as $nDiAnk_{936}$, which has the nucleotide sequence SEQ ID NO:4 (the coding strand) and SEQ ID NO:5 (the complementary strand).

Translation of SEQ ID NO:6, the coding strand of $nDiAnk_{1029}$, yields a protein of about 270 amino acids, denoted herein as $PDiAnk_{270}$, the amino acid sequence of which is presented in SEQ ID NO:7, assuming a first in-frame codon extending from nucleotide 2 to nucleotide 4 of SEQ ID NO:6, and a termination codon extending from nucleotide 812 to nucleotide 814 of SEQ ID NO:6. The coding region encoding $PDiAnk_{270}$, not including the termination codon, is presented herein as $nDiAnk_{810}$, which has the nucleotide sequence SEQ ID NO:9 (the coding strand) and SEQ ID NO:10 (the complementary strand). The 147 amino acid residues on the C-terminal end of $PDiAnk_{312}$ lined up with 100% identity to the 147 amino acid residues on the N-terminal end of $PDiAnk_{270}$. $PDiAnk_{270}$ thus represents approximately 123 amino acids of new $D.$ $immitis$ ankyrin amino acid sequence. The presence of a termination codon and a poly-A tail on $nDiAnk_{1029}$ indicates that $nDiAnk_{1029}$ represents the authentic 3' end of the $D.$ $immitis$ ankyrin messenger RNA that was reverse-transcribed into cDNA.

Translation of SEQ ID NO:11, the coding strand of $nDiAnk_{600}$, yields a protein of about 200 amino acids, denoted herein as $PDiAnk_{200}$, the amino acid sequence of which is presented in SEQ ID NO:12, assuming a first in-frame codon extending from nucleotide 1 to nucleotide 3 of SEQ ID NO:11. The 14 amino acid residues on the C-terminal end of $PDiAnk_{200}$ lined up with 100% identity to the 14 amino acid residues on the N-terminal end of $PDiAnk_{312}$. $PDiAnk_{200}$ thus represents approximately 186 amino acids of new $D.$ $immitis$ ankyrin amino acid sequence.

Translation of SEQ ID NO:14, the coding strand of $nDiAnk_{1228}$, yields a protein of about 409 amino acids, denoted herein as $PDiAnk_{409}$, the amino acid sequence of which is presented in SEQ ID NO:15, assuming a first in-frame codon extending from nucleotide 1 to nucleotide 3 of SEQ ID NO:14. The coding region encoding $PDiAnk_{409}$ is presented herein as $nDiAnk_{1227}$, which has the nucleotide sequence SEQ ID NO:17 (the coding strand) and SEQ ID NO:18 (the complementary strand). The 32 amino acid residues on the C-terminal end of $PDiAnk_{409}$ lined up with 100% identity to the 32 amino acid residues on the N-terminal end of $PDiAnk_{200}$. $PDiAnk_{409}$ thus represents about 377 amino acids of new $D.$ $immitis$ ankyrin amino acid sequence.

Translation of SEQ ID NO:19, the coding strand of $nDiAnk_{573}$, yields a protein of about 191 amino acids, denoted herein as $PDiAnk_{191}$, the amino acid sequence of which is presented in SEQ ID NO:20, assuming a first in-frame codon extending from nucleotide 1 to nucleotide 3 of SEQ ID NO:19. The 32 amino acid residues on the C-terminal end of $PDiAnk_{191}$ lined up with 100% identity to the 32 amino acid residues on the N-terminal end of $PDiAnk_{409}$. $PDiAnk_{191}$ thus represents approximately 159 amino acids of new $D.$ $immitis$ ankyrin amino acid sequence.

Translation of SEQ ID NO:22, the coding strand of $nDiAnk_{911}$, yields a protein of about 303 amino acids, denoted herein as $PDiAnk_{303}$, the amino acid sequence of which is presented in SEQ ID NO:23, assuming a first in-frame codon extending from nucleotide 1 to nucleotide 3 of SEQ ID NO:22. The coding region encoding $PDiAnk_{303}$ is presented herein as $nDiAnk_{909}$, which has the nucleotide sequence SEQ ID NO:25 (the coding strand) and SEQ ID NO:26 (the complementary strand). The 54 amino acid residues on the C-terminal end of $PDiAnk_{303}$ lined up with 100% identity to the 54 amino acid residues on the N-terminal end of the $PDiAnk_{409}$. $PDiAnk_{303}$ thus represents approximately 249 amino acids of new $D.$ $immitis$ ankyrin amino acid sequence.

Translation of SEQ ID NO:27, the coding strand of $nDiAnk_{1096}$, yields a protein of about 348 amino acids, denoted herein as $PDiAnk_{348}$, the amino acid sequence of which is presented in SEQ ID NO:28, assuming a start codon extending from nucleotide 51 to nucleotide 53 of SEQ ID NO:27. The nucleic acid molecule representing the coding region encoding $PDiAnk_{348}$, denoted herein as $nDiAnk_{1044}$, is presented herein as SEQ ID NO:30 (the coding strand) and SEQ ID NO:31 (the complementary strand). The about 9 amino acid residues on the C-terminal end of $PDiAnk_{348}$ lined up with about 100% identity to the about 9 amino acid residues on the N-terminal end of the $PDiAnk_{303}$. $PDiAnk_{348}$ thus represents approximately 339 amino acids of new $D.$ $immitis$ ankyrin amino acid sequence.

Translation of SEQ ID NO:32, the coding strand of $nDiAnk_{5503}$, yields a full-length polypeptide of about 1745 amino acids, denoted $PDiAnk_{1745}$, assuming a start codon extending from nucleotide 51 through nucleotide 53 of SEQ ID NO:32, and a stop codon extending from nucleotide 5286 through nucleotide 5285 of SEQ ID NO:32. The resulting amino acid sequence is presented as SEQ ID NO:33. The coding region encoding $PDiAnk_{1745}$, not including the termination codon, is denoted herein as $nDiANK_{5235}$, and has the nucleotide sequence SEQ ID NO:35 (the coding strand) and SEQ ID NO:36 (the complementary strand). SEQ ID NO:35 is predicted to encode a protein with a molecular mass of about 191.7 kD and with a predicted pI of about 5.76, as calculated by the DNAsis program (available from Hitachi Software, San Bruno, Calif.).

A homology search of a non-redundant protein database was performed with SEQ ID NO:33, using the blastp program available through the BLAST™ network of the National Center for Biotechnology Information (NCBI) (National Library of Medicine, National Institutes of Health, Baltimore, Md.), available on the World Wide Web. This database includes SwissProt+PIR+SPupdate+GenPept+ GPUpdate+PDB databases. The highest scoring match of the homology search at amino acid level was GenBank™ accession number gil1208874, a *C. elegans* ankyrin-like protein, to which SEQ ID NO:33 showed about 69% identity, spanning from about amino acid 1 through about amino acid 1745 of SEQ ID NO:33. The second highest scoring match of the homology search at amino acid level was GenBank™ accession number gil406288, a human brain ankyrin protein (variant I, Ankyrin$_B$), to which SEQ ID NO:33 showed about 51% identity, spanning from about amino acid 1 through about amino acid 1745.

SEQ ID NO:33 was also compared with the protein sequence of the *O. volvulus* E1 protein as disclosed by Erttmann, et al., 1996a, ibid. A region of SEQ ID NO:33 spanning from about amino acid 1282 to about amino acid 1745 showed about 78% identity to the 462-amino acid *O. volvulus* E1 protein. At the nucleotide level, the cDNA encoding SEQ ID NO:33 (i.e., SEQ ID NO:32) was compared to the cDNA encoding the *O. volvulus* E1 protein. A region of SEQ ID NO:32 spanning from about nucleotide 3423 to about nucleotide 5474 showed about 88% nucleic acid identity to the cDNA encoding the *O. volvulus* E1 protein.

Translation of SEQ ID NO:37, the coding strand of nBmAnk$_{908}$, yields a non-full-length polypeptide of about 302 amino acids, denoted PBmAnk$_{302}$, assuming a first in-frame codon extending from nucleotide 1 through nucleotide 3 of SEQ ID NO:37. The resulting amino acid sequence is presented as SEQ ID NO:38. The coding region encoding PBmAnk$_{302}$ is denoted herein as nBmANK$_{906}$, and has the nucleotide sequence SEQ ID NO:40 (the coding strand) and SEQ ID NO:41 (the complementary strand).

A homology search of a non-redundant protein database was performed on SEQ ID NO:38 using the BLAST network. The homology spans from about amino acid 1 through amino acid 302 of SEQ ID NO:38. The highest scoring match of the homology search at amino acid level was GenBank accession number A57282, a *C. elegans* ankyrin-like protein, which was about 86% identical to SEQ ID NO:38 through a region extending from about amino acid 353 through about amino acid 654 of A57282.

The amino acid sequence of SEQ ID NO:38 was also compared to *D. immitis* ankyrin protein PDiAnk$_{1745}$ (i.e. SEQ ID NO:33 of the present invention). PBmAnk$_{302}$ had 95% identity to the region of SEQ ID NO:33 spanning from about amino acid 341 through about amino acid 642.

Preferred ankyrin proteins of the present invention include proteins that are at least about 75%, preferably at least about 80%, more preferably at least about 85%, even more preferably at least about 90%, and even more preferably at least about 95% identical to PDiAnk$_{1745}$; or are at least about 90%, and preferably at least about 95%, identical to PBmAnk$_{302}$. More preferred are ankyrin proteins comprising PDiAnk$_{312}$, PDiAnk$_{270}$, PDiAnk$_{200}$, PDiAnk$_{409}$, PDiAnk$_{191}$, PDiAnk$_{303}$, PDiAnk$_{348}$, PDiAnk$_{1745}$, or PBmAnk$_{302}$; and proteins encoded by allelic variants of a nucleic acid molecules encoding proteins PDiAnk$_{312}$, PDiAnk$_{270}$, PDiAnk$_{200}$, PDiAnk$_{409}$, PDiAnk$_{191}$, PDiAnk$_{303}$, PDiAnk$_{348}$, PDiAnk$_{1745}$, or PBmAnk$_{302}$.

Other preferred ankyrin proteins of the present invention include proteins having amino acid sequences that are at least about 75%, preferably at least about 80%, more preferably at least about 85%, even more preferably at least about 90%, and even more preferably at least about 95% identical to amino acid sequence SEQ ID NO:33; or proteins having amino acid sequences that are at least about 90%, and preferably at least about 95%, identical to SEQ ID NO:38. More preferred are ankyrin proteins comprising amino acid sequences SEQ ID NO:2, SEQ ID NO:7, SEQ ID NO:12, SEQ ID NO:15, SEQ ID NO:20, SEQ ID NO:23, SEQ ID NO:28, SEQ ID NO:33 and/or SEQ ID NO:38; and ankyrin proteins encoded by allelic variants of nucleic acid molecules encoding ankyrin proteins having amino acid sequences SEQ ID NO:2, SEQ ID NO:7, SEQ ID NO:12, SEQ ID NO:15, SEQ ID NO:20, SEQ ID NO:23, SEQ ID NO:28, SEQ ID NO:33 and/or SEQ ID NO:38.

Particularly preferred Dirofilaria ankyrin proteins of the present invention comprise amino acid sequence SEQ ID NO:33 (including, but not limited to, the proteins consisting of amino acid sequence SEQ ID NO:33, fusion proteins and multivalent proteins), and proteins encoded by allelic variants of nucleic acid molecules encoding proteins having amino acid sequence SEQ ID NO:33; and particularly preferred Brugia ankyrin proteins of the present invention comprise amino acid sequence SEQ ID NO:38 (including, but not limited to, the proteins consisting of SEQ ID NO:38, fusion proteins and multivalent proteins), and proteins encoded by allelic variants of nucleic acid molecules encoding proteins having amino acid sequence SEQ ID NO:38.

In one embodiment, a preferred *D. immitis* or *B. malayi* ankyrin protein of the present invention comprises an amino acid sequence of at least about 500 amino acids, preferably at least about 1000 amino acids, and even more preferably at least about 1500 amino acids. Within this embodiment, a preferred *D. immitis* ankyrin protein of the present invention has an amino acid sequence comprising at least a portion of SEQ ID NO:33. In another embodiment, a preferred *D. immitis* or *B. malayi* ankyrin protein comprises a full-length protein, i.e., a protein encoded by a full-length coding region. A particularly preferred apparently full-length ankyrin protein is PDiAnk$_{1745}$.

Additional preferred ankyrin proteins of the present invention include proteins encoded by nucleic acid molecules comprising at least a portion of nDiAnk$_{937}$, nDiAnk$_{936}$, nDiAnk$_{1029}$, nDiAnk$_{810}$, nDiAnk$_{600}$, nDiAnk$_{1228}$, nDiAnk$_{1227}$, nDiAnk$_{573}$, nDiAnk$_{911}$, nDiAnk$_{909}$, nDiAnk$_{1096}$, nDiAnk$_{10448}$, nDiAnk$_{5503}$, nDiAnk$_{5235}$, nBmAnk$_{908}$, and/or nBmAnk$_{906}$, as well as ankyrin proteins encoded by allelic variants of such nucleic acid molecules.

Also preferred are ankyrin proteins encoded by nucleic acid molecules having nucleic acid sequences comprising at least a portion of SEQ ID NO:1, SEQ ID NO:4, SEQ ID NO:6, SEQ ID NO:9, SEQ ID NO:11, SEQ ID NO:14, SEQ ID NO:17, SEQ ID NO:19, SEQ ID NO:22, SEQ ID NO:25, SEQ ID NO:27, SEQ ID NO:30, SEQ ID NO:32, SEQ ID NO:35, SEQ ID NO:37 and/or SEQ ID NO:40, as well as allelic variants of these nucleic acid molecules.

In another embodiment, a preferred Dirofilaria or Brugia ankyrin protein of the present invention is encoded by a nucleic acid molecule comprising at least about 1500 nucleotides, preferably at least about 3000 nucleotides and more preferably at least about 4500 nucleotides. Within this embodiment is an ankyrin protein encoded by at least a portion nDiAnk$_{5503}$ or by an allelic variant of this nucleic acid molecule. In yet another embodiment, a preferred Dirofilaria or Brugia ankyrin protein of the present invention is encoded by a nucleic acid molecule comprising an apparently full-length ankyrin coding region, i.e., a nucleic acid molecule encoding an apparently full-length ankyrin protein.

Another embodiment of the present invention is an isolated nucleic acid molecule comprising either a Dirofilaria ankyrin nucleic acid molecule or a Brugia ankyrin nucleic acid molecule. The identifying characteristics of such nucleic acid molecules is heretofore described. A nucleic acid molecule of the present invention can include an isolated natural Dirofilaria or Brugia ankyrin gene or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of an ankyrin nucleic acid molecule of the present invention is from about 12 to about 18 nucleotides in length. Preferred ankyrin nucleic acid molecules include *D. immitis* ankyrin nucleic acid molecules and *B. malayi* ankyrin nucleic acid molecules.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. An isolated Dirofilaria or Brugia ankyrin nucleic acid molecule of the present invention can be isolated from its natural source or produced using recombinant DNA technology (e.g., polymerase chain reaction (PCR) amplification or cloning) or chemical synthesis. Isolated Dirofilaria or Brugia ankyrin nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode an ankyrin protein of the present invention.

A Dirofilaria or Brugia ankyrin nucleic acid molecule homolog can be produced using a number of methods known to those skilled in the art, see, for example, Sambrook et al., 1989, *Molecular Cloning: A Laboratory Manual,* Cold Spring Harbor Labs Press; Sambrook et al., ibid., is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologs can be selected by hybridization with a Dirofilaria or Brugia ankyrin nucleic acid molecule or by screening the function of a protein encoded by the nucleic acid molecule (e.g., ability to elicit an immune response against at least one epitope of a Dirofilaria or Brugia ankyrin protein).

An isolated nucleic acid molecule of the present invention can include a nucleic acid sequence that encodes at least one Dirofilaria or Brugia ankyrin protein of the present invention, examples of such proteins being disclosed herein.

Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a Dirofilaria or Brugia ankyrin protein.

A preferred nucleic acid molecule of the present invention, when administered to an animal, is capable of protecting that animal from disease caused by a parasitic helminth. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein (e.g., an ankyrin protein of the present invention), the nucleic acid molecule being delivered to the animal, for example, by direct injection (i.e, as a genetic vaccine) or in a vehicle such as a recombinant virus vaccine or a recombinant cell vaccine.

One embodiment of the present invention is an ankyrin nucleic acid molecule comprising all or part of nucleic acid molecules $nDiAnk_{937}$, $nDiAnk_{936}$, $nDiAnk_{1029}$, $nDiAnk_{810}$, $nDiAnk_{600}$, $nDiAnk_{228}$, $nDiAnk_{1227}$, $nDiAnk_{573}$, $nDiAnk_{911}$, $nDiAnk_{909}$, $nDiAnk_{1096}$, $nDiAnk_{1044}$, $nDiAnk_{5503}$, $nDiAnk_{5235}$, $nBmAn_{908}$, or $nBmAnk_{906}$, or allelic variants of these nucleic acid molecules. Another preferred nucleic acid molecule of the present invention includes at least a portion of nucleic acid sequence SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:16, SEQ ID NO:17, SEQ ID NO:18, SEQ ID NO:19, SEQ ID NO:21, SEQ ID NO:22, SEQ ID NO:24, SEQ ID NO:25, SEQ ID NO:26, SEQ ID NO:27, SEQ ID NO:29, SEQ ID NO:30, SEQ ID NO:31, SEQ ID NO:32, SEQ ID NO:34, SEQ ID NO:35, SEQ ID NO:36, SEQ ID NO:37, SEQ ID NO:39, SEQ ID NO:40, and/or SEQ ID NO:41, as well as allelic variants of nucleic acid molecules having these nucleic acid sequences. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

In one embodiment, an ankyrin nucleic acid molecule of the present invention encodes a protein that is at least about 75%, preferably at least about 80%, more preferably at least about 85%, even more preferably at least about 90%, and even more preferably at least about 95% identical to $PDiAnk_{1745}$; or is at least about 90%, and preferably at least about 95%, identical to $PBmAnk_{302}$. Even more preferred is a nucleic acid molecule encoding $PDiAnk_{312}$, $PDiAnk_{270}$, $PDiAnk_{200}$, $PDiAnk_{409}$, $PDiAnk_{191}$, $PDiAnk_{303}$, $PDiAnk_{348}$, $PDiAnk_{1745}$, $PBmAnk_{302}$, and/or an allelic variant of such a nucleic acid molecule.

In another embodiment, an ankyrin nucleic acid molecule of the present invention encodes a protein having an amino acid sequence that is at least about 75%, preferably at least about 80%, more preferably at least about 85%, even more preferably at least about 90%, and even more preferably at least about 95% identical to SEQ ID NO:33; or is at least about 90%, and preferably at least about 95%, identical to SEQ ID NO:38. The present invention also includes an ankyrin nucleic acid molecule encoding a protein having at least a portion of SEQ ID NO:2, SEQ ID NO:7, SEQ ID NO:12, SEQ ID NO:15, SEQ ID NO:20, SEQ ID NO:23, SEQ ID NO:28, SEQ ID NO:33 and/or SEQ ID NO:38, as well as allelic variants of an ankyrin nucleic acid molecule encoding a protein having these sequences, including nucleic acid molecules that have been modified to accommodate codon usage properties of the cells in which such nucleic acid molecules are to be expressed.

In another embodiment, a preferred Dirofilaria or Brugia ankyrin nucleic acid molecule encodes an ankyrin protein comprising at least about 500 amino acids, preferably at least about 1000 amino acids, and more preferably at least about 1500 amino acids; i.e., an ankyrin nucleic acid molecule that comprises a contiguous ankyrin coding region of at least about 1500 nucleotides, preferably at least about 3000 nucleotides, and more preferably at least about 4500 nucleotides.

In yet another embodiment, a preferred Dirofilaria or Brugia ankyrin nucleic acid molecule of the present invention comprises an apparently full-length ankyrin coding region, i.e., the preferred nucleic acid molecule encodes an apparently full-length ankyrin protein.

Knowing the nucleic acid sequences of certain Dirofilaria or Brugia ankyrin nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other Dirofilaria or Brugia ankyrin nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include Dirofilaria or Brugia L3, L4 or adult cDNA libraries as well as genomic DNA libraries. Similarly, preferred DNA sources from which to amplify nucleic acid molecules include Dirofilaria or Brugia L3, L4 or adult cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising Dirofilaria or Brugia ankyrin nucleic acid molecules or other parasitic helminth ankyrin nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of about 100 nucleotides. The present invention includes oligonucleotides that can be used as, for example, probes to identify nucleic acid molecules, primers to produce nucleic acid molecules, or therapeutic reagents to inhibit Dirofilaria or Brugia ankyrin protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of Dirofilaria and Brugia ankyrin nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other endoparasite, or insect and mammalian cells, such as, but not limited to, tac, lac, trp, trc, oxy-pro, omp/lpp, rrnB, bacteriophage lambda (such as lambda $P_L$ and lambda $P_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with parasitic helminths, such as $D$ immitis or $B.$ malayi transcription control sequences.

Suitable and preferred nucleic acid molecules to include in recombinant vectors of the present invention are as disclosed herein. Preferred nucleic acid molecules to include in recombinant vectors, and particularly in recombinant molecules, include $nDiAnk_{937}$, $nDiAnk_{936}$, $nDiAnk_{1029}$, $nDiAnk_{810}$, $nDiAnk_{600}$, $nDiAnkl_{1228}$, $nDiAnk_{1227}$, $nDiAnk_{573}$, $nDiAnk_{911}$, $nDiAnk_{909}$, $nDiAnk_{1096}$, $nDiAnk_{1044}$, $nDiAnk_{5503}$, $nDiAnk_{5235}$, $nBmAnk_{908}$, and $nBmAnk_{906}$. Particularly preferred recombinant molecules of the present invention include $pTrc$-$nDiAnk_{1866}$, $pTrc$-$nDiAnk_{2361}$, $pTrc$-$nDiAnk_{1266}$, and $pTrc$-$nDiAnk_{864}$, the production of which are described in the Examples section.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include Dirofilaria and Brugia ankyrin nucleic acid molecules disclosed herein. Particularly preferred nucleic acid molecules with which to transform a cell include $nDiAnk_{937}$, $nDiAnk_{936}$, $nDiAnk_{1029}$, $nDiAnk_{810}$, $nDiAnk_{600}$, $nDiAnk_{1228}$, $nDiAnk_{1227}$, $nDiAnk_{573}$, $nDiAnk_{911}$, $nDiAnk_{909}$, $nDiAnk_{1096}$, $nDiAnk_{1044}$, $nDiAnk_{5503}$, $nDiAnk_{5235}$, $nBmAnk_{908}$, and $nBmAnk_{906}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing Dirofilaria or Brugia ankyrin proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are Escherichia coli, including $E.$ coli K-12 derivatives; Salmonella typhi; Salmonella typhimurium, including attenuated strains such as UK-1 $_\chi$3987 and SR-11 $_\chi$4072; Spodoptera frugiperda; Trichoplusia ni; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, $LMTK^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein. Particularly preferred recombinant molecules include $pTrc$-$nDiAnkl_{1866}$, $pTrc$-$nDiAnk_{2361}$, $pTrc$-$nDiAnk_{1266}$, and $pTrc$-$nDiAnk_{864}$.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein. Particularly preferred recombinant cells include $E.$ coli:$pTrc$-$nDiAnk_{1866}$, $E.$ coli:$pTrc$-$nDiAnk_{2361}$, $E.$ coli:$pTrc$-$nDiAnk_{1266}$, and $E.$ coli:$pTrc$-$nDiAnk_{864}$. Details regarding the production of these recombinant cells are disclosed herein.

Recombinant cells of the present invention can also be co-transformed with one or more recombinant molecules including Dirofilaria or Brugia ankyrin nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated Dirofilaria or Brugia ankyrin proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a Dirofilaria or Brugia ankyrin protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli;* or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a Dirofilaria or Brugia ankyrin protein of the present invention or a mimetope thereof (e.g., anti-Dirofilaria ankyrin antibodies or anti-Brugia ankyrin antibodies). As used herein, the term "selectively binds to" an ankyrin protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual,* Cold Spring Harbor Labs Press; Harlow et al., ibid., is incorporated by reference herein in its entirety. An anti-ankyrin antibody of the present invention preferably selectively binds to a Dirofilaria or Brugia ankyrin protein in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce ankyrin proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such helminths and/or (c) as tools to screen expression libraries and/or to recover desired proteins of the present invention from a mixture of proteins and other contaminants. Furthermore, antibodies of the present invention can be used to target cytotoxic agents to parasitic helminths in order to directly kill such helminths. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from disease caused by a parasitic helminth. Therapeutic compositions of the present invention include at least one of the following protective compounds: an isolated Dirofilaria or Brugia ankyrin protein or a mimetope thereof, an isolated Dirofilaria or Brugia ankyrin nucleic acid molecule, an isolated antibody that selectively binds to a Dirofilaria or Brugia ankyrin protein, an inhibitor of ankyrin function identified by its ability to bind to a Dirofilaria or Brugia ankyrin protein and thereby impede development and/or migration of the parasite, and a mixture thereof (i.e., combination of at least two of the compounds). As used herein, a protective compound refers to a compound that, when administered to an animal in an effective manner, is able to treat, ameliorate, and/or prevent disease caused by a parasitic helminth. Preferred helminths to target are heretofore disclosed. Examples of proteins, nucleic acid molecules, antibodies and inhibitors of the present invention are disclosed herein.

The present invention also includes a therapeutic composition comprising at least one Dirofilaria or Brugia ankyrin-based compound of the present invention in combination with at least one additional compound protective against one or more infectious agents. Examples of such compounds and infectious agents are disclosed herein.

Therapeutic compositions of the present invention can be administered to any animal susceptible to such therapy, preferably to mammals, and more preferably to dogs, cats, humans, ferrets, horses, cattle, sheep and other pets, economic food animals and/or zoo animals. Preferred animals to protect against heartworm disease include dogs, cats, humans and ferrets, with dogs and cats being particularly preferred. The preferred animals to protect against elephantiasis and hydrocele include humans.

In one embodiment, a therapeutic composition of the present invention can be administered to the vector in which the parasitic helminth develops, such as to a mosquito in order to prevent the spread of heartworm. Such administration could be oral or by developing transgenic vectors capable of producing at least one therapeutic composition of the present invention. In another embodiment, an insect vector, such as a mosquito, can ingest therapeutic compositions present in the blood of a host that has been administered a therapeutic composition of the present invention.

In order to protect an animal from disease caused by a parasitic helminth, a therapeutic composition of the present invention is administered to the animal in an effective manner such that the composition is capable of protecting that animal from a disease caused by a parasitic helminth. Therapeutic compositions of the present invention can be administered to animals prior to infection in order to prevent infection (i.e., as a preventative vaccine) and/or can be administered to animals after infection in order to treat disease caused by the parasitic helminth (i.e., as a therapeutic vaccine).

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T-cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposhperes, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Therapeutic compositions of the present invention can be administered to animals prior to infection in order to prevent infection and/or can be administered to animals after infection in order to treat disease caused by the parasitic helminth. For example, proteins, mimetopes thereof, and antibodies thereof can be used as immunotherapeutic agents. Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome (i.e., a viral vector). Preferred viral vectors include those based on alphaviruses, poxviruses, adenoviruses, herpesviruses, picornaviruses, and retroviruses, with those based on alphaviruses (such as sindbis or Semliki forest virus), species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, intranasal and oral routes of administration being preferred. A preferred single dose of a genetic vaccine ranges from about 1 nanogram (ng) to about 600 $\mu$g, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from disease caused by a parasitic helminth as disclosed herein. For example, a recombinant virus vaccine comprising an ankyrin nucleic acid molecule of the present invention is administered according to a protocol that results in the animal producing a sufficient immune response to protect itself from heartworm. A preferred single dose of a recombinant virus vaccine of the present invention is from about $1 \times 10^4$ to about $1 \times 10^8$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Challenge studies can include implantation of chambers including parasitic helminth larvae into the treated animal and/or direct administration of larvae to the treated animal. In one embodiment, therapeutic compositions can be tested in animal models such as mice. Such techniques are known to those skilled in the art.

One preferred embodiment of the present invention is the use of Dirofilaria or Brugia ankyrin proteins, nucleic acid molecules, antibodies and inhibitors of the present invention, to protect an animal from heartworm. It is particularly preferred to prevent L3 that are delivered to the animal by the mosquito intermediate host from migrating from the site of inoculation and/or maturing into adult worms. As such, preferred therapeutic compositions are those that are able to inhibit at least one step in the portion of the parasite's development cycle that includes L3, third molt, L4, fourth molt, immature adult prior to entering the circulatory system. In dogs, this portion of the development cycle is about 70 days. Particularly preferred therapeutic compositions include *D. immitis* ankyrin-based therapeutic compositions of the present invention. Such compositions include *D. immitis* ankyrin nucleic acid molecules, *D. immitis* ankyrin proteins and mimetopes thereof, anti-*D. immitis* ankyrin antibodies, and inhibitors of *D. immitis* ankyrin function. Therapeutic compositions are administered to animals in a manner effective to protect the animals from heartworm. Additional protection may be obtained by administering additional protective compounds, including other parasitic helminth proteins, nucleic acid molecules, antibodies and inhibitory compounds, as disclosed herein.

One therapeutic composition of the present invention includes an inhibitor of Dirofilaria or Brugia ankyrin function, i.e., a compound capable of substantially interfering with the function of a Dirofilaria or Brugia ankyrin protein susceptible to inhibition. For example, an isolated protein or mimetope thereof is administered in an amount and manner that elicits (i.e., stimulates) an immune response that is sufficient, upon interaction with a native ankyrin protein, to protect the animal from the disease. Similarly, an antibody of the present invention, when administered to an animal in an effective manner, is administered in an amount so as to be present in the animal at a titer that is sufficient, upon interaction of that antibody with a native ankyrin protein, to protect the animal from the disease, at least temporarily. Oligonucleotide nucleic acid molecules of the present invention can also be administered in an effective manner, thereby reducing expression of Dirofilaria or Brugia ankyrin proteins in order to interfere with development of parasitic helminths targeted in accordance with the present invention. Methods to identify certain functions, i.e., protein-binding capabilities, of Dirofilaria or Brugia ankyrin proteins of the present invention are disclosed herein.

One embodiment of the present invention is a method to identify proteins that specifically interact with an ankyrin protein of the present invention. The method can comprise the steps of a) identifying and isolating a protein-binding domain of an isolated Dirofilaria or Brugia ankyrin protein; b) contacting that protein-binding domain with isolated parasitic helminth proteins under conditions such that a parasitic helminth protein and the protein-binding domain can selectively interact and/or bind to each other, using, for example, the yeast two-hybrid system see, for example, Luban, et al., 1995, *Curr. Opin. Biotechnol.*, 6, 59–64; and c) identifying those proteins that specifically bind to the isolated ankyrin protein-binding domain. Additional methods to identify protein-protein interactions with the protein-binding domains of an isolated ankyrin protein of the present invention are known to those skilled in the art. Examples include Biacore® screening, confocal immunofluorescent microscopy, and immunoprecipitations.

An inhibitor of ankyrin function can be identified using Dirofilaria or Brugia ankyrin proteins of the present invention. One embodiment of the present invention is a method to identify a compound capable of inhibiting ankyrin function of a parasitic helminth. Such a method includes the steps of: (a) identifying a protein binding or regulatory activity of an isolated ankyrin protein in vitro; (b) identifying a putative compound capable of binding to and/or inhibiting the identified protein binding or regulatory activity of the isolated ankyrin protein; (c) contacting *D. immitis* L3 larvae with the putative inhibitory compound under conditions in which, in the absence of the compound, the larvae are able to molt to the L4 stage; and (d) determining if the putative compound inhibits molting. Putative inhibitory compounds to screen include small organic molecules, antibodies (including mimetopes thereof), and ligand analogs. Such compounds are also screened to identify those that are substantially not toxic in host animals.

Inhibitors of ankyrin function identified by such a method can be tested for their ability to block development and/or migration of parasitic helminths, and particularly of *D. immitis* and *B. malayi,* in vivo. Preferred ankyrin proteins to inhibit are those produced by parasitic helminths, even more preferred ankyrin proteins to inhibit are those produced by filariid nematodes. A particularly preferred inhibitor of the present invention is capable of protecting an animal from heartworm disease, elephantiasis and/or hydrocele. It is also within the scope of the present invention to use inhibitors of the present invention to target diseases caused by parasitic helminths in animals. Compositions comprising inhibitors of ankyrin function can be administered to animals in an effective manner to protect animals from disease caused by parasitic helminths, and preferably to protect animals from heartworm disease, elephantiasis and/or hydrocele. Effective amounts and dosing regimens can be determined using techniques known to those skilled in the art.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can specifically detect all phases of the parasite's life cycle. Methods to use such diagnostic reagents to diagnose parasitic helminth infection are well known to those skilled in the art. Suitable and preferred parasitic helminths to detect are those to which therapeutic compositions of the present invention are targeted. Particularly preferred parasitic helminths to detect using diagnostic reagents of the present invention are *D. immitis* and *B. malayi.*

The following examples are provided for the purposes of illustration and are not intended to limit the scope of the present invention.

EXAMPLES

It is to be noted that the examples include a number of molecular biology, microbiology, immunology and biochemistry techniques considered to be familiar to those skilled in the art. Disclosure of such techniques can be found, for example, in Sambrook et al., ibid. and Ausubel, et al., 1993, *Current Protocols in Molecular Biology*, Greene/Wiley Interscience, New York, N.Y., and related references. Ausubel, et al, ibid. is incorporated by reference herein in its entirety. DNA sequence analyses and protein translations were carried out using the DNAsis program (available from Hitachi Software, San Bruno, Calif.). It should also be noted that since nucleic acid sequencing technology, and in particular the sequencing of PCR products, is not entirely error-free, that the nucleic acid and deduced protein sequences presented herein represent apparent nucleic acid sequences of the nucleic acid molecules encoding D. immitis ankyrin proteins of the present invention.

Example 1

This example describes the isolation and sequencing of several D. immitis ankyrin nucleic acid molecules. It is to be noted that some of the nucleic acid molecules disclosed in this example were isolated by PCR with degenerate primers and/or primers not fully identical to the D. immitis sequences. The authentic D. immitis nucleotide sequences were verified on overlapping nucleic acid molecules, and thus the nucleotide sequences of the nucleic acid molecules disclosed in this example are fully representative of D. immitis sequences.

A. As a first step in the isolation of a full-length ankyrin cDNA molecule from D. immitis, a D. immitis ankyrin nucleic acid molecule of about 937 nucleotides, denoted herein as nDiAnk$_{937}$, was isolated from a D. immitis cDNA library by PCR amplification for use as a probe, as follows. A D. immitis 48-hour L3 cDNA library was constructed in the Uni-ZAP® XR vector (available from Stratagene Cloning Systems, La Jolla, Calif.), using Stratagene's ZAP-cDNA® Synthesis Kit protocol and L3 mRNAs (i.e., messenger RNAs isolated from D. immitis third-stage larvae, harvested at 48 hours). Initially, degenerate primers were designed based on conserved regions of the C. elegans UNC-44 gene described in Otsuka, et al., ibid. These initial attempts to PCR-amplify an ankyrin-related nucleic acid molecule from the D. immitis cDNA library were unsuccessful. In a second attempt, PCR primers were designed based on the Onchocerca volvulus E1 gene disclosed in Erttmann, et al., 1996a, ibid. These primers included forward primer OVANKY 554+, having the nucleotide sequence 5' CATCAATTTT TGGAATTTTC TGG 3', denoted herein as SEQ ID NO:42 and reverse primer OVANKY 1464–, having the nucleotide sequence 5' CGTT-TACAGC AACATCATCC TC 3', denoted herein as SEQ ID NO:43. Several attempts to amplify an ankyrin-related nucleic acid molecule from the D. immitis cDNA library with these primers using standard PCR amplification conditions were likewise unsuccessful. Finally, the same primers were used in a modified amplification procedure called "touchdown" PCR. This procedure included the following amplification cycles: six cycles of 94° C. for 30 sec, 58° C. for 45 sec, and 72° C. for 3 min; six cycles of 94° C. for 30 sec, 56° C. for 45 sec, and 72° C. for 3 min; and 20 cycles of 94° C. for 30 sec, 50° C. for 45 sec, and 72° C. for 3 min. An about 937-base-pair (bp) DNA fragment was detected in the PCR reaction by agarose gel electrophoresis. The PCR-amplified fragment, denoted herein as nDiAnk$_{937}$, was excised from the gel and purified using the QIAquick™ kit (available from Qiagen, Chatsworth, Calif.) as per manufacturer's instructions. The resultant 937-bp DNA fragment was subcloned into the pCRII™ vector (available from Invitrogen, San Diego, Calif.) according to the manufacturer's instructions.

The nucleic acid molecule nDiAnk$_{937}$ was sequenced by the Sanger dideoxy chain termination method, using the PRISM™ Ready Dye Terminator Cycle Sequencing Kit with AmpliTaq® DNA Polymerase, FS (available from the Perkin-Elmer Corporation, Norwalk, Conn.). PCR extensions were done in the GeneAmp™ PCR System 9600 (available from Perkin-Elmer). Excess dye terminators were removed from extension products using the Centriflex™ Gel Filtration Cartridge (available from Advanced Genetics Technologies Corporation, Gaithersburg, Md.) following the standard protocol. Samples were resuspended according to ABI protocols and were run on a Perkin-Elmer ABI PRISM™ 377 Automated DNA Sequencer. The resulting nucleic acid sequence of nDiAnk$_{937}$ is presented herein as SEQ ID NO:1 (the coding strand) and SEQ ID NO:3 (the complementary strand).

Translation of SEQ ID NO:1 yields a protein of about 312 amino acids, denoted herein as PDiAnk$_{312}$, the amino acid sequence of which is presented in SEQ ID NO:2, assuming a first in-frame codon extending from nucleotide 1 to nucleotide 3 of SEQ ID NO:1. The coding region encoding PDiAnk$_{315}$ is presented herein as nDiAnk$_{936}$, which has the nucleotide sequence SEQ ID NO:4 (the coding strand) and SEQ ID NO:5 (the complementary strand).

B. An additional ankyrin nucleic acid molecule of about 1029 bp, containing the authentic 3' end of a D. immitis ankyrin coding region, was isolated as follows.

Nucleic acid molecule nDiAnkg$_{937}$, isolated as disclosed in Example 1A, was used as a hybridization probe to screen a D. immitis 48-hour L3 cDNA library. Nucleic acid molecule nDiAnk$_{937}$ was labeled with α-[$^{32}$P] dATP using the Megaprime™ Kit, available from Amersham, Arlington Heights, Ill.. The labeled probe was then hybridized and washed under stringent conditions (i.e., allowing at most about 3% bp mismatch) to about 5×10$^5$ plaque forming units of an D. immitis 48-hour L3 cDNA library, constructed as disclosed in Example 1A. Fifteen plaques that hybridized with the labeled probe were selected and subjected to three rounds of plaque purification. The size and identity of the bacteriophage clones that hybridized with the probe were identified by PCR amplification using vector-specific primers, and subsequent Southern hybridization of the separated PCR-amplified DNA fragments, using nDiAnk$_{937}$ as a probe. Of these 15 clones, none had inserts larger than about 1.1 kilobases (kb). One positively hybridizing clone having an insert of about 1029 bp was chosen for further study. The insert from this cDNA clone, denoted herein as nDiAnk$_{1029}$, was PCR-amplified with a T3/T7 primer set (available from Stratagene), and was subcloned into the pCRII™ vector. The resulting plasmid, containing nucleic acid molecule nDiAnk$_{1029}$, was subjected to automated sequencing as described in Example 1A. The nucleotide sequence of nDiAnk$_{1029}$ is presented herein as SEQ ID NO:6 (the coding strand) and SEQ ID NO:8 (the complementary strand). The 443 nucleotides on the 3' end of nDiAnk$_{937}$ lined up with 100% identity to the 443 nucleotides on the 5' end of nDiANK$_{1029}$.

Translation of SEQ ID NO:6 yields a protein of about 270 amino acids, denoted herein as PDiAnk$_{270}$, the amino acid sequence of which is presented in SEQ ID NO:7, assuming a first in-frame codon extending from nucleotide 2 to nucleotide 4 of SEQ ID NO:6, and a termination codon extending from nucleotide 812 to nucleotide 814 of SEQ ID NO:6. The coding region encoding PDiAnk$_{270}$, not including the termination codon, is presented herein as nDiAnk$_{810}$, which has the nucleotide sequence SEQ ID NO:9 (the coding strand) and SEQ ID NO:10 (the complementary strand). The 147 amino acid residues on the C-terminal end of PDiAnk$_{312}$, (disclosed in Example 1A) lined up with 100% identity to the 147 amino acid residues on the N-terminal end of PDiAnk$_{270}$. PDiAnk$_{270}$ thus represents approximately 123 amino acids of new *D. immitis* ankyrin amino acid sequence. The presence of a termination codon and a poly-A tail on nDiAnkI$_{1029}$ indicates that nDiAnk$_{1029}$ represents the authentic 3' end of the *D. immitis* ankyrin messenger RNA that was reverse-transcribed into cDNA.

C. An additional ankyrin nucleic acid molecule of about 600 bp was isolated by PCR-amplification from a *D. immitis* 48-hour L3 cDNA library, as follows.

Since nDiAnk$_{937}$ (isolated as disclosed in Example 1A) extended beyond the 5' end of nDiAnk$_{1029}$ (isolated as disclosed in Example 1B) by 495 bp, nDiAnk$_{1029}$ did not appear to represent a full-length ankyrin cDNA molecule. Furthermore, nDiAnk$_{937}$ did not appear to contain the authentic 5' end of a full-length ankyrin cDNA molecule. This result suggested that the *D. immitis* ankyrin messenger RNA was larger, but was not represented as cDNA at hybridization-detectable levels in the *D. immitis* L3 cDNA library utilized in these experiments. Therefore, isolation of additional portions of a full-length *D. immitis* ankyrin nucleic acid molecule were carried out by PCR amplification. An about 600-bp *D. immitis* ankyrin nucleic acid molecule was amplified by PCR from a *D. immitis* 48-hour L3 cDNA library, constructed as described in Example 1A, using primers designed according to ankyrin nucleic acid sequences of *D. immitis*, derived as described in Example 1A, and *O. volvulus*, derived from the nucleotide sequence reported in Erttmann, et al., 1996a, ibid. The primers included forward primer OVANKY-1+, having the nucleotide sequence 5' GCACAACCAG TTCCGCAAGA AA 3', denoted herein as SEQ ID NO:44 and reverse primer DIANKY-1–, having the nucleotide sequence 5' GGTTAT-TGGA AGAAGATTTC C 3', denoted herein as SEQ ID NO:45. DIANKY-1– was designed to hybridize to nucleotides 22–42 of SEQ ID NO:1, i.e., about 22–42 nucleotides downstream of the 5'-end of nDiAnk$_{937}$. Amplification was accomplished using the "touchdown" PCR protocol as described in Example 1A. A PCR product of about 600 bp was observed upon agarose gel electrophoresis of the PCR reaction, which is denoted herein as nDiAnk$_{600}$. The PCR product was gel purified and subcloned into the pCRII vector as described in Example 1A. The nucleotide sequence of nDiAnk$_{600}$ was determined, and is presented herein as SEQ ID NO:11 (the coding strand) and SEQ ID NO:13 (the complementary strand). The 42 nucleotides on the 3' end of nDiAnk$_{600}$ lined up with 100% identity to the 42 nucleotides on the 5' end of nDiANK$_{937}$ (disclosed in Example 1A).

Translation of SEQ ID NO:11 yields a protein of about 200 amino acids, denoted herein as PDiAnk$_{200}$, the amino acid sequence of which is presented in SEQ ID NO:12, assuming a first in-frame codon extending from nucleotide 1 to nucleotide 3 of SEQ ID NO:11. The 14 amino acid residues on the C-terminal end of PDiAnk$_{200}$, lined up with 100% identity to the 14 amino acid residues on the N-terminal end of PDiAnk$_{312}$ (disclosed in Example 1A). PDiAnk$_{200}$ thus represents approximately 186 amino acids of new *D. immitis* ankyrin amino acid sequence.

D. An additional *D. immitis* ankyrin nucleic acid molecule of about 1228 bp was isolated from a *D. immitis* 48-h L3 cDNA library by nested PCR, as follows.

In order to clone additional *D. immitis* ankyrin nucleic acid molecules, three degenerate forward primers were designed based on *C. elegans* UNC-44 DNA sequences reported in Otsuka, et al., ibid. These primers were paired with various *D. immitis* reverse primers in several unsuccessful attempts to isolate additional *D. immitis* ankyrin nucleic acid molecules from a *D. immitis* 48-h L3 cDNA library by standard PCR amplification. Finally, an additional *D. immitis* ankyrin nucleic acid molecule was isolated when two of the *C. elegans*-derived primers were used with two *D. immitis*-derived primers in a nested PCR. The two forward primers were: CEANKY-3+, having the nucleotide sequence 5' CAYCARGCNG CNCARCARGG NCA 3', denoted herein as SEQ ID NO:46, and CEANKY-4+, having the nucleotide sequence 5' GTNGAYGAYG TNACNGTNGA YTA 3', denoted herein as SEQ ID NO:47. A standard PCR amplification was performed using as a template a *D. immitis* 48-hour L3 cDNA library constructed as described in Example 1A, using forward primer CEANKY-4+ and reverse primer DIANKY-1–, as disclosed in Example 1C. No distinct nucleic acid molecules were observed from this PCR reaction upon gel electrophoresis, but a smear of indistinguishable PCR products was evident. A very small aliquot of this initial PCR reaction was subsequently used as a template for a second PCR, using forward primer CEANKY-3+, which was predicted to anneal internal to CEANKY-4+, and reverse primer DIANKY-2+, having the nucleotide sequence 5' GGAATTTGCG ACGACGCGGT TC 3', denoted herein as SEQ ID NO:48, which was designed to hybridize to nucleotides 76–97 of SEQ ID NO:11, i.e., about 76–97 nucleotides downstream of the 5'-end of nDiAnk$_{600}$. This second amplification produced a single predominant PCR product of about 1228 bp, as viewed by separation on an agarose gel, denoted herein as nDiAnk$_{1228}$. This PCR product was gel purified and subcloned into plasmid pCRII as described in Example 1A. The nucleotide sequence of nDiAnk$_{1228}$ was determined, and is presented herein as SEQ ID NO:14 (the coding strand) and SEQ ID NO:16 (the complementary strand). The 97 nucleotides on the 3' end of nDiAnk$_{1228}$ lined up with 100% identity to the 97 nucleotides on the 5' end of nDiANK$_{600}$ (disclosed in Example 1C).

Translation of SEQ ID NO:14 yields a protein of about 409 amino acids, denoted herein as PDiAnk$_{409}$, the amino acid sequence of which is presented in SEQ ID NO:15, assuming a first in-frame codon extending from nucleotide 1 to nucleotide 3 of SEQ ID NO:14. The coding region encoding PDiAnk$_{409}$ is presented herein as nDiAnk$_{1227}$, which has the nucleotide sequence SEQ ID NO:17 (the coding strand) and SEQ ID NO:18 (the complementary strand). The 32 amino acid residues on the C-terminal end of PDiAnk$_{409}$ lined up with 100% identity to the 32 amino acid residues on the N-terminal end of PDiAnk$_{200}$ (disclosed in Example 1 C). PDiAnk$_{409}$ thus represents about 377 amino acids of new *D. immitis* ankyrin amino acid sequence.

E. An additional ankyrin nucleic acid molecule of about 573 bp was isolated by PCR from a *D. immitis* 48-hour L3 cDNA library, as follows.

An about 573-bp *D. immitis* ankyrin nucleic acid molecule was amplified by standard PCR from a *D. immitis* 48-hour L3 cDNA library constructed as described in Example 1A using a primer designed according to ankyrin nucleic acid sequences of *D. immitis*, derived as described in Example 1D, and an M13 reverse primer. The primers included forward primer M13 reverse, having the nucleotide sequence 5' CAGGAAACAG CTATGAC 3', denoted herein as SEQ ID NO:49 and reverse primer DIANKY-3–-, having the nucleotide sequence 5' TGGAGTTTGT CCTGTCGATG TATG 3', denoted herein as SEQ ID NO:50. DIANKY-3– was designed to hybridize to nucleotides 73–96 of SEQ ID NO:14, i.e., about 73–96 nucleotides downstream of the 5'-end of nDiAnk$_{1228}$. A PCR product of about 573 bp was observed upon agarose gel electrophoresis of the PCR reaction, which is denoted herein as nDiAnk$_{573}$. The PCR product was gel purified and subcloned into the pCRII vector as described in Example 1A. The nucleotide sequence of nDiAnk$_{573}$ was determined, and is presented herein as SEQ ID NO:19 (the coding strand) and SEQ ID NO:21 (the complementary strand). The 96 nucleotides on the 3' end of nDiAnk$_{573}$ lined up with 100% identity to the 96 nucleotides on the 5' end of nDiANK$_{1228}$ (disclosed in Example 1D).

Translation of SEQ ID NO:19 yields a protein of about 191 amino acids, denoted herein as PDiAnk$_{191}$, the amino acid sequence of which is presented in SEQ ID NO:20, assuming a first in-frame codon extending from nucleotide 1 to nucleotide 3 of SEQ ID NO:19. The 32 amino acid residues on the C-terminal end of PDiAnk$_{191}$ lined up with 100% identity to the 32 amino acid residues on the N-terminal end of PDiAnk$_{409}$ (disclosed in Example 1D). PDiAnk$_{191}$ thus represents approximately 159 amino acids of new *D. immitis* ankyrin amino acid sequence.

F. An additional ankyrin nucleic acid molecule of about 911 bp was isolated from first-strand reverse transcriptase cDNA syntheses of *D. immitis* adult messenger RNA by PCR, as follows.

Attempts to isolate additional portions of a *D. immitis* ankyrin nucleic acid molecule from a cDNA library were unsuccessful. Therefore, additional portions were isolated from first-strand reverse transcriptase cDNA syntheses of *D. immitis* adult messenger RNA, by PCR amplification. A *D. immitis*-specific reverse primer was designed near the 5' terminus of nDiAnk$_{573}$ described in Example 1E above. This primer, denoted as DLANKY-4-, having the nucleotide sequence 5' GCTTTGCTTT CAGCATTCGC ATTTGCC 3', denoted herein as SEQ ID NO:51, along with degenerate forward primer CEANKY-4+, described in Example 1D, were used in PCR amplifications of first-strand reverse transcriptase cDNA syntheses of *D. immitis* adult messenger RNA, prepared by standard methods. DLANKY-4- was designed to hybridize to nucleotides 138–164 of SEQ ID NO:19, i.e., about 138–164 nucleotides downstream of the 5'-end of nDiAnk$_{573}$. A PCR product of about 911 bp, visualized by agarose gel electrophoresis, was obtained by PCR amplification using as a template first strand cDNA syntheses of either adult female or adult male *D. immitis* messenger RNA using these primers. It should be noted that PCR amplifications performed with three other degenerate forward primers, designed from the UNC-44 nucleotide sequence of Otsuka, et al., ibid., in conjunction with *D. immitis* reverse primers, did not result in the successful amplification of *D. immitis* ankyrin nucleic acid molecules. The 911-bp PCR products were excised from the agarose gel on which they were separated, and bathed in a small volume of Tris-EDTA buffer. Ten microliter aliquots of these excised products in TE were used as template for reamplification PCRs, using the same primers, to verify the product. More intense bands of exactly the same size, denoted herein as nDiAnk$_{911}$, were produced by these second round PCRs, as seen by separation on an agarose gel.

Nucleic acid molecules from both the first and second PCR reactions were gel purified and subcloned into plasmid pCRII as described in Example 1A. The subcloned DNA products were submitted for automated sequencing. Sequence analysis revealed that the inserts of all PCR products were identical, and are denoted herein as SEQ ID NO:22 (the coding strand) and SEQ ID NO:24 (the complementary strand). The 164 nucleotides on the 3' end of nDiAnk$_{911}$ lined up with 100% identity to the 164 nucleotides on the 5' end of nDiANK$_{573}$ (disclosed in Example 1E).

Translation of SEQ ID NO:22 yields a protein of about 303 amino acids, denoted herein as PDiAnk$_{303}$, the amino acid sequence of which is presented in SEQ ID NO:23, assuming a first in-frame codon extending from nucleotide 1 to nucleotide 3 of SEQ ID NO:22. The coding region encoding PDiAnk$_{303}$ is presented herein as nDiAnk$_{909}$, which has the nucleotide sequence SEQ ID NO:25 (the coding strand) and SEQ ID NO:26 (the complementary strand). The 54 amino acid residues on the C-terminal end of PDiAnk$_{303}$ lined up with 100% identity to the 54 amino acid residues on the N-terminal end of the PDiAnk$_{191}$ (disclosed in Example 1E). PDiAnk$_{303}$ thus represents approximately 249 amino acids of new *D. immitis* ankyrin amino acid sequence.

G. An additional ankyrin nucleic acid molecule of about 1096 bp, containing sequences representing the authentic 5' end of a *D. immitis* ankyrin messenger RNA, was isolated from first-strand reverse transcriptase cDNA syntheses of *D. immitis* adult messenger RNA by PCR, as follows.

A *D. immitis*-specific reverse primer was designed near the 5' terminus of nDiAnk$_{911}$ described in Example 1F above. This primer, denoted DIANKY-7-, having the nucleotide sequence 5' GTGAGATAGT CAACAGTAAC ATCATCC 3', denoted herein as SEQ ID NO:53, was designed to hybridize to nucleotides 3–29 of SEQ ID NO:22, i.e., about 3–29 nucleotides downstream of the 5'-end of nDiAnk$_{911}$. DLANKY-7- was used along with a sense primer designed according to the nematode splice leader (SL) in PCR amplifications of first-strand reverse transcriptase cDNA syntheses of *D. immitis* adult messenger RNA, prepared by standard methods. Most, but not all nematode messenger RNAs have the SL at their 5' ends, and the presence of the 5' SL sequence is indicative of an apparently full length cDNA molecule. See, for example Blaxter and Liu, 1996, *Int. J. Parasitol.* 26, 1025–1033, which is incorporated herein by reference. The splice leader primer, denoted DiSL, has the nucleotide sequence 5' GGTTTAATTA CCCAAGTTTG AG 3', denoted herein as SEQ ID NO:52. Using these primers, PCR products of about 1096 bp were obtained using adult male and adult female mRNAs as templates. These nucleic acid molecules were gel-purified using the QIAquick™ kit as per manufacturer's instructions. The yield of these purifications was low, so one microliter each of the purified DNA products were used as templates in reamplification PCRs using the same primers. More intense products of precisely the same size, collectively denoted herein as nDiANK$_{1096}$, were obtained from the reamplification PCRs, and were subcloned into plasmid pCRII as described in Example 1A. One of the subcloned nucleic acid molecules was submitted for automated nucleic acid sequencing. Sequence analysis suggested that nDiAnk$_{1096}$, the sequence of which is represented herein as SEQ ID NO:27 (the coding strand) and SEQ ID NO:29 (the complementary strand), represented the authentic 5' end of a *D. immitis* ankyrin messenger RNA. The 5' end of nDiAnk$_{1096}$ included the spliced leader sequence, 28 nucleotides of 5' untranslated sequence, and the starting methionine of the coding sequence. The 29 nucleotides on the 3' end of nDiANK$_{1096}$ lined up with 100% identity to the 29 nucleotides on the 5' end of nDiANK$_{911}$ (disclosed in Example 1F).

Translation of SEQ ID NO:27 yields a protein of about 348 amino acids, denoted herein as PDiAnk$_{348}$, the amino acid sequence of which is presented in SEQ ID NO:28, assuming a start codon extending from nucleotide 51 to nucleotide 53 of SEQ ID NO:27. The nucleic acid molecule representing the coding region encoding PDiAnk$_{348}$, denoted herein as nDiAnk$_{1044}$, is presented herein as SEQ ID NO:30 (the coding strand) and SEQ ID NO:31 (the complementary strand). The about 9 amino acid residues on the C-terminal end of PDiAnk$_{348}$ lined up with about 100% identity to the about 9 amino acid residues on the N-terminal end of the PDiAnk$_{303}$ (disclosed in Example 1F). PDiAnk$_{348}$ thus represents approximately 339 amino acids of new *D. immitis* ankyrin amino acid sequence.

H. A composite nucleotide sequence of a full-length *D. immitis* ankyrin gene was compiled as follows.

A *D. immitis* ankyrin nucleic acid molecule of 5503 bp, denoted herein as nDiAnk$_{5503}$, including an apparently full-length coding region, was compiled by aligning the overlapping nucleic acid sequences SEQ ID NO:1, SEQ ID NO:6, SEQ ID NO:11, SEQ ID NO:14, SEQ ID NO:19, SEQ ID NO:22, and SEQ ID NO:27. The composite full-length nucleic acid molecule has a nucleic acid sequence presented herein as SEQ ID NO:32 (the coding strand) and SEQ ID NO:34 (the complementary strand). SEQ ID NO:32 contains the 5' nematode spliced leader sequence extending from about nucleotide 1 through about nucleotide 27, and a 28 bp 5' non-coding region extending from about nucleotide 28 through about nucleotide 50.

Translation of SEQ ID NO:32 yields a full-length protein of about 1745 amino acids, denoted PDiAnk$_{1745}$, assuming a start codon extending from nucleotide 51 through nucleotide 53 of SEQ ID NO:32, and a stop codon extending from nucleotide 5286 through nucleotide 5285 of SEQ ID NO:32. The resulting amino acid sequence is presented as SEQ ID NO:33. The coding region encoding PDiAnk$_{1745}$ not including the termination codon is denoted herein as nDiANK$_{5235}$ and has the nucleotide sequence SEQ ID NO:35 (the coding strand) and SEQ ID NO:36 (the complementary strand). SEQ ID NO:35 is predicted to encode a protein with a molecular mass of about 191.7 kD and with a predicted pI of about 5.76, as calculated by the DNAsis program.

A homology search of a non-redundant protein database was performed with SEQ ID NO:33, using the blastp program available through the BLAST™ network of the National Center for Biotechnology Information (NCBI) (National Library of Medicine, National Institutes of Health, Baltimore, Md.), available on the World Wide Web. This database includes SwissProt+PIR+SPupdate+GenPept+GPUpdate+PDB databases. The highest scoring match of the homology search at the amino acid level was GenBank™ accession number gi|1208874, a *C. elegans* ankyrin-like protein, to which SEQ ID NO:33 showed about 69% identity, spanning from about amino acid 1 through about amino acid 1745 of SEQ ID NO:33. The second highest scoring match of the homology search at the amino acid level was GenBank™ accession number gi|406288, a human brain ankyrin protein (variant I, Ankyrin$_B$), to which SEQ ID NO:33 showed about 51% identity, spanning from about amino acid 1 through about amino acid 1745. SEQ ID NO:33 was also compared to the sequence of the *O. volvulus* E1 protein as disclosed by Erttmann, et al., 1996a, ibid. A region of SEQ ID NO:33 spanning from about amino acid 1282 to about amino acid 1745 showed about 78% identity to the full-length *O. volvulus* E1 protein of 467 amino acids. At the nucleotide level, the coding region represented in SEQ ID NO:35 was compared to the cDNA encoding the *O. volvulus* E1 protein. A region of SEQ ID NO:35 spanning from about nucleotide 3423 to about nucleotide 5574 showed about 88% nucleic acid identity to the cDNA containing a full-length coding region of 1401 nucleotides encoding the *O. volvulus* E1 protein.

Example 2

This Example discloses an analysis of the predicted functional domains of a full-length *D. immitis* ankyrin protein.

Based on comparisons with mammalian ankyrin proteins, as well as the protein encoded by the *C. elegans* UNC-44 gene, the putative positions of the three functional domains of ankyrin proteins were identified in SEQ ID NO:33, the amino acid sequence of an apparent full-length *D. immitis* ankyrin protein, namely PDiAnk$_{1745}$, isolated as disclosed in Example 1. While not being bound by theory, an N-terminal membrane protein-binding domain is predicted to extend from about amino acid 1 to about amino acid 880 of SEQ ID NO:33, a spectrin-binding domain is predicted to extend from about amino acid 881 to about amino acid 1398 of SEQ ID NO:33, and a regulatory domain is predicted to extend from about amino acid 1399 to about amino acid 1745 of SEQ ID NO:33.

The N-terminal membrane protein-binding domain of PDiAnk$_{1745}$ is further characterized by the presence of 24 tandemly arrayed repeats, most of which comprise about 33 amino acid residues. These repeat regions are listed in Table 1, designated by numbers, along with a general consensus sequence pattern. The terms "start" and "end" in Table 1 refer to the sequential amino acid numbers in SEQ ID NO:33 corresponding to the first and last amino acid, respectively, of each repeat listed in Table 1. The first and the twenty-fourth repeats are not as well conserved as the other repeats. To the inventor's knowledge, this is the first disclosure of ankyrin-like repeats in a parasitic nematode.

TABLE 1

Ankyrin-like repeats of PDiAnk$_{1745}$

| No. | START | | END |
|---|---|---|---|
| 01 | 36 | ESSASFLRAA RAGNLDRVLE LLRSGTDINT CNA | 68 |
| 02 | 69 | NGLNALHLAS KEGHHEVVRE LLKRKADVDA ATR | 101 |
| 03 | 102 | KGNTALHIAS LAGQELIVTV LVENGANVNV QSL | 134 |
| 04 | 135 | NGFTPLYMAA QENHESVVRY LLAHNANQAL STE | 167 |
| 05 | 168 | DGFTPLAVAL QQGHDRVVAV LLENDTRGK~ ~~~ | 196 |
| 06 | 197 | VRLPALHIAA KKDDTKAATL LLQNEHNSDV TSK | 229 |
| 07 | 230 | SGFTPLHIAA HYGNENVAQL LLEKGANVNY QAR | 262 |
| 08 | 263 | HNISPLHVAT KWGRTNMVSL LLAHGAVIDC RTR | 295 |
| 09 | 296 | DLLTPLHCAS RSGHDQVVDL LLEKGAPISA KTK | 328 |
| 10 | 329 | NGLAPLHMAA Q~~~~~~~~ ~~~~~~~VDD VTV | 345 |
| 11 | 346 | DYLTPLHVAA HCGHVRVAKL LLDRNADPNA RAL | 378 |
| 12 | 379 | NGFTPLHIAC KKNRIKIVEL LLKYHAAIEA TTE | 411 |
| 13 | 412 | SGLSPLHVAA FMGAINIVIY LLQQGANADV ATV | 444 |
| 14 | 445 | RGETPLHLAA RANQTDIVRV LVRNGAQVDA AAR | 477 |
| 15 | 478 | ELQTPLHIAS RLGNTDIVIL LLQANASPNA ATR | 510 |

TABLE 1-continued

Ankyrin-like repeats of PDiAnk$_{1745}$

| No. | START | | END |
|---|---|---|---|
| 16 | 511 | DLYTPLHIAA KEGQEEVAAI LMDHGTDKTL LTK | 543 |
| 17 | 544 | KGFTPLHLAA KYGNLPVAKS LLERGTPVDI EGK | 576 |
| 18 | 577 | NQVTPLHVAA HYNNDKVALL LLENGASAHA AAK | 609 |
| 19 | 610 | NGYTPLHIAA KKNQMDIAST LLHYKANANA ESK | 642 |
| 20 | 643 | AGFTPLHLAA QEGHREMAAL LIENGAKVGA QAR | 675 |
| 21 | 676 | NGLTPMHLCA QEDRVSVAEE LVKENAAIDP KTK | 708 |
| 22 | 709 | AGYTPLHVAC HFGQINMVRF LIEHGARVSV ITR | 741 |
| 23 | 742 | ASYTPLHQAA QQGHNSVVRY LLEHGASPNV HTS | 774 |
| 24 | 775 | TGQTPLSIAE RLGYVSVVEA LKTITETTVI TET | 807 |

Consensus -G-TPLH-AA --GH---V/A-- LL--GA--N/D- ---

Repeat regions 01 through 24 as disclosed in Table 1 are presented herein as SEQ ID NO:61 through SEQ ID NO:84, respectively. The consensus sequence is presented herein as SEQ ID NO:85. A novel feature of the membrane-binding domain of PDiAnk$_{1745}$ is repeat No. 10 (SEQ ID NO:70), which apparently comprises only 17 amino acids. While not being bound by theory, this shortened repeat is unique among ankyrin proteins.

Example 3

This Example demonstrates the use of D. immitis nucleic acid molecules of the present invention to obtain, by PCR amplification, an ankyrin nucleic acid molecule from a related filariid nematode, Brugia malayi.

A B. malayi ankyrin nucleic acid molecule was PCR amplified from a first-strand cDNA synthesis of messenger RNA prepared from B. malayi adult female worms, as follows. The PCR primers included forward primer CEANKY 4+, as disclosed in Example 1D, and reverse primer DIANKY 4–, as disclosed in Example 1F. An about 908-bp nucleic acid molecule was amplified in a PCR amplification of a first-strand reverse transcriptase cDNA synthesis of B. malayi adult female messenger RNA, prepared by standard methods, and is denoted herein as nBmAnk$_{908}$.

Nucleic acid molecule nBmAnk$_{908}$ was gel purified and subcloned into plasmid pCRII, and sequenced as described in Example 1A. The sequence is presented as SEQ ID NO:37 (the coding strand) and SEQ ID NO:39 (the complementary strand). Translation of SEQ ID NO:37 yields a non-full-length protein of about 302 amino acids, denoted herein as PBmAnk$_{302}$, assuming a first in-frame codon extending from nucleotide 1 through nucleotide 3 of SEQ ID NO:37. The resulting amino acid sequence is presented as SEQ ID NO:38. The coding region encoding PBmAnk$_{302}$ is denoted herein as nBmANK$_{906}$, and has the nucleotide sequence SEQ ID NO:40 (the coding strand) and SEQ ID NO:41 (the complementary strand).

A homology search of a non-redundant protein database was performed on SEQ ID NO:38 using the BLAST network. The homology spans from about amino acid 1 through amino acid 302 of SEQ ID NO:38. The highest scoring match of the homology search at the amino acid level was GenBank accession number A57282, a C. elegans ankyrin-like protein, which was about 86% identical to SEQ ID NO:38 through a region extending from about amino acid 353 through about amino acid 654 of A57282. The B. malayi ankyrin nucleic acid molecule and protein sequences represented by SEQ ID NO:37 and SEQ ID NO:38, respectively, had no similarity to the O. volvulus E1 nucleic acid molecule and protein disclosed by Erttmann, et al., 1996a, ibid.

The amino acid sequence of SEQ ID NO:38 was also compared to PDiAnk$_{1747}$ (i.e., SEQ ID NO:33 of the present invention). PBmAnk$_{302}$ had 95% identity to the region of SEQ ID NO:33 spanning from about amino acid 341 through about amino acid 642.

Example 4

The following experiment was performed in order to confirm the origin of the ankyrin gene in the D. immitis genome, and to identify genomic restriction fragments associating with a partial ankyrin cDNA clone. The experiment also evaluates if multiple copies of the ankyrin gene are present in the D. immitis genome. Four enzymes were each used individually to digest about 10 micrograms of D. immitis genomic DNA each. A Southern blot containing genomic DNA samples restricted with Sau3A-I, EcoRI, HindIII, and XhoI, respectively, was hybridized under stringent conditions using nDiAnk$_{937}$, isolated as disclosed in Example 1A, labeled with the radioactive isotope $^{32}$P. The nDiAnk$_{937}$ probe hybridized to three bands of 460 bp, 550 bp, and 770 bp in the genomic restriction digestion using Sau3A-I. A single band of 5490 bp hybridized in the EcoRI digestion. Two bands of 930 bp and 3330 bp hybridized in the HindIII digestion. Two bands also hybridized in the XhoI digestion (which of the four enzymes digested the genomic DNA most incompletely), one of 3330 bp and one of 43,200 bp, the latter appearing in a band representing undigested DNA. This experiment confirmed the D. immitis origin of ankyrin nucleic acid molecules of the present invention. While not being bound by theory, since no EcoRI sites are present within the full-length coding region of nDiAnkl$_{1745}$, the single EcoRI genomic fragment hybridizing with the nDiAnk$_{937}$ probe suggests that at least the portion of nDi-Ank$_{1745}$ included in nDiAnk$_{937}$ is present as a single copy in the D. immitis genome.

Example 5

This Example discloses the production of a recombinant cell of the present invention.

Recombinant molecule pTrc-nDiAnk$_{1866}$, containing a D. immitis ankyrin nucleic acid molecule operatively linked to trc transcription control sequences and to a fusion sequence encoding the T7 tag and a poly-histidine segment, was produced in the following manner. An about 1866-nucleotide DNA fragment containing nucleotides spanning from about 3423 through about 5288 of SEQ ID NO:32, denoted herein as nDiAnkl$_{1866}$, was PCR-amplified by "touchdown" PCR from D. immitis L3 and L4 cDNA libraries produced by the methods described in Example 1A, using sense primer OVANKY 1+ (SEQ ID NO:44, as described in Example 1C), and DIANKY−, having the nucleotide sequence 5' CCGGAATTCT TATTCATGAA CGCTTTGCCC TTT 3', denoted herein as SEQ ID NO:55, EcoRI site in bold. DIANKY− was designed to anneal to a region of SEQ ID NO:32 extending from nucleotide 5365 through nucleotide 5288. This PCR product was gel-purified using the QIAquick™ kit as per manufacturer's instructions. The yield of this purification was low, so one microliter of the purified DNA product was used as template in a reamplification PCR (standard PCR) using forward primer DIANKY 3+, having the nucleotide sequence 5' CGCG-GATCCG GCACAACCAG TTCCGCAAGA A 3', denoted herein as SEQ ID NO:54, BamHI site in bold, and antisense primer DIANKY−, as described above. DIANKY 3+ was designed to anneal to the PCR product generated above, but shares 17/20 bp in common with nucleotides 3423 through 3443 of SEQ ID NO:32. A more intense product of approximately the same size, denoted herein as nDiAnk$_{1866}$, was obtained from the reamplification PCR. Recombinant molecule pTrc-nDiAnk$_{1866}$ was produced by digesting the PCR-amplified DNA fragment with BamHI and EcoRI restriction endonucleases, gel purifying the resulting fragment and directionally subcloning it into expression vector pTrcHisB (available from Invitrogen) that had been cleaved with BamHI and EcoRI and gel purified.

Recombinant molecule pTrc-nDiAnk$_{1866}$ was transformed into E. coli to form recombinant cell E. coli:pTrc-nDiAnk$_{1866}$ using standard techniques.

Example 6

This Example discloses the production of additional recombinant cells of the present invention.

A. Recombinant molecule pTrc-nDiAnk$_{2361}$, containing a D. immitis ankyrin nucleic acid molecule encoding the predicted membrane protein-binding domain (disclosed in Example 2), operatively linked to trc transcription control sequences and to a fusion sequence encoding the T7 tag and a poly-histidine segment, is produced in the following manner. An about 2361-nucleotide DNA fragment spanning from about nucleotide 51 through about nucleotide 2411 of SEQ ID NO:32, denoted herein as nDiAnk$_{2361}$, was RT-PCR-amplified from four different D. immitis messenger RNA templates. The templates were as follows: 48-hour L3 (i.e., third-stage larvae harvested at 48 hours), 6-day L4 (i.e., fourth stage larvae harvested at 6 days), adult female, and adult male D. immitis mRNAs. The PCR primers included DIANKY REP+, having the nucleotide sequence 5' CGCG-GATCCG ATGAGTAATC CTATAGTCGA GGG 3', denoted herein as SEQ ID NO:56, BamHI site in bold, and reverse primer DIANKY REP−, having the nucleotide sequence 5' CCGGAATTCC GGTTACCCTA GACGT-TCAGC AATCG 3', denoted herein as SEQ ID NO:57, EcoRI site in bold. The amplification produced a product of the predicted size from each of the four mRNA templates. This result indicates that the portion of the D. immitis ankyrin gene encoding the putative membrane protein-binding domain is expressed in at least two larval stages and in male and female adult parasites. Recombinant molecule pTrc-nDiAnk$_{2361}$ is produced by digesting any one of the PCR-amplified DNA fragments with BamHI and EcoRI restriction endonucleases, gel purifying the resulting fragment and directionally subcloning it into expression vector pTrcHisB (available from Invitrogen) which is cleaved with BamHI and EcoRI and gel purified.

B. Recombinant molecule pTrc-nDiAnk$_{1266}$, containing a D. immitis ankyrin nucleic acid molecule encoding the predicted spectrin-binding domain (disclosed in Example 2), operatively linked to trc transcription control sequences and to a fusion sequence encoding the T7 tag and a poly-histidine segment, is produced in the following manner. An about 1266-nucleotide DNA fragment spanning from about nucleotide 2850 through about nucleotide 4115 of SEQ ID NO:32, denoted herein as nDiAnk$_{1266}$, was RT-PCR-amplified from the four different D. immitis messenger RNA templates described in Example 6A above. The PCR primers included DIANKY SPECT B+, having the nucleotide sequence 5' CCGGGATCCG CGCGCACGTG GAGGAG-CAAT GCGT 3', denoted herein as SEQ ID NO:58, BamHI site in bold, and reverse primer DIANKY SPECT B−, having the nucleotide sequence 5' CGCGAATTCC GGT-TATTCGT TGTCCGTGTG AGTGCG 3', denoted herein as SEQ ID NO:59, EcoRI site in bold. The amplification produced a product of the predicted size from each of the four mRNA templates. This result indicates that the portion of the D. immitis ankyrin gene encoding the putative spectrin-binding domain is expressed in at least two larval stages and in male and female adult parasites. Recombinant molecule pTrc-nDiAnk$_{1266}$ is produced by digesting any one of the PCR-amplified DNA fragments with BamHI and EcoRI restriction endonucleases, gel purifying the resulting fragment and directionally subcloning it into expression vector pTrcHisB (available from Invitrogen) which is cleaved with BamHI and EcoRI and gel purified.

C. Recombinant molecule pTrc-nDiAnk$_{864}$, containing a D. immitis ankyrin nucleic acid molecule encoding the predicted regulatory domain (disclosed in Example 2), operatively linked to trc transcription control sequences and to a fusion sequence encoding the T7 tag and a poly-histidine segment, is produced in the following manner. An about 864-nucleotide DNA fragment spanning from about nucleotide 4425 through about nucleotide 5288 of SEQ ID NO:32, denoted herein as nDiAnk$_{864}$, was RT-PCR-amplified from the four different D. immitis messenger RNA templates described in Example 6A above. The PCR primers included DIANKY REG+, having the nucleotide sequence 5' CGCGGATCCG CGCCAACTAG TTGGTCTTGA AGCAGTC 3', denoted herein as SEQ ID NO:60, BamHI site in bold, and reverse primer DIANKY−, having the nucleotide sequence 5' CCGGAATTCT TATTCATGAA CGCTTTGCCC TTT 3', denoted herein as SEQ ID NO:55, EcoRI site in bold. The amplification produced a product of the predicted size from each of the four mRNA templates. This result indicates that the portion of the D. immitis ankyrin gene encoding the putative regulatory domain is expressed in at least two larval stages and in male and female adult parasites. Recombinant molecule pTrc-nDiAnk$_{864}$ is produced by digesting the PCR-amplified DNA fragment with BamHI and EcoRI restriction endonucleases, gel purifying the resulting fragment and directionally subcloning it into expression vector pTrcHisB (available from Invitrogen) which is cleaved with BamHI and EcoRI and gel purified.

Recombinant molecules pTrc-nDiAnk$_{2361}$, pTrc-nDiAnk$_{1266}$, and pTrc-nDiAnk$_{864}$ are transformed into E. coli to form recombinant cells E. coli:pTrc-nDiAnk$_{2361}$, E. coli:pTrc-nDiAnk$_{1266}$, and E. coli:pTrc-nDiAnk$_{864}$ using standard techniques.

Example 7

This example demonstrates the production of D. immitis ankyrin proteins of the present invention in prokaryotic cells.

Recombinant cell E. coli:pTrc-nDiAnk$_{1866}$, produced as described in Example 5, was cultured in shake-flasks containing an enriched bacterial growth medium containing 0.1 mg/ml ampicillin at about 37° C. When the cells reached an $OD_{600}$ of about 0.5, expression of D. immitis nucleic acid molecule $nDiAnk_{1866}$ was induced by addition of about 0.5 mM IPTG, and the cells were cultured for about 3 hr at about 37° C. Protein production was monitored by SDS-polyacrylamide gel electrophoresis (SDS-PAGE) of recombinant cell lysates, followed by Coomassie blue staining, using standard techniques. Recombinant cell E. coli:pTrc-$nDiAnk_{1866}$ produced a fusion protein, denoted herein as PHIS-$PDiANK_{622}$, that migrated with an apparent molecular weight of about 98 kD, although the predicted molecular weight is only about 74 kD. While not being bound by theory, the difference between the observed and predicted molecular weights may be attributed to the known acidity of the regulatory domains of ankyrin proteins, which is known by those skilled in the art to reduce the binding of SDS to the protein, thereby resulting in an aberrant migration in SDS-PAGE.

Immunoblot analysis of recombinant cell E. coli:pTrc-$nDiAnk_{1866}$ lysates indicated that the about 98-kD protein was able to bind to a T7 tag monoclonal antibody (available from Novagen, Inc., Madison, Wis.) directed against the fusion portion of the recombinant PHIS-$PDiANK_{622}$ fusion protein.

Recombinant cells E. coli:pTrc-$nDiAnk_{2361}$, E. coli:pTrc-$nDiAnk_{1266}$, and E. coli:pTrc-$nDiAnk_{864}$, produced as described in Example 6, are cultured separately in shake-flasks containing an enriched bacterial growth medium containing 0.1 mg/ml ampicillin at about 37° C. When the cells reach an $OD_{600}$ of about 0.5, expression of D. immitis nucleic acid molecules $nDiAnk_{2361}$, $nDiAnk_{1266}$, and $nDiAnk_{864}$, respectively, is induced by addition of about 0.5 mM IPTG, and the cells are cultured for about 3 hr at about 37° C. Protein production is monitored by SDS-polyacrylamide gel electrophoresis (SDS-PAGE) of recombinant cell lysates, followed by Coomassie blue staining, using standard techniques. Recombinant cells E. coli:pTrc-$nDiAnk_{2361}$, E. coli:pTrc-$nDiAnk_{1266}$, and E. coli:pTrc-$nDiAnk_{864}$, are expected to produce a fusion proteins, denoted herein as PHIS-$PDiANK_{787}$, PHIS-$PDiANK_{433}$, and PHIS-$PDiANK_{288}$, respectively.

SEQUENCE LISTING

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:85 submitted herewith are the same.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated ankyrin protein, wherein said protein is encoded by a Dirofilaria or Brugia nucleic acid molecule selected from the group consisting of: a nucleic acid molecule comprising a nucleic acid sequence selected from the group consisting of SEQ ID NO:1, SEQ ID NO:4, SEQ ID NO:6, SEQ ID NO:9, SEQ ID NO:11, SEQ ID NO:14, SEQ ID NO:17, SEQ ID NO:19, SEQ ID NO:22, SEQ ID NO:25, SEQ ID NO:27, SEQ ID NO:30, SEQ ID NO:32, SEQ ID NO:35, SEQ ID NO:37 and SEQ ID NO:40; and an allelic variant of a nucleic acid molecule comprising a nucleic acid sequence selected from the group consisting of SEQ ID NO:1, SEQ ID NO:4, SEQ ID NO:6, SEQ ID NO:9, SEQ ID NO:11, SEQ ID NO:14, SEQ ID NO:17, SEQ ID NO:19, SEQ ID NO:22, SEQ ID NO:25, SEQ ID NO:27, SEQ ID NO:30, SEQ ID NO:32, SEQ ID NO:35, SEQ ID NO:37 and SEQ ID NO:40.

2. The ankyrin protein of claim 1, wherein said Dirofilaria ankyrin protein is a *Dirofilaria immitis* ankyrin protein, and wherein said Brugia ankyrin protein a *Brugia malayi* ankyrin protein.

3. The ankyrin protein of claim 1, wherein said protein, when administered to an animal, elicits an immune response against an ankyrin protein selected from the group consisting of a Dirofilaria ankyrin protein and a Brugia ankyrin protein.

4. The ankyrin protein of claim 1, wherein said protein is encoded by a nucleic acid molecule selected from the group consisting of: a nucleic acid molecule selected from the group consisting of $nDiAnk_{937}$, $nDiAnk_{936}$, $nDiAnk_{1029}$, $nDiAnk_{810}$, $nDiAnk_{600}$, $nDiAnk_{1228}$, $nDiAnk_{1227}$, $nDiAnk_{573}$, $nDiAnk_{911}$, $nDiAnk_{909}$, $nDiAnk_{1096}$, $nDiAnk_{1044}$, $nDiAnk_{5503}$, $nDiAnk_{5235}$, $nBmAnk_{908}$, and $nBmAnk_{906}$; and an allelic variant of a nucleic acid molecule selected from the group consisting of $nDiAnk_{937}$, $nDiAnk_{936}$, $nDiAnk_{1029}$, $nDiAnk_{810}$, $nDiAnk_{600}$, $nDiAnk_{1228}$, $nDiAnk_{1227}$, $nDiAnk_{573}$, $nDiAnk_{911}$, $nDiAnk_{909}$, $nDiAnk_{1096}$, $nDiAnk_{1044}$, $nDiAnk_{5503}$, $nDiAnk_{5235}$, $nBmAnk_{908}$, and $nBmAnk_{906}$.

5. An isolated ankyrin protein, wherein said protein is selected from the group consisting of: a protein comprising an amino acid sequence selected from the group consisting of SEQ ID NO:2, SEQ ID NO:7, SEQ ID NO:12, SEQ ID NO:15, SEQ ID NO:20, SEQ ID NO:23, SEQ ID NO:28, SEQ ID NO:33 and SEQ ID NO:38; and a protein comprising an amino acid sequence encoded by an allelic variant of a nucleic acid molecule encoding a protein having an amino acid sequence selected from the group consisting of SEQ ID NO:2, SEQ ID NO:7, SEQ ID NO:12, SEQ ID NO:15, SEQ ID NO:20, SEQ ID NO:23, SEQ ID NO:28, SEQ ID NO:33 and SEQ ID NO:38.

6. The ankyrin protein of claim 5, wherein said Dirofilaria ankyrin protein is a *Dirofilaria immitis* ankyrin protein, and wherein said Brugia ankyrin protein is a *Brugia malayi* ankyrin protein.

7. The ankyrin protein of claim 5, wherein said protein, when administered to an animal, elicits an immune response against an ankyrin protein selected from the group consisting of Dirofilaria ankyrin protein and a Brugia ankyrin protein.

8. An isolated ankyrin protein that is at least 75% identical to $PDiAnk_{1745}$ (SEQ ID NO:33) and has the ability to bind to an antibody against $PDiAnk_{1745}$.

9. An isolated ankyrin protein that is at least 90% identical to $PBmAnk_{302}$ (SEQ ID NO:38) and has the ability to bind to an antibody against $PbmAnk_{302}$.

10. An isolated antibody that selectively binds to an ankyrin protein as set forth in claim 1.

11. An isolated antibody that selectively binds to an ankyrin protein as set forth in claim 5.

12. A therapeutic composition to protect an animal from disease caused by a parasitic helminth, said therapeutic composition comprising the ankyrin protein of claim 1 or claim 5, or the antibody of claim 10 or claim 11.

13. The composition of claim 12, wherein said composition further comprises a component selected from the group consisting of an excipient, an adjuvant, a carrier, and a mixture thereof.

14. The composition of claim 12, wherein said disease is selected from the group consisting of heartworm disease, elephantiasis, and hydrocele.

* * * * *

UNITED STATES PATENT AND TRADEMARK OFFICE
CERTIFICATE OF CORRECTION

PATENT NO : 5,824,306
DATED : October 20, 1998
INVENTOR(S) : Liang Tang; E. Scot Blehm It is certified that error appears in the above-identified patent and that said Letters Patent is hereby corrected as shown below:

Column 33, line 29, please delete "DLANKY-4-" and insert therefor "DIANKY-4-"

Column 33, line 35, please delete "DLANKY-4-" and insert therefor "DIANKY-4-"

Column 34, line 25, please delete "DLANKY-7-" and insert therefor "DIANKY-7-"

Signed and Sealed this

Eleventh Day of April, 2000

Attest:

Q. TODD DICKINSON

Attesting Officer

Director of Patents and Trademarks

SEQUENCE LISTING ( 1 ) GENERAL INFORMATION:

( i i i ) NUMBER OF SEQUENCES: 85

( 2 ) INFORMATION FOR SEQ ID NO:1:

( i ) SEQUENCE CHARACTERISTICS:
        ( A ) LENGTH: 937 nucleotides
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..936

( x i ) SEQUENCE DESCRIPTION: SEQ ID NO:1:

```
CAT  CAG  TTT  TTG  GAA  TTT  TCT  GGA  AAT  CTT  CTT  CCA  ATA  ACC         4 2
His  Gln  Phe  Leu  Glu  Phe  Ser  Gly  Asn  Leu  Leu  Pro  Ile  Thr
 1              5                        10

AAG  AGT  GGT  GAC  CAA  CTT  TCT  CTT  TAT  TTT  CTA  CCA  TTC  CAA         8 4
Lys  Ser  Gly  Asp  Gln  Leu  Ser  Leu  Tyr  Phe  Leu  Pro  Phe  Gln
 1 5                      2 0                       2 5

GAA  AAT  CGT  CTT  GCT  TTC  ATG  GTA  AAG  ATA  CGC  ACT  CAC  ACG         1 2 6
Glu  Asn  Arg  Leu  Ala  Phe  Met  Val  Lys  Ile  Arg  Thr  His  Thr
         3 0                    3 5                      4 0

GAC  AAC  GAA  ACT  GCA  GCT  GAT  GGC  CGG  ATA  GTA  TTT  ATG  AAA         1 6 8
Asp  Asn  Glu  Thr  Ala  Ala  Asp  Gly  Arg  Ile  Val  Phe  Met  Lys
                 4 5                    5 0                      5 5

GAA  CCA  AAA  TTG  AGA  GCC  GAA  AAT  TTA  CCT  CCG  CAG  ACG  CCA         2 1 0
Glu  Pro  Lys  Leu  Arg  Ala  Glu  Asn  Leu  Pro  Pro  Gln  Thr  Pro
```

```
                         60                           65                              70
GTG  TGT  ACT  CTT  GCA  ATC  ACT  CTT  CCG  GAA  TAC  ACT  GGG  CCG                252
Val  Cys  Thr  Leu  Ala  Ile  Thr  Leu  Pro  Glu  Tyr  Thr  Gly  Pro
                    75                            80

GAG  CCG  ATG  GTT  TCC  AAA  AAA  CTC  TTC  TAT  TCG  GAA  GCT  TCT                294
Glu  Pro  Met  Val  Ser  Lys  Lys  Leu  Phe  Tyr  Ser  Glu  Ala  Ser
 85                       90                            95

TTG  ACT  GAG  AAA  TAC  GTT  GGA  GCT  TTC  CAT  GAA  ACT  GCT  GAA                336
Leu  Thr  Glu  Lys  Tyr  Val  Gly  Ala  Phe  His  Glu  Thr  Ala  Glu
     100                      105                           110

CCT  GAT  AAC  TTG  CCA  CTA  GCA  CAT  GTT  GCA  CTA  TTA  ATT  GGC                378
Pro  Asp  Asn  Leu  Pro  Leu  Ala  His  Val  Ala  Leu  Leu  Ile  Gly
          115                      120                          125

GCT  GAT  TGG  CAT  CGG  TTA  GCT  CGA  GCG  CTT  GAA  GTA  CCT  GAT                420
Ala  Asp  Trp  His  Arg  Leu  Ala  Arg  Ala  Leu  Glu  Val  Pro  Asp
               130                      135                          140

ATT  GAT  ATA  CGA  CAA  GTT  CGA  CAT  CAA  CTA  GTT  GGT  CTT  GAA                462
Ile  Asp  Ile  Arg  Gln  Val  Arg  His  Gln  Leu  Val  Gly  Leu  Glu
                    145                      150

GCA  GTC  ACT  ATT  CTA  CGT  ATT  TGG  ATA  TTT  TTG  AAG  AAA  GAA                504
Ala  Val  Thr  Ile  Leu  Arg  Ile  Trp  Ile  Phe  Leu  Lys  Lys  Glu
155                      160                           165

CAA  GCT  ACG  CCC  GTT  GCT  TTG  CGA  TCA  GCA  TTG  CAG  CGA  ATA                546
Gln  Ala  Thr  Pro  Val  Ala  Leu  Arg  Ser  Ala  Leu  Gln  Arg  Ile
     170                      175                           180

GGA  CGT  GAT  GAT  GTT  GTA  CGA  GAA  ATG  GAT  CGA  GCT  GAA  AAG                588
Gly  Arg  Asp  Asp  Val  Val  Arg  Glu  Met  Asp  Arg  Ala  Glu  Lys
          185                      190                          195

CTA  GAT  GGT  TTA  GAA  GGA  ACA  CCT  GTA  TCG  CAT  ATT  TCT  GGA                630
Leu  Asp  Gly  Leu  Glu  Gly  Thr  Pro  Val  Ser  His  Ile  Ser  Gly
               200                      205                          210

CCC  TCA  ATA  ACT  CTG  TCA  TCT  ACT  TTG  CTA  GAG  GTA  GCA  GGC                672
Pro  Ser  Ile  Thr  Leu  Ser  Ser  Thr  Leu  Leu  Glu  Val  Ala  Gly
                    215                      220

GAC  AGA  CGT  CGT  CAC  GCC  GAG  GTA  ACA  ATG  GCG  CAA  CAG  CGA                714
Asp  Arg  Arg  Arg  His  Ala  Glu  Val  Thr  Met  Ala  Gln  Gln  Arg
225                      230                           235

TTG  GCA  CAA  GAA  CCG  TTT  TTT  CAG  CAA  GTA  GGG  TAT  AAT  GGG                756
Leu  Ala  Gln  Glu  Pro  Phe  Phe  Gln  Gln  Val  Gly  Tyr  Asn  Gly
     240                      245                           250

ACA  CCT  GGA  GAT  CCA  GAA  GAA  CCC  AAA  GAA  CAG  TCA  TTC  CAC                798
Thr  Pro  Gly  Asp  Pro  Glu  Glu  Pro  Lys  Glu  Gln  Ser  Phe  His
          255                      260                          265

GAA  GAG  GAA  GAG  GAA  GTT  GCA  GTT  TCA  GAA  ATT  CGA  ACA  GTT                840
Glu  Glu  Glu  Glu  Glu  Val  Ala  Val  Ser  Glu  Ile  Arg  Thr  Val
               270                      275                          280

GTG  CGC  ACT  GAA  CGA  CAT  GTG  CAT  GAT  TCG  GAA  AAT  GGT  CCT                882
Val  Arg  Thr  Glu  Arg  His  Val  His  Asp  Ser  Glu  Asn  Gly  Pro
                    285                      290

ATT  GTG  GAA  GAG  CGT  ACA  ATA  ACA  ACT  ACG  TAT  GAG  GAT  GAT                924
Ile  Val  Glu  Glu  Arg  Thr  Ile  Thr  Thr  Thr  Tyr  Glu  Asp  Asp
295                      300                           305

GTT  GCT  GTA  AAC  G                                                               937
Val  Ala  Val  Asn
          310
```

( 2 ) INFORMATION FOR SEQ ID NO:2:

( i ) SEQUENCE CHARACTERISTICS:
        ( A ) LENGTH: 312 amino acids
        ( B ) TYPE: amino acid (D) TOPOLOGY: linear (ii) MOLECULE TYPE: protein (xi) SEQUENCE DESCRIPTION: SEQ ID NO:2:

| His | Gln | Phe | Leu | Glu | Phe | Ser | Gly | Asn | Leu | Leu | Pro | Ile | Thr |
|-----|-----|-----|-----|-----|-----|-----|-----|-----|-----|-----|-----|-----|-----|
| 1   |     |     |     | 5   |     |     |     |     | 10  |     |     |     |     |
| Lys | Ser | Gly | Asp | Gln | Leu | Ser | Leu | Tyr | Phe | Leu | Pro | Phe | Gln |
| 15  |     |     |     | 20  |     |     |     |     | 25  |     |     |     |     |
| Glu | Asn | Arg | Leu | Ala | Phe | Met | Val | Lys | Ile | Arg | Thr | His | Thr |
|     |     | 30  |     |     |     | 35  |     |     |     | 40  |     |     |     |
| Asp | Asn | Glu | Thr | Ala | Ala | Asp | Gly | Arg | Ile | Val | Phe | Met | Lys |
|     |     |     | 45  |     |     |     | 50  |     |     |     |     | 55  |     |
| Glu | Pro | Lys | Leu | Arg | Ala | Glu | Asn | Leu | Pro | Pro | Gln | Thr | Pro |
|     |     |     | 60  |     |     |     | 65  |     |     |     |     |     | 70  |
| Val | Cys | Thr | Leu | Ala | Ile | Thr | Leu | Pro | Glu | Tyr | Thr | Gly | Pro |
|     |     |     |     | 75  |     |     |     |     | 80  |     |     |     |     |
| Glu | Pro | Met | Val | Ser | Lys | Lys | Leu | Phe | Tyr | Ser | Glu | Ala | Ser |
| 85  |     |     |     |     | 90  |     |     |     |     | 95  |     |     |     |
| Leu | Thr | Glu | Lys | Tyr | Val | Gly | Ala | Phe | His | Glu | Thr | Ala | Glu |
|     | 100 |     |     |     |     | 105 |     |     |     |     | 110 |     |     |
| Pro | Asp | Asn | Leu | Pro | Leu | Ala | His | Val | Ala | Leu | Leu | Ile | Gly |
|     |     | 115 |     |     |     |     | 120 |     |     |     |     | 125 |     |
| Ala | Asp | Trp | His | Arg | Leu | Ala | Arg | Ala | Leu | Glu | Val | Pro | Asp |
|     |     |     | 130 |     |     |     |     | 135 |     |     |     |     | 140 |
| Ile | Asp | Ile | Arg | Gln | Val | Arg | His | Gln | Leu | Val | Gly | Leu | Glu |
|     |     |     |     | 145 |     |     |     |     | 150 |     |     |     |     |
| Ala | Val | Thr | Ile | Leu | Arg | Ile | Trp | Ile | Phe | Leu | Lys | Lys | Glu |
| 155 |     |     |     |     | 160 |     |     |     |     | 165 |     |     |     |
| Gln | Ala | Thr | Pro | Val | Ala | Leu | Arg | Ser | Ala | Leu | Gln | Arg | Ile |
|     | 170 |     |     |     |     | 175 |     |     |     |     | 180 |     |     |
| Gly | Arg | Asp | Asp | Val | Val | Arg | Glu | Met | Asp | Arg | Ala | Glu | Lys |
|     |     |     | 185 |     |     |     |     | 190 |     |     |     |     | 195 |
| Leu | Asp | Gly | Leu | Glu | Gly | Thr | Pro | Val | Ser | His | Ile | Ser | Gly |
|     |     |     | 200 |     |     |     |     | 205 |     |     |     |     | 210 |
| Pro | Ser | Ile | Thr | Leu | Ser | Ser | Thr | Leu | Leu | Glu | Val | Ala | Gly |
|     |     |     |     | 215 |     |     |     |     | 220 |     |     |     |     |
| Asp | Arg | Arg | Arg | His | Ala | Glu | Val | Thr | Met | Ala | Gln | Gln | Arg |
| 225 |     |     |     |     | 230 |     |     |     |     | 235 |     |     |     |
| Leu | Ala | Gln | Glu | Pro | Phe | Phe | Gln | Gln | Val | Gly | Tyr | Asn | Gly |
|     | 240 |     |     |     |     | 245 |     |     |     |     | 250 |     |     |
| Thr | Pro | Gly | Asp | Pro | Glu | Glu | Pro | Lys | Glu | Gln | Ser | Phe | His |
|     |     | 255 |     |     |     |     | 260 |     |     |     |     | 265 |     |
| Glu | Glu | Glu | Glu | Glu | Val | Ala | Val | Ser | Glu | Ile | Arg | Thr | Val |
|     |     |     | 270 |     |     |     |     | 275 |     |     |     |     | 280 |
| Val | Arg | Thr | Glu | Arg | His | Val | His | Asp | Ser | Glu | Asn | Gly | Pro |
|     |     |     |     | 285 |     |     |     |     | 290 |     |     |     |     |
| Ile | Val | Glu | Glu | Arg | Thr | Ile | Thr | Thr | Thr | Tyr | Glu | Asp | Asp |
| 295 |     |     |     |     | 300 |     |     |     |     | 305 |     |     |     |
| Val | Ala | Val | Asn |     |     |     |     |     |     |     |     |     |     |
|     | 310 |     |     |     |     |     |     |     |     |     |     |     |     |

(2) INFORMATION FOR SEQ ID NO:3:

(i) SEQUENCE CHARACTERISTICS:
        (A) LENGTH: 937 nucleotides ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

| | | | | | |
|---|---|---|---|---|---|
| CGTTTACAGC | AACATCATCC | TCATACGTAG | TTGTTATTGT | ACGCTCTTCC | 50 |
| ACAATAGGAC | CATTTTCCGA | ATCATGCACA | TGTCGTTCAG | TGCGCACAAC | 100 |
| TGTTCGAATT | TCTGAAACTG | CAACTTCCTC | TTCCTCTTCG | TGGAATGACT | 150 |
| GTTCTTTGGG | TTCTTCTGGA | TCTCCAGGTG | TCCCATTATA | CCCTACTTGC | 200 |
| TGAAAAAACG | GTTCTTGTGC | CAATCGCTGT | TGCGCCATTG | TTACCTCGGC | 250 |
| GTGACGACGT | CTGTCGCCTG | CTACCTCTAG | CAAAGTAGAT | GACAGAGTTA | 300 |
| TTGAGGGTCC | AGAAATATGC | GATACAGGTG | TTCCTTCTAA | ACCATCTAGC | 350 |
| TTTTCAGCTC | GATCCATTTC | TCGTACAACA | TCATCACGTC | CTATTCGCTG | 400 |
| CAATGCTGAT | CGCAAAGCAA | CGGGCGTAGC | TTGTTCTTTC | TTCAAAAATA | 450 |
| TCCAAATACG | TAGAATAGTG | ACTGCTTCAA | GACCAACTAG | TTGATGTCGA | 500 |
| ACTTGTCGTA | TATCAATATC | AGGTACTTCA | AGCGCTCGAG | CTAACCGATG | 550 |
| CCAATCAGCG | CCAATTAATA | GTGCAACATG | TGCTAGTGGC | AAGTTATCAG | 600 |
| GTTCAGCAGT | TTCATGGAAA | GCTCCAACGT | ATTTCTCAGT | CAAAGAAGCT | 650 |
| TCCGAATAGA | AGAGTTTTTT | GGAAACCATC | GGCTCCGGCC | CAGTGTATTC | 700 |
| CGGAAGAGTG | ATTGCAAGAG | TACACACTGG | CGTCTGCGGA | GGTAAATTTT | 750 |
| CGGCTCTCAA | TTTTGGTTCT | TTCATAAATA | CTATCCGGCC | ATCAGCTGCA | 800 |
| GTTTCGTTGT | CCGTGTGAGT | GCGTATCTTT | ACCATGAAAG | CAAGACGATT | 850 |
| TTCTTGGAAT | GGTAGAAAAT | AAAGAGAAAG | TTGGTCACCA | CTCTTGGTTA | 900 |
| TTGGAAGAAG | ATTTCCAGAA | AATTCCAAAA | ACTGATG | | 937 |

( 2 ) INFORMATION FOR SEQ ID NO:4:

( i ) SEQUENCE CHARACTERISTICS:
( A ) LENGTH: 936 nucleotides
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:4:

| | | | | | |
|---|---|---|---|---|---|
| CATCAGTTTT | TGGAATTTTC | TGGAAATCTT | CTTCCAATAA | CCAAGAGTGG | 50 |
| TGACCAACTT | TCTCTTTATT | TTCTACCATT | CCAAGAAAAT | CGTCTTGCTT | 100 |
| TCATGGTAAA | GATACGCACT | CACACGGACA | ACGAAACTGC | AGCTGATGGC | 150 |
| CGGATAGTAT | TTATGAAAGA | ACCAAAATTG | AGAGCCGAAA | ATTTACCTCC | 200 |
| GCAGACGCCA | GTGTGTACTC | TTGCAATCAC | TCTTCCGGAA | TACACTGGGC | 250 |
| CGGAGCCGAT | GGTTTCCAAA | AAACTCTTCT | ATTCGGAAGC | TTCTTTGACT | 300 |
| GAGAAATACG | TTGGAGCTTT | CCATGAAACT | GCTGAACCTG | ATAACTTGCC | 350 |
| ACTAGCACAT | GTTGCACTAT | TAATTGGCGC | TGATTGGCAT | CGGTTAGCTC | 400 |
| GAGCGCTTGA | AGTACCTGAT | ATTGATATAC | GACAAGTTCG | ACATCAACTA | 450 |
| GTTGGTCTTG | AAGCAGTCAC | TATTCTACGT | ATTTGGATAT | TTTGAAGAA | 500 |
| AGAACAAGCT | ACGCCCGTTG | CTTTGCGATC | AGCATTGCAG | CGAATAGGAC | 550 |

| | | | | | |
|---|---|---|---|---|---|
| GTGATGATGT | TGTACGAGAA | ATGGATCGAG | CTGAAAAGCT | AGATGGTTTA | 600 |
| GAAGGAACAC | CTGTATCGCA | TATTTCTGGA | CCCTCAATAA | CTCTGTCATC | 650 |
| TACTTTGCTA | GAGGTAGCAG | GCGACAGACG | TCGTCACGCC | GAGGTAACAA | 700 |
| TGGCGCAACA | GCGATTGGCA | CAAGAACCGT | TTTTTCAGCA | AGTAGGGTAT | 750 |
| AATGGGACAC | CTGGAGATCC | AGAAGAACCC | AAAGAACAGT | CATTCCACGA | 800 |
| AGAGGAAGAG | GAAGTTGCAG | TTTCAGAAAT | TCGAACAGTT | GTGCGCACTG | 850 |
| AACGACATGT | GCATGATTCG | GAAAATGGTC | CTATTGTGGA | AGAGCGTACA | 900 |
| ATAACAACTA | CGTATGAGGA | TGATGTTGCT | GTAAAC | | 936 |

( 2 ) INFORMATION FOR SEQ ID NO:5:

( i ) SEQUENCE CHARACTERISTICS:
        ( A ) LENGTH: 936 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

| | | | | | |
|---|---|---|---|---|---|
| GTTTACAGCA | ACATCATCCT | CATACGTAGT | TGTTATTGTA | CGCTCTTCCA | 50 |
| CAATAGGACC | ATTTTCCGAA | TCATGCACAT | GTCGTTCAGT | GCGCACAACT | 100 |
| GTTCGAATTT | CTGAAACTGC | AACTTCCTCT | TCCTCTTCGT | GGAATGACTG | 150 |
| TTCTTTGGGT | TCTTCTGGAT | CTCCAGGTGT | CCCATTATAC | CCTACTTGCT | 200 |
| GAAAAAACGG | TTCTTGTGCC | AATCGCTGTT | GCGCCATTGT | TACCTCGGCG | 250 |
| TGACGACGTC | TGTCGCCTGC | TACCTCTAGC | AAAGTAGATG | ACAGAGTTAT | 300 |
| TGAGGGTCCA | GAAATATGCG | ATACAGGTGT | TCCTTCTAAA | CCATCTAGCT | 350 |
| TTTCAGCTCG | ATCCATTTCT | CGTACAACAT | CATCACGTCC | TATTCGCTGC | 400 |
| AATGCTGATC | GCAAAGCAAC | GGGCGTAGCT | TGTTCTTTCT | TCAAAAATAT | 450 |
| CCAAATACGT | AGAATAGTGA | CTGCTTCAAG | ACCAACTAGT | TGATGTCGAA | 500 |
| CTTGTCGTAT | ATCAATATCA | GGTACTTCAA | GCGCTCGAGC | TAACCGATGC | 550 |
| CAATCAGCGC | CAATTAATAG | TGCAACATGT | GCTAGTGGCA | AGTTATCAGG | 600 |
| TTCAGCAGTT | TCATGGAAAG | CTCCAACGTA | TTTCTCAGTC | AAAGAAGCTT | 650 |
| CCGAATAGAA | GAGTTTTTTG | GAAACCATCG | GCTCCGGCCC | AGTGTATTCC | 700 |
| GGAAGAGTGA | TTGCAAGAGT | ACACACTGGC | GTCTGCGGAG | GTAAATTTTC | 750 |
| GGCTCTCAAT | TTTGGTTCTT | TCATAAATAC | TATCCGGCCA | TCAGCTGCAG | 800 |
| TTTCGTTGTC | CGTGTGAGTG | CGTATCTTTA | CCATGAAAGC | AAGACGATTT | 850 |
| TCTTGGAATG | GTAGAAAATA | AAGAGAAAGT | TGGTCACCAC | TCTTGGTTAT | 900 |
| TGGAAGAAGA | TTTCCAGAAA | ATTCCAAAAA | CTGATG | | 936 |

( 2 ) INFORMATION FOR SEQ ID NO:6:

( i ) SEQUENCE CHARACTERISTICS:
        ( A ) LENGTH: 1029 nucleotides
        ( B ) TYPE: nucleic acid
        ( C ) STRANDEDNESS: single
        ( D ) TOPOLOGY: linear ( i i ) MOLECULE TYPE: cDNA ( i x ) FEATURE:

(A) NAME/KEY: CDS
(B) LOCATION: 2..811

(xi) SEQUENCE DESCRIPTION: SEQ ID NO:6:

| | | | | | | | | | | | | | |
|---|---|---|---|---|---|---|---|---|---|---|---|---|---|
| G | AAG | AAA | GAA | CAA | GCT | ACG | CCC | GTT | GCT | TTG | CGA | TCA | GCA | 40 |
| | Lys | Lys | Glu | Gln | Ala | Thr | Pro | Val | Ala | Leu | Arg | Ser | Ala |
| | 1 | | | | 5 | | | | | 10 | | | |
| TTG | CAG | CGA | ATA | GGA | CGT | GAT | GAT | GTT | GTA | CGA | GAA | ATG | GAT | 82 |
| Leu | Gln | Arg | Ile | Gly | Arg | Asp | Asp | Val | Val | Arg | Glu | Met | Asp |
| | 15 | | | | 20 | | | | | 25 | | | |
| CGA | GCT | GAA | AAG | CTA | GAT | GGT | TTA | GAA | GGA | ACA | CCT | GTA | TCG | 124 |
| Arg | Ala | Glu | Lys | Leu | Asp | Gly | Leu | Glu | Gly | Thr | Pro | Val | Ser |
| | 30 | | | | 35 | | | | | 40 | | | |
| CAT | ATT | TCT | GGA | CCC | TCA | ATA | ACT | CTG | TCA | TCT | ACT | TTG | CTA | 166 |
| His | Ile | Ser | Gly | Pro | Ser | Ile | Thr | Leu | Ser | Ser | Thr | Leu | Leu |
| | 45 | | | | 50 | | | | | 55 | | | |
| GAG | GTA | GCA | GGC | GAC | AGA | CGT | CGT | CAC | GCC | GAG | GTA | ACA | ATG | 208 |
| Glu | Val | Ala | Gly | Asp | Arg | Arg | Arg | His | Ala | Glu | Val | Thr | Met |
| | | | 60 | | | | 65 | | | | | | |
| GCG | CAA | CAG | CGA | TTG | GCA | CAA | GAA | CCG | TTT | TTT | CAG | CAA | GTA | 250 |
| Ala | Gln | Gln | Arg | Leu | Ala | Gln | Glu | Pro | Phe | Phe | Gln | Gln | Val |
| 70 | | | | | 75 | | | | | 80 | | | |
| GGG | TAT | AAT | GGG | ACA | CCT | GGA | GAT | CCA | GAA | GAA | CCC | AAA | GAA | 292 |
| Gly | Tyr | Asn | Gly | Thr | Pro | Gly | Asp | Pro | Glu | Glu | Pro | Lys | Glu |
| | 85 | | | | 90 | | | | | 95 | | | |
| CAG | TCA | TTC | CAC | GAA | GAG | GAA | GAG | GAA | GTT | GCA | GTT | TCA | GAA | 334 |
| Gln | Ser | Phe | His | Glu | Glu | Glu | Glu | Glu | Val | Ala | Val | Ser | Glu |
| | | 100 | | | | 105 | | | | | 110 | | |
| ATT | CGA | ACA | GTT | GTG | CGC | ACT | GAA | CGA | CAT | GTG | CAT | GAT | TCG | 376 |
| Ile | Arg | Thr | Val | Val | Arg | Thr | Glu | Arg | His | Val | His | Asp | Ser |
| | | | 115 | | | | 120 | | | | | 125 | |
| GAA | AAT | GGT | CCT | ATT | GTG | GAA | GAG | CGT | ACA | ATA | ACA | ACT | ACG | 418 |
| Glu | Asn | Gly | Pro | Ile | Val | Glu | Glu | Arg | Thr | Ile | Thr | Thr | Thr |
| | | | | 130 | | | | 135 | | | | | |
| TAT | GAG | GAT | GAT | GTT | GCT | GTA | AAC | GAA | GAA | GAA | ATT | GTT | GAC | 460 |
| Tyr | Glu | Asp | Asp | Val | Ala | Val | Asn | Glu | Glu | Glu | Ile | Val | Asp |
| 140 | | | | | 145 | | | | | 150 | | | |
| AAA | ATA | GTG | CCT | CTC | AAC | GAA | GAG | GAG | CAA | GAA | AAA | TGG | GAT | 502 |
| Lys | Ile | Val | Pro | Leu | Asn | Glu | Glu | Glu | Gln | Glu | Lys | Trp | Asp |
| | 155 | | | | 160 | | | | | 165 | | | |
| CGA | ATG | GTT | CGA | GAA | GTG | GAA | ATG | AAT | TTT | GAG | CAA | CAA | GAA | 544 |
| Arg | Met | Val | Arg | Glu | Val | Glu | Met | Asn | Phe | Glu | Gln | Gln | Glu |
| | | 170 | | | | 175 | | | | | 180 | | |
| ACA | TCA | AAA | GAA | GGA | ACG | TTT | GGT | TGT | CAG | ACA | ACA | CAT | GAG | 586 |
| Thr | Ser | Lys | Glu | Gly | Thr | Phe | Gly | Cys | Gln | Thr | Thr | His | Glu |
| | | | 185 | | | | 190 | | | | | 195 | |
| AAA | GAA | AAA | GAT | GAT | GAT | GGT | GGC | AGT | CTG | AAG | ACG | ACA | ATG | 628 |
| Lys | Glu | Lys | Asp | Asp | Asp | Gly | Gly | Ser | Leu | Lys | Thr | Thr | Met |
| | | | | 200 | | | | 205 | | | | | |
| AAA | GAT | AGT | CAC | GTA | AGG | CAG | ATT | TTC | TTC | GAT | GGA | GGT | GAG | 670 |
| Lys | Asp | Ser | His | Val | Arg | Gln | Ile | Phe | Phe | Asp | Gly | Gly | Glu |
| 210 | | | | | 215 | | | | | 220 | | | |
| ACA | TCC | GCT | AAT | GAA | ACA | GGA | TTA | AGT | AGC | GGG | GAT | GCA | GAC | 712 |
| Thr | Ser | Ala | Asn | Glu | Thr | Gly | Leu | Ser | Ser | Gly | Asp | Ala | Asp |
| | 225 | | | | 230 | | | | | 235 | | | |
| ACT | ATT | ATG | ACT | CCA | ACG | ACA | AAG | GAG | GAT | AAT | CAT | GTT | ATA | 754 |
| Thr | Ile | Met | Thr | Pro | Thr | Thr | Lys | Glu | Asp | Asn | His | Val | Ile |
| | | 240 | | | | 245 | | | | | 250 | | |
| GAC | GTA | ATG | GAG | GAA | AGG | CGA | ACT | GAT | GAA | GAG | GCC | AAA | GGG | 796 |
| Asp | Val | Met | Glu | Glu | Arg | Arg | Thr | Asp | Glu | Glu | Ala | Lys | Gly |
| | | | 255 | | | | 260 | | | | | 265 | |

```
CAA  AGC  GTT  CAT  GAA  TAA TCTGGATCCA CAAATTGATT TAAATCGCAA                        844
Gln  Ser  Val  His  Glu
                    270

TCTCGCACAT GCCTATGTTG CTAATATTTA ATGAAATTTT TCAAAGCAAT                               894

AATTTGAATG CTGTTTGGGC TTCCCATATT GTTAAAGCGT TTTCCATCGT                               944

CCATTCACTT TTTGTTTTTG CTGTAGTCTG TAACTGCTAC TCTTGATAAA                               994

TTTGCTCCAG TAAAAAAAAA AAAAAAAAA AAAAA                                              1029
```

( 2 ) INFORMATION FOR SEQ ID NO:7:

( i ) SEQUENCE CHARACTERISTICS:
        ( A ) LENGTH: 270 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Lys  Lys  Glu  Gln  Ala  Thr  Pro  Val  Ala  Leu  Arg  Ser  Ala  Leu
 1                    5                        10

Gln  Arg  Ile  Gly  Arg  Asp  Val  Val  Arg  Glu  Met  Asp  Arg
 15                   20                        25

Ala  Glu  Lys  Leu  Asp  Gly  Leu  Glu  Gly  Thr  Pro  Val  Ser  His
      30                       35                        40

Ile  Ser  Gly  Pro  Ser  Ile  Thr  Leu  Ser  Ser  Thr  Leu  Leu  Glu
           45                       50                        55

Val  Ala  Gly  Asp  Arg  Arg  Arg  His  Ala  Glu  Val  Thr  Met  Ala
                60                       65                         70

Gln  Gln  Arg  Leu  Ala  Gln  Glu  Pro  Phe  Phe  Gln  Gln  Val  Gly
                     75                       80

Tyr  Asn  Gly  Thr  Pro  Gly  Asp  Pro  Glu  Glu  Pro  Lys  Glu  Gln
 85                        90                            95

Ser  Phe  His  Glu  Glu  Glu  Glu  Val  Ala  Val  Ser  Glu  Ile
      100                      105                      110

Arg  Thr  Val  Val  Arg  Thr  Glu  Arg  His  Val  His  Asp  Ser  Glu
           115                      120                      125

Asn  Gly  Pro  Ile  Val  Glu  Glu  Arg  Thr  Ile  Thr  Thr  Thr  Tyr
                130                      135                        140

Glu  Asp  Asp  Val  Ala  Val  Asn  Glu  Glu  Glu  Ile  Val  Asp  Lys
                     145                      150

Ile  Val  Pro  Leu  Asn  Glu  Glu  Glu  Gln  Glu  Lys  Trp  Asp  Arg
155                       150                      165

Met  Val  Arg  Glu  Val  Glu  Met  Asn  Phe  Glu  Gln  Gln  Glu  Thr
      170                      175                      180

Ser  Lys  Glu  Gly  Thr  Phe  Gly  Cys  Gln  Thr  Thr  His  Glu  Lys
           185                      190                      195

Glu  Lys  Asp  Asp  Asp  Gly  Gly  Ser  Leu  Lys  Thr  Thr  Met  Lys
                200                      205                        210

Asp  Ser  His  Val  Arg  Gln  Ile  Phe  Phe  Asp  Gly  Gly  Glu  Thr
                     215                      220

Ser  Ala  Asn  Glu  Thr  Gly  Leu  Ser  Ser  Gly  Asp  Ala  Asp  Thr
225                       230                      235

Ile  Met  Thr  Pro  Thr  Thr  Lys  Glu  Asp  Asn  His  Val  Ile  Asp
      240                      245                      250

Val  Met  Glu  Glu  Arg  Arg  Thr  Asp  Glu  Glu  Ala  Lys  Gly  Gln
```

|  | 255 |  | 260 |  | 265 |  |
|---|---|---|---|---|---|---|

Ser Val His Glu
                270

( 2 ) INFORMATION FOR SEQ ID NO:8:

( i ) SEQUENCE CHARACTERISTICS:
        ( A ) LENGTH: 1029 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

| | | | | | |
|---|---|---|---|---|---|
| TTTTTTTTT | TTTTTTTTT | TTTTACTGGA | GCAAATTTAT | CAAGAGTAGC | 50 |
| AGTTACAGAC | TACAGCAAAA | ACAAAAGTG | AATGGACGAT | GGAAAACGCT | 100 |
| TTAACAATAT | GGGAAGCCCA | AACAGCATTC | AAATTATTGC | TTTGAAAAAT | 150 |
| TTCATTAAAT | ATTAGCAACA | TAGGCATGTG | CGAGATTGCG | ATTTAAATCA | 200 |
| ATTTGTGGAT | CCAGATTATT | CATGAACGCT | TTGCCCTTTG | GCCTCTTCAT | 250 |
| CAGTTCGCCT | TTCCTCCATT | ACGTCTATAA | CATGATTATC | CTCCTTTGTC | 300 |
| GTTGGAGTCA | TAATAGTGTC | TGCATCCCCG | CTACTTAATC | CTGTTTCATT | 350 |
| AGCGGATGTC | TCACCTCCAT | CGAAGAAAAT | CTGCCTTACG | TGACTATCTT | 400 |
| TCATTGTCGT | CTTCAGACTG | CCACCATCAT | CATCTTTTTC | TTTCTCATGT | 450 |
| GTTGTCTGAC | AACCAAACGT | TCCTTCTTTT | GATGTTTCTT | GTTGCTCAAA | 500 |
| ATTCATTTCC | ACTTCTCGAA | CCATTCGATC | CCATTTTTCT | TGCTCCTCTT | 550 |
| CGTTGAGAGG | CACTATTTTG | TCAACAATTT | CTTCTTCGTT | TACAGCAACA | 600 |
| TCATCCTCAT | ACGTAGTTGT | TATTGTACGC | TCTTCCACAA | TAGGACCATT | 650 |
| TTCCGAATCA | TGCACATGTC | GTTCAGTGCG | CACAACTGTT | CGAATTTCTG | 700 |
| AAACTGCAAC | TTCCTCTTCC | TCTTCGTGGA | ATGACTGTTC | TTTGGGTTCT | 750 |
| TCTGGATCTC | CAGGTGTCCC | ATTATACCCT | ACTTGCTGAA | AAAACGGTTC | 800 |
| TTGTGCCAAT | CGCTGTTGCG | CCATTGTTAC | CTCGGCGTGA | CGACGTCTGT | 850 |
| CGCCTGCTAC | CTCTAGCAAA | GTAGATGACA | GAGTTATTGA | GGGTCCAGAA | 900 |
| ATATGCGATA | CAGGTGTTCC | TTCTAAACCA | TCTAGCTTTT | CAGCTCGATC | 950 |
| CATTTCTCGT | ACAACATCAT | CACGTCCTAT | TCGCTGCAAT | GCTGATCGCA | 1000 |
| AAGCAACGGG | CGTAGCTTGT | TCTTTCTTC | | | 1029 |

( 2 ) INFORMATION FOR SEQ ID NO:9:

( i ) SEQUENCE CHARACTERISTICS:
        ( A ) LENGTH: 810 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

| | | | | | |
|---|---|---|---|---|---|
| AAGAAAGAAC | AAGCTACGCC | CGTTGCTTTG | CGATCAGCAT | TGCAGCGAAT | 50 |
| AGGACGTGAT | GATGTTGTAC | GAGAAATGGA | TCGAGCTGAA | AAGCTAGATG | 100 |
| GTTTAGAAGG | AACACCTGTA | TCGCATATTT | CTGGACCCTC | AATAACTCTG | 150 |
| TCATCTACTT | TGCTAGAGGT | AGCAGGCGAC | AGACGTCGTC | ACGCCGAGGT | 200 |

-continued

| | | | | | |
|---|---|---|---|---|---|
| AACAATGGCG | CAACAGCGAT | TGGCACAAGA | ACCGTTTTTT | CAGCAAGTAG | 250 |
| GGTATAATGG | GACACCTGGA | GATCCAGAAG | AACCCAAAGA | ACAGTCATTC | 300 |
| CACGAAGAGG | AAGAGGAAGT | TGCAGTTTCA | GAAATTCGAA | CAGTTGTGCG | 350 |
| CACTGAACGA | CATGTGCATG | ATTCGGAAAA | TGGTCCTATT | GTGGAAGAGC | 400 |
| GTACAATAAC | AACTACGTAT | GAGGATGATG | TTGCTGTAAA | CGAAGAAGAA | 450 |
| ATTGTTGACA | AAATAGTGCC | TCTCAACGAA | GAGGAGCAAG | AAAAATGGGA | 500 |
| TCGAATGGTT | CGAGAAGTGG | AAATGAATTT | TGAGCAACAA | GAAACATCAA | 550 |
| AAGAAGGAAC | GTTTGGTTGT | CAGACAACAC | ATGAGAAAGA | AAAAGATGAT | 600 |
| GATGGTGGCA | GTCTGAAGAC | GACAATGAAA | GATAGTCACG | TAAGGCAGAT | 650 |
| TTTCTTCGAT | GGAGGTGAGA | CATCCGCTAA | TGAAACAGGA | TTAAGTAGCG | 700 |
| GGGATGCAGA | CACTATTATG | ACTCCAACGA | CAAAGGAGGA | TAATCATGTT | 750 |
| ATAGACGTAA | TGGAGGAAAG | GCGAACTGAT | GAAGAGGCCA | AAGGGCAAAG | 800 |
| CGTTCATGAA | | | | | 810 |

(2) INFORMATION FOR SEQ ID NO:10:

(i) SEQUENCE CHARACTERISTICS:
        (A) LENGTH: 810 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

| | | | | | |
|---|---|---|---|---|---|
| TTCATGAACG | CTTTGCCCTT | TGGCCTCTTC | ATCAGTTCGC | CTTTCCTCCA | 50 |
| TTACGTCTAT | AACATGATTA | TCCTCCTTTG | TCGTTGGAGT | CATAATAGTG | 100 |
| TCTGCATCCC | CGCTACTTAA | TCCTGTTTCA | TTAGCGGATG | TCTCACCTCC | 150 |
| ATCGAAGAAA | ATCTGCCTTA | CGTGACTATC | TTTCATTGTC | GTCTTCAGAC | 200 |
| TGCCACCATC | ATCATCTTTT | TCTTTCTCAT | GTGTTGTCTG | ACAACCAAAC | 250 |
| GTTCCTTCTT | TTGATGTTTC | TTGTTGCTCA | AAATTCATTT | CCACTTCTCG | 300 |
| AACCATTCGA | TCCCATTTTT | CTTGCTCCTC | TTCGTTGAGA | GGCACTATTT | 350 |
| TGTCAACAAT | TTCTTCTTCG | TTTACAGCAA | CATCATCCTC | ATACGTAGTT | 400 |
| GTTATTGTAC | GCTCTTCCAC | AATAGGACCA | TTTTCGAAT | CATGCACATG | 450 |
| TCGTTCAGTG | CGCACAACTG | TTCGAATTTC | TGAAACTGCA | ACTTCCTCTT | 500 |
| CCTCTTCGTG | GAATGACTGT | TCTTTGGGTT | CTTCTGGATC | TCCAGGTGTC | 550 |
| CCATTATACC | CTACTTGCTG | AAAAAACGGT | TCTTGTGCCA | ATCGCTGTTG | 600 |
| CGCCATTGTT | ACCTCGGCGT | GACGACGTCT | GTCGCCTGCT | ACCTCTAGCA | 650 |
| AAGTAGATGA | CAGAGTTATT | GAGGGTCCAG | AAATATGCGA | TACAGGTGTT | 700 |
| CCTTCTAAAC | CATCTAGCTT | TTCAGCTCGA | TCCATTTCTC | GTACAACATC | 750 |
| ATCACGTCCT | ATTCGCTGCA | ATGCTGATCG | CAAAGCAACG | GGCGTAGCTT | 800 |
| GTTCTTTCTT | | | | | 810 |

(2) INFORMATION FOR SEQ ID NO:11:

(i) SEQUENCE CHARACTERISTICS:
        (A) LENGTH: 600 nucleotides
        (B) TYPE: nucleic acid
        (C) STRANDEDNESS: single ( D ) TOPOLOGY: linear ( i i ) MOLECULE TYPE: cDNA ( i x ) FEATURE:
    ( A ) NAME/KEY: CDS
    ( B ) LOCATION: 1..600

( x i ) SEQUENCE DESCRIPTION: SEQ ID NO:11:

| GCC | CAG | CCA | GTT | CCA | CAA | GAG | ATA | GTC | ACT | CGT | TTA | CAT | GGG | 42 |
|---|---|---|---|---|---|---|---|---|---|---|---|---|---|---|
| Ala | Gln | Pro | Val | Pro | Gln | Glu | Ile | Val | Thr | Arg | Leu | His | Gly | |
| 1 | | | | 5 | | | | | 10 | | | | | |

| AAT | AGA | GTC | GCT | GTT | TCT | CCA | ATT | GTA | ACT | GTT | GAA | CCG | CGT | 84 |
|---|---|---|---|---|---|---|---|---|---|---|---|---|---|---|
| Asn | Arg | Val | Ala | Val | Ser | Pro | Ile | Val | Thr | Val | Glu | Pro | Arg | |
| 15 | | | | | 20 | | | | | 25 | | | | |

| CGT | CGC | AAA | TTC | CAT | AAG | CCC | ATA | ACG | CTG | TGC | ATA | CCA | TTG | 126 |
|---|---|---|---|---|---|---|---|---|---|---|---|---|---|---|
| Arg | Arg | Lys | Phe | His | Lys | Pro | Ile | Thr | Leu | Cys | Ile | Pro | Leu | |
| | 30 | | | | | 35 | | | | | 40 | | | |

| CCA | CAA | AGC | TCA | AAT | AAA | GGA | ATG | TTA | ACA | CAA | TAT | AGT | GGC | 168 |
|---|---|---|---|---|---|---|---|---|---|---|---|---|---|---|
| Pro | Gln | Ser | Ser | Asn | Lys | Gly | Met | Leu | Thr | Gln | Tyr | Ser | Gly | |
| | | 45 | | | | | 50 | | | | | 55 | | |

| CAA | CCA | GGA | CAG | GAA | CCA | CCG | ACG | CTG | CGT | TTA | CTC | TGC | AGT | 210 |
|---|---|---|---|---|---|---|---|---|---|---|---|---|---|---|
| Gln | Pro | Gly | Gln | Glu | Pro | Pro | Thr | Leu | Arg | Leu | Leu | Cys | Ser | |
| | | | 60 | | | | | 65 | | | | | 70 | |

| AAA | ACT | GGA | GGT | TCT | TCT | CCT | GCA | CAG | TGG | GAA | GAT | ATT | ACT | 252 |
|---|---|---|---|---|---|---|---|---|---|---|---|---|---|---|
| Lys | Thr | Gly | Gly | Ser | Ser | Pro | Ala | Gln | Trp | Glu | Asp | Ile | Thr | |
| | | | | 75 | | | | | 80 | | | | | |

| GGA | ACT | ACC | CAG | TTA | ACA | TTT | ACT | GGT | GAG | GAC | GTT | TCA | TTT | 294 |
|---|---|---|---|---|---|---|---|---|---|---|---|---|---|---|
| Gly | Thr | Thr | Gln | Leu | Thr | Phe | Thr | Gly | Glu | Asp | Val | Ser | Phe | |
| 85 | | | | | 90 | | | | | 95 | | | | |

| ACA | ACT | ACG | GTT | TCT | GCT | CGA | TTT | TGG | TTG | ATG | GAT | TGC | CAA | 336 |
|---|---|---|---|---|---|---|---|---|---|---|---|---|---|---|
| Thr | Thr | Thr | Val | Ser | Ala | Arg | Phe | Trp | Leu | Met | Asp | Cys | Gln | |
| | 100 | | | | | 105 | | | | | 110 | | | |

| ACT | CCG | CGA | GAT | GCG | GCA | CGA | ATG | GCA | CAA | GAA | GTT | TAC | AAT | 378 |
|---|---|---|---|---|---|---|---|---|---|---|---|---|---|---|
| Thr | Pro | Arg | Asp | Ala | Ala | Arg | Met | Ala | Gln | Glu | Val | Tyr | Asn | |
| | | | 115 | | | | | 120 | | | | | 125 | |

| GAA | GCA | ATT | GCA | GTT | CCT | TAT | ATG | GCT | AAA | TTT | CTT | ATT | TTT | 420 |
|---|---|---|---|---|---|---|---|---|---|---|---|---|---|---|
| Glu | Ala | Ile | Ala | Val | Pro | Tyr | Met | Ala | Lys | Phe | Leu | Ile | Phe | |
| | | | 130 | | | | | 135 | | | | | 140 | |

| GCT | CGA | CGA | ACT | TTT | CCT | GCC | GAA | GGA | CAG | TTG | AGA | TTG | TTT | 462 |
|---|---|---|---|---|---|---|---|---|---|---|---|---|---|---|
| Ala | Arg | Arg | Thr | Phe | Pro | Ala | Glu | Gly | Gln | Leu | Arg | Leu | Phe | |
| | | | | 145 | | | | | 150 | | | | | |

| TGT | ATG | ACT | GAT | GAT | CGG | GAA | GAT | AAA | ACC | CTG | GAA | AAA | CAA | 504 |
|---|---|---|---|---|---|---|---|---|---|---|---|---|---|---|
| Cys | Met | Thr | Asp | Asp | Arg | Glu | Asp | Lys | Thr | Leu | Glu | Lys | Gln | |
| 155 | | | | | 160 | | | | | 165 | | | | |

| GAA | CGT | TTC | ATT | GAA | ATT | GCG | AAA | TCG | AAA | GAT | GTA | GAA | GTC | 546 |
|---|---|---|---|---|---|---|---|---|---|---|---|---|---|---|
| Glu | Arg | Phe | Ile | Glu | Ile | Ala | Lys | Ser | Lys | Asp | Val | Glu | Val | |
| | 170 | | | | | 175 | | | | | 180 | | | |

| TTA | AGT | GGG | CGA | CAT | CAG | TTT | TTG | GAA | TTT | TCT | GGA | AAT | CTT | 588 |
|---|---|---|---|---|---|---|---|---|---|---|---|---|---|---|
| Leu | Ser | Gly | Arg | His | Gln | Phe | Leu | Glu | Phe | Ser | Gly | Asn | Leu | |
| | | 185 | | | | | 190 | | | | | 195 | | |

| CTT | CCA | ATA | ACC | 600 |
|---|---|---|---|---|
| Leu | Pro | Ile | Thr | |
| | | | 200 | |

( 2 ) INFORMATION FOR SEQ ID NO:12:

( i ) SEQUENCE CHARACTERISTICS:
        ( A ) LENGTH: 200 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Ala | Gln | Pro | Val | Pro | Gln | Glu | Ile | Val | Thr | Arg | Leu | His | Gly |
| 1 | | | | 5 | | | | | 10 | | | | |

| Asn | Arg | Val | Ala | Val | Ser | Pro | Ile | Val | Thr | Val | Glu | Pro | Arg |
| 15 | | | | | 20 | | | | | 25 | | | |

| Arg | Arg | Lys | Phe | His | Lys | Pro | Ile | Thr | Leu | Cys | Ile | Pro | Leu |
| | 30 | | | | | 35 | | | | | 40 | | |

| Pro | Gln | Ser | Ser | Asn | Lys | Gly | Met | Leu | Thr | Gln | Tyr | Ser | Gly |
| | | | 45 | | | | 50 | | | | | 55 | |

| Gln | Pro | Gly | Gln | Glu | Pro | Pro | Thr | Leu | Arg | Leu | Leu | Cys | Ser |
| | | | 60 | | | | | 65 | | | | | 70 |

| Lys | Thr | Gly | Gly | Ser | Ser | Pro | Ala | Gln | Trp | Glu | Asp | Ile | Thr |
| | | | | 75 | | | | | 80 | | | | |

| Gly | Thr | Thr | Gln | Leu | Thr | Phe | Thr | Gly | Glu | Asp | Val | Ser | Phe |
| 85 | | | | | 90 | | | | | 95 | | | |

| Thr | Thr | Thr | Val | Ser | Ala | Arg | Phe | Trp | Leu | Met | Asp | Cys | Gln |
| | 100 | | | | | 105 | | | | | 110 | | |

| Thr | Pro | Arg | Asp | Ala | Ala | Arg | Met | Ala | Gln | Glu | Val | Tyr | Asn |
| | | 115 | | | | | 120 | | | | | 125 | |

| Glu | Ala | Ile | Ala | Val | Pro | Tyr | Met | Ala | Lys | Phe | Leu | Ile | Phe |
| | | | 130 | | | | 135 | | | | | | 140 |

| Ala | Arg | Arg | Thr | Phe | Pro | Ala | Glu | Gly | Gln | Leu | Arg | Leu | Phe |
| | | | | 145 | | | | | 150 | | | | |

| Cys | Met | Thr | Asp | Asp | Arg | Glu | Asp | Lys | Thr | Leu | Glu | Lys | Gln |
| 155 | | | | | 160 | | | | | 165 | | | |

| Glu | Arg | Phe | Ile | Glu | Ile | Ala | Lys | Ser | Lys | Asp | Val | Glu | Val |
| | 170 | | | | | 175 | | | | | 180 | | |

| Leu | Ser | Gly | Arg | His | Gln | Phe | Leu | Glu | Phe | Ser | Gly | Asn | Leu |
| | | | | 185 | | | | 190 | | | | | 195 |

| Leu | Pro | Ile | Thr |
| | | | 200 |

( 2 ) INFORMATION FOR SEQ ID NO:13:

( i ) SEQUENCE CHARACTERISTICS:
( A ) LENGTH: 600 nucleotides
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:13:

| GGTTATTGGA | AGAAGATTTC | CAGAAAATTC | CAAAAACTGA | TGTCGCCCAC | 50 |
| TTAAGACTTC | TACATCTTTC | GATTTCGCAA | TTTCAATGAA | ACGTTCTTGT | 100 |
| TTTTCCAGGG | TTTTATCTTC | CCGATCATCA | GTCATACAAA | ACAATCTCAA | 150 |
| CTGTCCTTCG | GCAGGAAAAG | TTCGTCGAGC | AAAAATAAGA | AATTTAGCCA | 200 |
| TATAAGGAAC | TGCAATTGCT | TCATTGTAAA | CTTCTTGTGC | CATTCGTGCC | 250 |
| GCATCTCGCG | GAGTTTGGCA | ATCCATCAAC | CAAAATCGAG | CAGAAACCGT | 300 |
| AGTTGTAAAT | GAAACGTCCT | CACCAGTAAA | TGTTAACTGG | GTAGTTCCAG | 350 |
| TAATATCTTC | CCACTGTGCA | GGAGAAGAAC | CTCCAGTTTT | ACTGCAGAGT | 400 |
| AAACGCAGCG | TCGGTGGTTC | CTGTCCTGGT | TGGCCACTAT | ATTGTGTTAA | 450 |
| CATTCCTTTA | TTTGAGCTTT | GTGGCAATGG | TATGCACAGC | GTTATGGGCT | 500 |

-continued

```
TATGGAATTT GCGACGACGC GGTTCAACAG TTACAATTGG AGAAACAGCG                550

ACTCTATTCC CATGTAAACG AGTGACTATC TCTTGTGGAA CTGGCTGGGC                600
```

(2) INFORMATION FOR SEQ ID NO:14:

(i) SEQUENCE CHARACTERISTICS:
        (A) LENGTH: 1228 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1227

(xi) SEQUENCE DESCRIPTION: SEQ ID NO:14:

```
CAT CAA GCT GCT CAG CAA GGG CAT AAC AGT GTT GTA CGT TAC               42
His Gln Ala Ala Gln Gln Gly His Asn Ser Val Val Arg Tyr
 1               5                  10

TTG TTG GAA CAT GGT GCA AGT CCA AAT GTT CAT ACA TCG ACA               84
Leu Leu Glu His Gly Ala Ser Pro Asn Val His Thr Ser Thr
 15                  20                  25

GGA CAA ACT CCA TTA TCG ATT GCT GAA CGT CTA GGG TAT GTA              126
Gly Gln Thr Pro Leu Ser Ile Ala Glu Arg Leu Gly Tyr Val
         30                  35                  40

TCC GTG GTT GAA GCG CTT AAA ACA ATT ACC GAG ACT ACT GTG              168
Ser Val Val Glu Ala Leu Lys Thr Ile Thr Glu Thr Thr Val
             45                  50                  55

ATA ACG GAG ACC ACA ACC GTT ACT GAA GAA AGA TAT AAA CCT              210
Ile Thr Glu Thr Thr Thr Val Thr Glu Glu Arg Tyr Lys Pro
                 60                  65                  70

CAG AAT CCC GAA GCA ATG AAT GAA ACC ATG TTT TCC GAT TCC              252
Gln Asn Pro Glu Ala Met Asn Glu Thr Met Phe Ser Asp Ser
                     75                  80

GAA GAT GAA GGT GAA GAT AAT CAG ATC ACA GCC AAT GCT CAT              294
Glu Asp Glu Gly Glu Asp Asn Gln Ile Thr Ala Asn Ala His
 85                  90                  95

GCT CAT GAT TTC TCA GAA AGC CTC ACA AAA GGT TTG CAC GAT              336
Ala His Asp Phe Ser Glu Ser Leu Thr Lys Gly Leu His Asp
        100                 105                 110

TCA ACT GGT GTA CAT TTG ATT CAT GCC ACA GAA CCG ACA TTG              378
Ser Thr Gly Val His Leu Ile His Ala Thr Glu Pro Thr Leu
            115                 120                 125

TCA CGA AGT CCG GAA GTG GAA GGT ACG GAT GGC GAT TTG GAT              420
Ser Arg Ser Pro Glu Val Glu Gly Thr Asp Gly Asp Leu Asp
                130                 135                 140

GCC TTA ATT CGT AAA GCA CAA CAT GAA CCA ATT ACT ACA GCG              462
Ala Leu Ile Arg Lys Ala Gln His Glu Pro Ile Thr Thr Ala
                    145                 150

ATG GCC GAT CCT TCC TTA GAT GCA TCG CTT CCT GAC AAT GTT              504
Met Ala Asp Pro Ser Leu Asp Ala Ser Leu Pro Asp Asn Val
155                 160                 165

ACG ATA ATG AGA ACT ACC ATG CAA CCT AGT TTT TTA ATT TCG              546
Thr Ile Met Arg Thr Thr Met Gln Pro Ser Phe Leu Ile Ser
        170                 175                 180

TTT ATG GTG GAT GCA CGT GGA GGA GCA ATG CGT GGT TGT AGG              588
Phe Met Val Asp Ala Arg Gly Gly Ala Met Arg Gly Cys Arg
            185                 190                 195

CAT TCC GGT GTC AGA ATC ATT ATA CCA CCG AGG AAA GCG CCG              630
His Ser Gly Val Arg Ile Ile Ile Pro Pro Arg Lys Ala Pro
                200                 205                 210
```

| | | | | | | | | | | | | | |
|---|---|---|---|---|---|---|---|---|---|---|---|---|---|
| CAA | CCT | ACA | CGG | GTC | ACA | TGC | AGA | TAC | CTT | GGA | AAG | GAC | AAG | 672 |
| Gln | Pro | Thr | Arg | Val | Thr | Cys | Arg | Tyr | Leu | Gly | Lys | Asp | Lys | |
| | | | | 215 | | | | | 220 | | | | | |
| TTA | GCG | CAT | CCA | CCA | CCA | TTA | AGT | GAA | GGT | GAA | GCG | CTC | GCN | 714 |
| Leu | Ala | His | Pro | Pro | Pro | Leu | Ser | Glu | Gly | Glu | Ala | Leu | Ala | |
| 225 | | | | | 230 | | | | | 235 | | | | |
| TCA | CGT | ATA | CTT | GAA | ATG | GCA | CCA | CAT | GGA | GCA | AAA | TTC | TTA | 756 |
| Ser | Arg | Ile | Leu | Glu | Met | Ala | Pro | His | Gly | Ala | Lys | Phe | Leu | |
| | 240 | | | | | 245 | | | | | 250 | | | |
| GGC | CCT | GTT | ATA | TTG | GAA | GTA | CCA | CAT | TTT | GCA | TCA | CTT | CGT | 798 |
| Gly | Pro | Val | Ile | Leu | Glu | Val | Pro | His | Phe | Ala | Ser | Leu | Arg | |
| | | 255 | | | | | 260 | | | | | 265 | | |
| GGA | CGA | GAG | AGA | GAG | ATT | GTC | ATT | TTG | CGT | TCT | GAT | GAT | GGG | 840 |
| Gly | Arg | Glu | Arg | Glu | Ile | Val | Ile | Leu | Arg | Ser | Asp | Asp | Gly | |
| | | | 270 | | | | | 275 | | | | | 280 | |
| CAG | CAT | TGG | AAA | GAG | CAT | CAG | CTT | GAA | GCA | ACA | GAA | GAT | GCT | 882 |
| Gln | His | Trp | Lys | Glu | His | Gln | Leu | Glu | Ala | Thr | Glu | Asp | Ala | |
| | | | | 285 | | | | | 290 | | | | | |
| GTA | CAA | GAG | GTG | CTC | AAT | GAA | TCG | TTT | GAT | GCA | GAA | GAG | TTG | 924 |
| Val | Gln | Glu | Val | Leu | Asn | Glu | Ser | Phe | Asp | Ala | Glu | Glu | Leu | |
| 295 | | | | | 300 | | | | | 305 | | | | |
| TCG | CAA | CTT | GAT | GAT | TTG | CAT | ACA | TCA | CGG | ATT | ACG | CGT | ATC | 966 |
| Ser | Gln | Leu | Asp | Asp | Leu | His | Thr | Ser | Arg | Ile | Thr | Arg | Ile | |
| | 310 | | | | | 315 | | | | | 320 | | | |
| CTG | ACC | AAT | GAT | TTC | CCA | ATG | TAT | TTC | GCG | GTC | GTT | ACT | CGT | 1008 |
| Leu | Thr | Asn | Asp | Phe | Pro | Met | Tyr | Phe | Ala | Val | Val | Thr | Arg | |
| | | 325 | | | | | 330 | | | | | 335 | | |
| GTG | CGG | CAA | GAA | GTG | CAC | TGT | GTT | GGT | CCA | GAA | GGT | GGT | GTA | 1050 |
| Val | Arg | Gln | Glu | Val | His | Cys | Val | Gly | Pro | Glu | Gly | Gly | Val | |
| | | | 340 | | | | | 345 | | | | | 350 | |
| ATA | CTC | TCT | TCA | GTT | GTT | CCT | CAT | GTG | CAG | GCC | ATA | TTT | CCG | 1092 |
| Ile | Leu | Ser | Ser | Val | Val | Pro | His | Val | Gln | Ala | Ile | Phe | Pro | |
| | | | | 355 | | | | | 360 | | | | | |
| GAT | GGT | TCC | TTG | ACT | AAG | ACG | ATC | AAA | GTA | TCT | GTG | CAA | GCC | 1134 |
| Asp | Gly | Ser | Leu | Thr | Lys | Thr | Ile | Lys | Val | Ser | Val | Gln | Ala | |
| 365 | | | | | 370 | | | | | 375 | | | | |
| CAG | CCA | GTT | CCA | CAA | GAG | ATA | GTC | ACT | CGT | TTA | CAT | GGG | AAT | 1176 |
| Gln | Pro | Val | Pro | Gln | Glu | Ile | Val | Thr | Arg | Leu | His | Gly | Asn | |
| | 380 | | | | | 385 | | | | | 390 | | | |
| AGA | GTC | GCT | GTT | TCT | CCA | ATT | GTA | ACT | GTT | GAA | CCG | CGT | CGT | 1218 |
| Arg | Val | Ala | Val | Ser | Pro | Ile | Val | Thr | Val | Glu | Pro | Arg | Arg | |
| | | 395 | | | | | 400 | | | | | 405 | | |
| CGC | AAA | TTC | C | | | | | | | | | | | 1228 |
| Arg | Lys | Phe | | | | | | | | | | | | |

( 2 ) INFORMATION FOR SEQ ID NO:15:

( i ) SEQUENCE CHARACTERISTICS:
        ( A ) LENGTH: 409 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

| | | | | | | | | | | | |
|---|---|---|---|---|---|---|---|---|---|---|---|
| His | Gln | Ala | Ala | Gln | Gln | Gly | His | Asn | Ser | Val | Val | Arg | Tyr |
| 1 | | | | 5 | | | | | 10 | | | | |
| Leu | Leu | Glu | His | Gly | Ala | Ser | Pro | Asn | Val | His | Thr | Ser | Thr |
| 15 | | | | | 20 | | | | | 25 | | | |
| Gly | Gln | Thr | Pro | Leu | Ser | Ile | Ala | Glu | Arg | Leu | Gly | Tyr | Val |
| | 30 | | | | | 35 | | | | | 40 | | |

| | | | | | | | | | | | |
|---|---|---|---|---|---|---|---|---|---|---|---|
| Ser | Val | Val | Glu | Ala | Leu | Lys | Thr | Ile | Thr | Glu | Thr | Thr | Val |
| | | 45 | | | | 50 | | | | 55 | |
| Ile | Thr | Glu | Thr | Thr | Thr | Val | Thr | Glu | Glu | Arg | Tyr | Lys | Pro |
| | | | 60 | | | | 65 | | | | 70 |
| Gln | Asn | Pro | Glu | Ala | Met | Asn | Glu | Thr | Met | Phe | Ser | Asp | Ser |
| | | | | 75 | | | | | 80 | | |
| Glu | Asp | Glu | Gly | Glu | Asp | Asn | Gln | Ile | Thr | Ala | Asn | Ala | His |
| 85 | | | | | 90 | | | | | 95 | | |
| Ala | His | Asp | Phe | Ser | Glu | Ser | Leu | Thr | Lys | Gly | Leu | His | Asp |
| | | 100 | | | | 105 | | | | 110 | |
| Ser | Thr | Gly | Val | His | Leu | Ile | His | Ala | Thr | Glu | Pro | Thr | Leu |
| | | | 115 | | | | 120 | | | | 125 |
| Ser | Arg | Ser | Pro | Glu | Val | Glu | Gly | Thr | Asp | Gly | Asp | Leu | Asp |
| | | | 130 | | | | 135 | | | | 140 |
| Ala | Leu | Ile | Arg | Lys | Ala | Gln | His | Glu | Pro | Ile | Thr | Thr | Ala |
| | | | | 145 | | | | | 150 | | |
| Met | Ala | Asp | Pro | Ser | Leu | Asp | Ala | Ser | Leu | Pro | Asp | Asn | Val |
| 155 | | | | | 160 | | | | | 165 | | |
| Thr | Ile | Met | Arg | Thr | Thr | Met | Gln | Pro | Ser | Phe | Leu | Ile | Ser |
| | | 170 | | | | 175 | | | | 180 | |
| Phe | Met | Val | Asp | Ala | Arg | Gly | Gly | Ala | Met | Arg | Gly | Cys | Arg |
| | | 185 | | | | 190 | | | | 195 | |
| His | Ser | Gly | Val | Arg | Ile | Ile | Ile | Pro | Pro | Arg | Lys | Ala | Pro |
| | | | 200 | | | | 205 | | | | 210 |
| Gln | Pro | Thr | Arg | Val | Thr | Cys | Arg | Tyr | Leu | Gly | Lys | Asp | Lys |
| | | | | 215 | | | | | 220 | | |
| Leu | Ala | His | Pro | Pro | Leu | Ser | Gly | Glu | Ala | Leu | Ala |
| 225 | | | | 230 | | | | 235 | | |
| Ser | Arg | Ile | Leu | Glu | Met | Ala | Pro | His | Gly | Ala | Lys | Phe | Leu |
| | 240 | | | | 245 | | | | | 250 | |
| Gly | Pro | Val | Ile | Leu | Glu | Val | Pro | His | Phe | Ala | Ser | Leu | Arg |
| | | 255 | | | | 260 | | | | 265 | |
| Gly | Arg | Glu | Arg | Glu | Ile | Val | Ile | Leu | Arg | Ser | Asp | Asp | Gly |
| | | | 270 | | | | 275 | | | | 280 |
| Gln | His | Trp | Lys | Glu | His | Gln | Leu | Glu | Ala | Thr | Glu | Asp | Ala |
| | | | | 285 | | | | | 290 | | |
| Val | Gln | Glu | Val | Leu | Asn | Glu | Ser | Phe | Asp | Ala | Glu | Glu | Leu |
| 295 | | | | | 300 | | | | | 305 | | |
| Ser | Gln | Leu | Asp | Asp | Leu | His | Thr | Ser | Arg | Ile | Thr | Arg | Ile |
| | 310 | | | | | 315 | | | | 320 | |
| Leu | Thr | Asn | Asp | Phe | Pro | Met | Tyr | Phe | Ala | Val | Val | Thr | Arg |
| | | 325 | | | | 330 | | | | 335 | |
| Val | Arg | Gln | Glu | Val | His | Cys | Val | Gly | Pro | Glu | Gly | Gly | Val |
| | | 340 | | | | 345 | | | | 350 |
| Ile | Leu | Ser | Ser | Val | Val | Pro | His | Val | Gln | Ala | Ile | Phe | Pro |
| | | | 355 | | | | 360 | | | |
| Asp | Gly | Ser | Leu | Thr | Lys | Thr | Ile | Lys | Val | Ser | Val | Gln | Ala |
| 365 | | | | | 370 | | | | 375 | | |
| Gln | Pro | Val | Pro | Gln | Glu | Ile | Val | Thr | Arg | Leu | His | Gly | Asn |
| | | 380 | | | | 385 | | | | 390 | |
| Arg | Val | Ala | Val | Ser | Pro | Ile | Val | Thr | Val | Glu | Pro | Arg | Arg |
| | | 395 | | | | 400 | | | | 405 |
| Arg | Lys | Phe |

( 2 ) INFORMATION FOR SEQ ID NO:16:

( i ) SEQUENCE CHARACTERISTICS:
        ( A ) LENGTH: 1228 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

| | | | | | |
|---|---|---|---|---|---|
| GGAATTTGCG | ACGACGCGGT | TCAACAGTTA | CAATTGGAGA | AACAGCGACT | 50 |
| CTATTCCCAT | GTAAACGAGT | GACTATCTCT | TGTGGAACTG | GCTGGGCTTG | 100 |
| CACAGATACT | TTGATCGTCT | TAGTCAAGGA | ACCATCCGGA | AATATGGCCT | 150 |
| GCACATGAGG | AACAACTGAA | GAGAGTATTA | CACCACCTTC | TGGACCAACA | 200 |
| CAGTGCACTT | CTTGCCGCAC | ACGAGTAACG | ACCGCGAAAT | ACATTGGGAA | 250 |
| ATCATTGGTC | AGGATACGCG | TAATCCGTGA | TGTATGCAAA | TCATCAAGTT | 300 |
| GCGACAACTC | TTCTGCATCA | AACGATTCAT | TGAGCACCTC | TTGTACAGCA | 350 |
| TCTTCTGTTG | CTTCAAGCTG | ATGCTCTTTC | CAATGCTGCC | CATCATCAGA | 400 |
| ACGCAAAATG | ACAATCTCTC | TCTCTCGTCC | ACGAAGTGAT | GCAAAATGTG | 450 |
| GTACTTCCAA | TATAACAGGG | CCTAAGAATT | TTGCTCCATG | TGGTGCCATT | 500 |
| TCAAGTATAC | GTGANGCGAG | CGCTTCACCT | TCACTTAATG | GTGGTGGATG | 550 |
| CGCTAACTTG | TCCTTTCCAA | GGTATCTGCA | TGTGACCCGT | GTAGGTTGCG | 600 |
| GCGCTTTCCT | CGGTGGTATA | ATGATTCTGA | CACCGGAATG | CCTACAACCA | 650 |
| CGCATTGCTC | CTCCACGTGC | ATCCACCATA | AACGAAATTA | AAAAACTAGG | 700 |
| TTGCATGGTA | GTTCTCATTA | TCGTAACATT | GTCAGGAAGC | GATGCATCTA | 750 |
| AGGAAGGATC | GGCCATCGCT | GTAGTAATTG | GTTCATGTTG | TGCTTTACGA | 800 |
| ATTAAGGCAT | CCAAATCGCC | ATCCGTACCT | TCCACTTCCG | GACTTCGTGA | 850 |
| CAATGTCGGT | TCTGTGGCAT | GAATCAAATG | TACACCAGTT | GAATCGTGCA | 900 |
| AACCTTTTGT | GAGGCTTTCT | GAGAAATCAT | GAGCATGAGC | ATTGGCTGTG | 950 |
| ATCTGATTAT | CTTCACCTTC | ATCTTCGGAA | TCGGAAAACA | TGGTTTCATT | 1000 |
| CATTGCTTCG | GGATTCTGAG | GTTTATATCT | TTCTTCAGTA | ACGGTTGTGG | 1050 |
| TCTCCGTTAT | CACAGTAGTC | TCGGTAATTG | TTTTAAGCGC | TTCAACCACG | 1100 |
| GATACATACC | CTAGACGTTC | AGCAATCGAT | AATGGAGTTT | GTCCTGTCGA | 1150 |
| TGTATGAACA | TTTGGACTTG | CACCATGTTC | CAACAAGTAA | CGTACAACAC | 1200 |
| TGTTATGCCC | TTGCTGAGCA | GCTTGATG | | | 1228 |

( 2 ) INFORMATION FOR SEQ ID NO:17:

( i ) SEQUENCE CHARACTERISTICS:
        ( A ) LENGTH: 1227 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

| | | | | | |
|---|---|---|---|---|---|
| CATCAAGCTG | CTCAGCAAGG | GCATAACAGT | GTTGTACGTT | ACTTGTTGGA | 50 |
| ACATGGTGCA | AGTCCAAATG | TTCATACATC | GACAGGACAA | ACTCCATTAT | 100 |

| | | | | | |
|---|---|---|---|---|---|
| CGATTGCTGA | ACGTCTAGGG | TATGTATCCG | TGGTTGAAGC | GCTTAAAACA | 150 |
| ATTACCGAGA | CTACTGTGAT | AACGGAGACC | ACAACCGTTA | CTGAAGAAAG | 200 |
| ATATAAACCT | CAGAATCCCG | AAGCAATGAA | TGAAACCATG | TTTTCCGATT | 250 |
| CCGAAGATGA | AGGTGAAGAT | AATCAGATCA | CAGCCAATGC | TCATGCTCAT | 300 |
| GATTTCTCAG | AAAGCCTCAC | AAAAGGTTTG | CACGATTCAA | CTGGTGTACA | 350 |
| TTTGATTCAT | GCCACAGAAC | CGACATTGTC | ACGAAGTCCG | GAAGTGGAAG | 400 |
| GTACGGATGG | CGATTTGGAT | GCCTTAATTC | GTAAAGCACA | ACATGAACCA | 450 |
| ATTACTACAG | CGATGGCCGA | TCCTTCCTTA | GATGCATCGC | TTCCTGACAA | 500 |
| TGTTACGATA | ATGAGAACTA | CCATGCAACC | TAGTTTTTTA | ATTTCGTTTA | 550 |
| TGGTGGATGC | ACGTGGAGGA | GCAATGCGTG | GTTGTAGGCA | TTCCGGTGTC | 600 |
| AGAATCATTA | TACCACCGAG | GAAAGCGCCG | CAACCTACAC | GGGTCACATG | 650 |
| CAGATACCTT | GGAAAGGACA | AGTTAGCGCA | TCCACCACCA | TTAAGTGAAG | 700 |
| GTGAAGCGCT | CGCNTCACGT | ATACTTGAAA | TGGCACCACA | TGGAGCAAAA | 750 |
| TTCTTAGGCC | CTGTTATATT | GGAAGTACCA | CATTTTGCAT | CACTTCGTGG | 800 |
| ACGAGAGAGA | GAGATTGTCA | TTTTGCGTTC | TGATGATGGG | CAGCATTGGA | 850 |
| AAGAGCATCA | GCTTGAAGCA | ACAGAAGATG | CTGTACAAGA | GGTGCTCAAT | 900 |
| GAATCGTTTG | ATGCAGAAGA | GTTGTCGCAA | CTTGATGATT | TGCATACATC | 950 |
| ACGGATTACG | CGTATCCTGA | CCAATGATTT | CCCAATGTAT | TTCGCGGTCG | 1000 |
| TTACTCGTGT | GCGGCAAGAA | GTGCACTGTG | TTGGTCCAGA | AGGTGGTGTA | 1050 |
| ATACTCTCTT | CAGTTGTTCC | TCATGTGCAG | GCCATATTTC | CGGATGGTTC | 1100 |
| CTTGACTAAG | ACGATCAAAG | TATCTGTGCA | AGCCCAGCCA | GTTCCACAAG | 1150 |
| AGATAGTCAC | TCGTTTACAT | GGGAATAGAG | TCGCTGTTTC | TCCAATTGTA | 1200 |
| ACTGTTGAAC | CGCGTCGTCG | CAAATTC | | | 1227 |

( 2 ) INFORMATION FOR SEQ ID NO:18:

( i ) SEQUENCE CHARACTERISTICS:
        ( A ) LENGTH: 1227 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

| | | | | | |
|---|---|---|---|---|---|
| GAATTTGCGA | CGACGCGGTT | CAACAGTTAC | AATTGGAGAA | ACAGCGACTC | 50 |
| TATTCCCATG | TAAACGAGTG | ACTATCTCTT | GTGGAACTGG | CTGGGCTTGC | 100 |
| ACAGATACTT | TGATCGTCTT | AGTCAAGGAA | CCATCCGGAA | ATATGGCCTG | 150 |
| CACATGAGGA | ACAACTGAAG | AGAGTATTAC | ACCACCTTCT | GGACCAACAC | 200 |
| AGTGCACTTC | TTGCCGCACA | CGAGTAACGA | CCGCGAAATA | CATTGGGAAA | 250 |
| TCATTGGTCA | GGATACGCGT | AATCCGTGAT | GTATGCAAAT | CATCAAGTTG | 300 |
| CGACAACTCT | TCTGCATCAA | ACGATTCATT | GAGCACCTCT | TGTACAGCAT | 350 |
| CTTCTGTTGC | TTCAAGCTGA | TGCTCTTTCC | AATGCTGCCC | ATCATCAGAA | 400 |
| CGCAAAATGA | CAATCTCTCT | CTCTCGTCCA | CGAAGTGATG | CAAAATGTGG | 450 |
| TACTTCCAAT | ATAACAGGGC | CTAAGAATTT | TGCTCCATGT | GGTGCCATTT | 500 |

-continued

| | | | | | |
|---|---|---|---|---|---|
| CAAGTATACG | TGANGCGAGC | GCTTCACCTT | CACTTAATGG | TGGTGGATGC | 550 |
| GCTAACTTGT | CCTTTCCAAG | GTATCTGCAT | GTGACCCGTG | TAGGTTGCGG | 600 |
| CGCTTTCCTC | GGTGGTATAA | TGATTCTGAC | ACCGGAATGC | CTACAACCAC | 650 |
| GCATTGCTCC | TCCACGTGCA | TCCACCATAA | ACGAAATTAA | AAAACTAGGT | 700 |
| TGCATGGTAG | TTCTCATTAT | CGTAACATTG | TCAGGAAGCG | ATGCATCTAA | 750 |
| GGAAGGATCG | GCCATCGCTG | TAGTAATTGG | TTCATGTTGT | GCTTTACGAA | 800 |
| TTAAGGCATC | CAAATCGCCA | TCCGTACCTT | CCACTTCCGG | ACTTCGTGAC | 850 |
| AATGTCGGTT | CTGTGGCATG | AATCAAATGT | ACACCAGTTG | AATCGTGCAA | 900 |
| ACCTTTTGTG | AGGCTTTCTG | AGAAATCATG | AGCATGAGCA | TTGGCTGTGA | 950 |
| TCTGATTATC | TTCACCTTCA | TCTTCGGAAT | CGGAAAACAT | GGTTTCATTC | 1000 |
| ATTGCTTCGG | GATTCTGAGG | TTTATATCTT | TCTTCAGTAA | CGGTTGTGGT | 1050 |
| CTCCGTTATC | ACAGTAGTCT | CGGTAATTGT | TTTAAGCGCT | TCAACCACGG | 1100 |
| ATACATACCC | TAGACGTTCA | GCAATCGATA | ATGGAGTTTG | TCCTGTCGAT | 1150 |
| GTATGAACAT | TTGGACTTGC | ACCATGTTCC | AACAAGTAAC | GTACAACACT | 1200 |
| GTTATGCCCT | TGCTGAGCAG | CTTGATG | | | 1227 |

(2) INFORMATION FOR SEQ ID NO:19:

(i) SEQUENCE CHARACTERISTICS:
        (A) LENGTH: 573 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..573

(xi) SEQUENCE DESCRIPTION: SEQ ID NO:19:

| | | | | | | | | | | | | | |
|---|---|---|---|---|---|---|---|---|---|---|---|---|---|
| AAT | AAC | GAC | AAG | GTA | GCA | TTG | TTA | CTT | CTA | GAA | AAT | GGT | GCT | 42 |
| Asn | Asn | Asp | Lys | Val | Ala | Leu | Leu | Leu | Leu | Glu | Asn | Gly | Ala | |
| 1 | | | | 5 | | | | | 10 | | | | | |
| TCT | GCA | CAT | GCC | GCT | GCC | AAG | AAT | GGG | TAC | ACT | CCT | TTA | CAT | 84 |
| Ser | Ala | His | Ala | Ala | Ala | Lys | Asn | Gly | Tyr | Thr | Pro | Leu | His | |
| 15 | | | | | 20 | | | | | 25 | | | | |
| ATT | GCC | GCG | AAG | AAG | AAT | CAG | ATG | GAT | ATT | GCT | AGC | ACT | CTC | 126 |
| Ile | Ala | Ala | Lys | Lys | Asn | Gln | Met | Asp | Ile | Ala | Ser | Thr | Leu | |
| | 30 | | | | | 35 | | | | | 40 | | | |
| CTT | CAT | TAT | AAG | GCA | AAT | GCG | AAT | GCT | GAA | AGC | AAA | GCT | GGC | 168 |
| Leu | His | Tyr | Lys | Ala | Asn | Ala | Asn | Ala | Glu | Ser | Lys | Ala | Gly | |
| | | 45 | | | | | 50 | | | | | 55 | | |
| TTT | ACA | CCA | CTT | CAT | CTT | GCC | GCC | CAG | GAG | GGC | CAT | CGC | GAA | 210 |
| Phe | Thr | Pro | Leu | His | Leu | Ala | Ala | Gln | Glu | Gly | His | Arg | Glu | |
| | | | 60 | | | | | 65 | | | | | 70 | |
| ATG | GCT | GCG | TTA | TTA | ATT | GAA | AAT | GGA | GCA | AAA | GTT | GGA | GCT | 252 |
| Met | Ala | Ala | Leu | Leu | Ile | Glu | Asn | Gly | Ala | Lys | Val | Gly | Ala | |
| | | | | 75 | | | | | 80 | | | | | |
| CAG | GCA | AGG | AAT | GGC | TTG | ACA | CCA | ATG | CAT | TTA | TGT | GCA | CAG | 294 |
| Gln | Ala | Arg | Asn | Gly | Leu | Thr | Pro | Met | His | Leu | Cys | Ala | Gln | |
| 85 | | | | | 90 | | | | | 95 | | | | |
| GAG | GAT | CGT | GTG | AGC | GTA | GCA | GAA | GAA | CTA | GTG | AAA | GAA | AAC | 336 |
| Glu | Asp | Arg | Val | Ser | Val | Ala | Glu | Glu | Leu | Val | Lys | Glu | Asn | |
| | 100 | | | | | 105 | | | | | 110 | | | |
| GCA | GCC | ATT | GAT | CCC | AAA | ACG | AAA | GCA | GGA | TAT | ACG | CCG | TTA | 378 |

| | | | | | | | | | | | | |
|---|---|---|---|---|---|---|---|---|---|---|---|---|
| Ala | Ala | Ile | Asp | Pro | Lys | Thr | Lys | Ala | Gly | Tyr | Thr | Pro | Leu |
| | | 115 | | | | 120 | | | | | | 125 | |

| | | | | | | | | | | | | | |
|---|---|---|---|---|---|---|---|---|---|---|---|---|---|
| CAT | GTT | GCT | TGC | CAT | TTT | GGA | CAA | ATA | AAC | ATG | GTC | CGT | TTC | 420 |
| His | Val | Ala | Cys | His | Phe | Gly | Gln | Ile | Asn | Met | Val | Arg | Phe | |
| | | | 130 | | | | | 135 | | | | | 140 | |

| | | | | | | | | | | | | |
|---|---|---|---|---|---|---|---|---|---|---|---|---|
| TTG | ATT | GAG | CAT | GGC | GCA | CGA | GTT | TCA | GTT | ATT | ACT | CGT | GCT | 462 |
| Leu | Ile | Glu | His | Gly | Ala | Arg | Val | Ser | Val | Ile | Thr | Arg | Ala |
| | | | | 145 | | | | | 150 | | | | |

| | | | | | | | | | | | | |
|---|---|---|---|---|---|---|---|---|---|---|---|---|
| TCC | TAT | ACT | CCT | CTG | CAT | CAA | GCT | GCT | CAG | CAA | GGG | CAT | AAC | 504 |
| Ser | Tyr | Thr | Pro | Leu | His | Gln | Ala | Ala | Gln | Gln | Gly | His | Asn |
| 155 | | | | | 160 | | | | | 165 | | | |

| | | | | | | | | | | | | |
|---|---|---|---|---|---|---|---|---|---|---|---|---|
| AGT | GTT | GTA | CGT | TAC | TTG | TTG | GAA | CAT | GGT | GCA | AGT | CCA | AAT | 546 |
| Ser | Val | Val | Arg | Tyr | Leu | Leu | Glu | His | Gly | Ala | Ser | Pro | Asn |
| | 170 | | | | | 175 | | | | | 180 | | |

| | | | | | | | |
|---|---|---|---|---|---|---|---|
| GTT | CAT | ACA | TCG | ACA | GGA | CAA | ACT | CCA | 573 |
| Val | His | Thr | Ser | Thr | Gly | Gln | Thr | Pro | |
| | | 185 | | | | | 190 | | |

( 2 ) INFORMATION FOR SEQ ID NO:20:

( i ) SEQUENCE CHARACTERISTICS:
        ( A ) LENGTH: 191 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

| | | | | | | | | | | | |
|---|---|---|---|---|---|---|---|---|---|---|---|
| Asn | Asn | Asp | Lys | Val | Ala | Leu | Leu | Leu | Glu | Asn | Gly | Ala |
| 1 | | | | 5 | | | | | 10 | | | |

| | | | | | | | | | | | |
|---|---|---|---|---|---|---|---|---|---|---|---|
| Ser | Ala | His | Ala | Ala | Ala | Lys | Asn | Gly | Tyr | Thr | Pro | Leu | His |
| 15 | | | | | 20 | | | | | 25 | | | |

| | | | | | | | | | | | |
|---|---|---|---|---|---|---|---|---|---|---|---|
| Ile | Ala | Ala | Lys | Lys | Asn | Gln | Met | Asp | Ile | Ala | Ser | Thr | Leu |
| | 30 | | | | | 35 | | | | | 40 | | |

| | | | | | | | | | | | |
|---|---|---|---|---|---|---|---|---|---|---|---|
| Leu | His | Tyr | Lys | Ala | Asn | Ala | Asn | Ala | Glu | Ser | Lys | Ala | Gly |
| | | 45 | | | | | 50 | | | | | 55 | |

| | | | | | | | | | | | |
|---|---|---|---|---|---|---|---|---|---|---|---|
| Phe | Thr | Pro | Leu | His | Leu | Ala | Ala | Gln | Glu | Gly | His | Arg | Glu |
| | | | 60 | | | | | 65 | | | | | 70 |

| | | | | | | | | | | | |
|---|---|---|---|---|---|---|---|---|---|---|---|
| Met | Ala | Ala | Leu | Leu | Ile | Glu | Asn | Gly | Ala | Lys | Val | Gly | Ala |
| | | | | 75 | | | | | 80 | | | | |

| | | | | | | | | | | | |
|---|---|---|---|---|---|---|---|---|---|---|---|
| Gln | Ala | Arg | Asn | Gly | Leu | Thr | Pro | Met | His | Leu | Cys | Ala | Gln |
| 85 | | | | | 90 | | | | | 95 | | | |

| | | | | | | | | | | | |
|---|---|---|---|---|---|---|---|---|---|---|---|
| Glu | Asp | Arg | Val | Ser | Val | Ala | Glu | Glu | Leu | Val | Lys | Glu | Asn |
| | 100 | | | | | 105 | | | | | 110 | | |

| | | | | | | | | | | | |
|---|---|---|---|---|---|---|---|---|---|---|---|
| Ala | Ala | Ile | Asp | Pro | Lys | Thr | Lys | Ala | Gly | Tyr | Thr | Pro | Leu |
| | | 115 | | | | 120 | | | | | | 125 | |

| | | | | | | | | | | | |
|---|---|---|---|---|---|---|---|---|---|---|---|
| His | Val | Ala | Cys | His | Phe | Gly | Gln | Ile | Asn | Met | Val | Arg | Phe |
| | | | 130 | | | | | 135 | | | | | 140 |

| | | | | | | | | | | | |
|---|---|---|---|---|---|---|---|---|---|---|---|
| Leu | Ile | Glu | His | Gly | Ala | Arg | Val | Ser | Val | Ile | Thr | Arg | Ala |
| | | | | 145 | | | | | 150 | | | | |

| | | | | | | | | | | | |
|---|---|---|---|---|---|---|---|---|---|---|---|
| Ser | Tyr | Thr | Pro | Leu | His | Gln | Ala | Ala | Gln | Gln | Gly | His | Asn |
| 155 | | | | | 160 | | | | | 165 | | | |

| | | | | | | | | | | | |
|---|---|---|---|---|---|---|---|---|---|---|---|
| Ser | Val | Val | Arg | Tyr | Leu | Leu | Glu | His | Gly | Ala | Ser | Pro | Asn |
| | 170 | | | | | 175 | | | | | 180 | | |

| | | | | | | | |
|---|---|---|---|---|---|---|---|
| Val | His | Thr | Ser | Thr | Gly | Gln | Thr | Pro |
| | | 185 | | | | | 190 | |

( 2 ) INFORMATION FOR SEQ ID NO:21:

( i ) SEQUENCE CHARACTERISTICS:
    ( A ) LENGTH: 573 nucleotides
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:21:

| | | | | | |
|---|---|---|---|---|---|
| TGGAGTTTGT | CCTGTCGATG | TATGAACATT | TGGACTTGCA | CCATGTTCCA | 50 |
| ACAAGTAACG | TACAACACTG | TTATGCCCTT | GCTGAGCAGC | TTGATGCAGA | 100 |
| GGAGTATAGG | AAGCACGAGT | AATAACTGAA | ACTCGTGCGC | CATGCTCAAT | 150 |
| CAAGAAACGG | ACCATGTTTA | TTTGTCCAAA | ATGGCAAGCA | ACATGTAACG | 200 |
| GCGTATATCC | TGCTTTCGTT | TTGGGATCAA | TGGCTGCGTT | TTCTTTCACT | 250 |
| AGTTCTTCTG | CTACGCTCAC | ACGATCCTCC | TGTGCACATA | AATGCATTGG | 300 |
| TGTCAAGCCA | TTCCTTGCCT | GAGCTCCAAC | TTTTGCTCCA | TTTTCAATTA | 350 |
| ATAACGCAGC | CATTTCGCGA | TGGCCCTCCT | GGGCGGCAAG | ATGAAGTGGT | 400 |
| GTAAAGCCAG | CTTTGCTTTC | AGCATTCGCA | TTTGCCTTAT | AATGAAGGAG | 450 |
| AGTGCTAGCA | ATATCCATCT | GATTCTTCTT | CGCGGCAATA | TGTAAAGGAG | 500 |
| TGTACCCATT | CTTGGCAGCG | GCATGTGCAG | AAGCACCATT | TTCTAGAAGT | 550 |
| AACAATGCTA | CCTTGTCGTT | ATT | | | 573 |

( 2 ) INFORMATION FOR SEQ ID NO:22:

( i ) SEQUENCE CHARACTERISTICS:
        ( A ) LENGTH: 911 nucleotides
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..909

( x i ) SEQUENCE DESCRIPTION: SEQ ID NO:22:

| | | | | | | | | | | | | | | |
|---|---|---|---|---|---|---|---|---|---|---|---|---|---|---|
| GTG | GAT | GAT | GTT | ACT | GTT | GAC | TAT | CTC | ACT | CCT | CTT | CAT | GTG | 42 |
| Val | Asp | Asp | Val | Thr | Val | Asp | Tyr | Leu | Thr | Pro | Leu | His | Val | |
| 1 | | | | 5 | | | | | 10 | | | | | |
| GCT | GCT | CAT | TGC | GGA | CAT | GTC | CGT | GTC | GCT | AAA | CTT | TTG | CTG | 84 |
| Ala | Ala | His | Cys | Gly | His | Val | Arg | Val | Ala | Lys | Leu | Leu | Leu | |
| 15 | | | | | 20 | | | | | 25 | | | | |
| GAT | CGT | AAT | GCT | GAC | CCG | AAT | GCT | CGA | GCT | CTC | AAT | GGC | TTC | 126 |
| Asp | Arg | Asn | Ala | Asp | Pro | Asn | Ala | Arg | Ala | Leu | Asn | Gly | Phe | |
| | 30 | | | | | 35 | | | | | 40 | | | |
| ACA | CCG | CTG | CAT | ATC | GCT | TGC | AAA | AAA | AAT | CGC | ATT | AAA | ATT | 168 |
| Thr | Pro | Leu | His | Ile | Ala | Cys | Lys | Lys | Asn | Arg | Ile | Lys | Ile | |
| | | 45 | | | | | 50 | | | | | 55 | | |
| GTC | GAA | CTG | CTA | CTG | AAA | TAC | CAC | GCT | GCA | ATC | GAA | GCA | ACT | 210 |
| Val | Glu | Leu | Leu | Leu | Lys | Tyr | His | Ala | Ala | Ile | Glu | Ala | Thr | |
| | | | | 60 | | | | | 65 | | | | | 70 |
| ACT | GAA | TCC | GGT | CTC | TCA | CCG | CTG | CAT | GTC | GCT | GCT | TTT | ATG | 252 |
| Thr | Glu | Ser | Gly | Leu | Ser | Pro | Leu | His | Val | Ala | Ala | Phe | Met | |
| | | | | 75 | | | | | 80 | | | | | |
| GGT | GCT | ATA | AAC | ATT | GTC | ATC | TAT | TTA | CTA | CAA | CAA | GGT | GCT | 294 |
| Gly | Ala | Ile | Asn | Ile | Val | Ile | Tyr | Leu | Leu | Gln | Gln | Gly | Ala | |
| 85 | | | | | 90 | | | | | 95 | | | | |
| AAT | GCA | GAT | GTG | GCT | ACA | GTA | CGC | GGT | GAA | ACG | CCT | CTT | CAT | 336 |

```
                Asn Ala Asp Val Ala Thr Val Arg Gly Glu Thr Pro Leu His
                    100             105             110

TTA GCT GCA CGA GCA AAC CAA ACG GAC ATT GTT CGT GTT TTG                 378
Leu Ala Ala Arg Ala Asn Gln Thr Asp Ile Val Arg Val Leu
            115             120             125

GTG CGT AAT GGA GCA CAG GTG GAT GCT GCT GCT CGT GAA CTA                 420
Val Arg Asn Gly Ala Gln Val Asp Ala Ala Ala Arg Glu Leu
            130             135             140

CAA ACT CCA CTG CAC ATT GCA TCA CGT CTT GGT AAT ACC GAC                 462
Gln Thr Pro Leu His Ile Ala Ser Arg Leu Gly Asn Thr Asp
            145             150

ATC GTC ATT TTG TTG CTG CAG GCT AAT GCA TCA CCA AAT GCT                 504
Ile Val Ile Leu Leu Leu Gln Ala Asn Ala Ser Pro Asn Ala
155             160             165

GCC ACA AGA GAT CTT TAT ACT CCT CTT CAT ATT GCT GCC AAG                 546
Ala Thr Arg Asp Leu Tyr Thr Pro Leu His Ile Ala Ala Lys
        170             175             180

GAG GGG CAA GAG GAA GTG GCA GCA ATA TTG ATG GAT CAT GGA                 588
Glu Gly Gln Glu Glu Val Ala Ala Ile Leu Met Asp His Gly
        185             190             195

ACC GAC AAG ACA CTG CTC ACG AAA AAG GGT TTT ACG CCG TTG                 630
Thr Asp Lys Thr Leu Leu Thr Lys Lys Gly Phe Thr Pro Leu
        200             205             210

CAT TTA GCT GCT AAG TAT GGC AAT TTG CCG GTC GCG AAA TCA                 672
His Leu Ala Ala Lys Tyr Gly Asn Leu Pro Val Ala Lys Ser
            215             220

TTG CTA GAA CGA GGA ACA CCG GTT GAC ATT GAA GGC AAG AAT                 714
Leu Leu Glu Arg Gly Thr Pro Val Asp Ile Glu Gly Lys Asn
225             230             235

CAG GTA ACA CCT CTG CAT GTA GCG GCA CAT TAC AAT AAC GAC                 756
Gln Val Thr Pro Leu His Val Ala Ala His Tyr Asn Asn Asp
    240             245             250

AAG GTA GCA TTG TTA CTT CTA GAA AAT GGT GCT TCT GCA CAT                 798
Lys Val Ala Leu Leu Leu Leu Glu Asn Gly Ala Ser Ala His
            255             260             265

GCC GCT GCC AAG AAT GGG TAC ACT CCT TTA CAT ATT GCC GCG                 840
Ala Ala Ala Lys Asn Gly Tyr Thr Pro Leu His Ile Ala Ala
            270             275             280

AAG AAG AAT CAG ATG GAT ATT GCT AGC ACT CTC CTT CAT TAT                 882
Lys Lys Asn Gln Met Asp Ile Ala Ser Thr Leu Leu His Tyr
                285             290

AAG GCA AAT GCG AAT GCT GAA AGC AAA GC                                  911
Lys Ala Asn Ala Asn Ala Glu Ser Lys
295             300
```

( 2 ) INFORMATION FOR SEQ ID NO:23:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

```
Val Asp Asp Val Thr Val Asp Tyr Leu Thr Pro Leu His Val
 1               5                  10

Ala Ala His Cys Gly His Val Arg Val Ala Lys Leu Leu Leu
15              20                  25

Asp Arg Asn Ala Asp Pro Asn Ala Arg Ala Leu Asn Gly Phe
    30              35                  40
```

| | | | | | | | | | | | | | |
|---|---|---|---|---|---|---|---|---|---|---|---|---|---|
|Thr|Pro|Leu|His|Ile|Ala|Cys|Lys|Lys|Asn|Arg|Ile|Lys|Ile|
| | | |45| | | |50| | | | |55| |
|Val|Glu|Leu|Leu|Leu|Lys|Tyr|His|Ala|Ala|Ile|Glu|Ala|Thr|
| | | |60| | | |65| | | | | |70|
|Thr|Glu|Ser|Gly|Leu|Ser|Pro|Leu|His|Val|Ala|Ala|Phe|Met|
| | | | |75| | | | |80| | | | |
|Gly|Ala|Ile|Asn|Ile|Val|Ile|Tyr|Leu|Leu|Gln|Gln|Gly|Ala|
|85| | | | |90| | | | |95| | | |
|Asn|Ala|Asp|Val|Ala|Thr|Val|Arg|Gly|Glu|Thr|Pro|Leu|His|
| |100| | | | |105| | | |110| | | |
|Leu|Ala|Ala|Arg|Ala|Asn|Gln|Thr|Asp|Ile|Val|Arg|Val|Leu|
| | | |115| | | |120| | | | |125| |
|Val|Arg|Asn|Gly|Ala|Gln|Val|Asp|Ala|Ala|Ala|Arg|Glu|Leu|
| | |130| | | | |135| | | | | |140|
|Gln|Thr|Pro|Leu|His|Ile|Ala|Ser|Arg|Leu|Gly|Asn|Thr|Asp|
| | | | |145| | | |150| | | | | |
|Ile|Val|Ile|Leu|Leu|Leu|Gln|Ala|Asn|Ala|Ser|Pro|Asn|Ala|
|155| | | | |160| | | |165| | | | |
|Ala|Thr|Arg|Asp|Leu|Tyr|Thr|Pro|Leu|His|Ile|Ala|Ala|Lys|
| |170| | | | |175| | | |180| | | |
|Glu|Gly|Gln|Glu|Glu|Val|Ala|Ala|Ile|Leu|Met|Asp|His|Gly|
| | |185| | | | |190| | | | |195| |
|Thr|Asp|Lys|Thr|Leu|Leu|Thr|Lys|Lys|Gly|Phe|Thr|Pro|Leu|
| | | |200| | | |205| | | | | |210|
|His|Leu|Ala|Ala|Lys|Tyr|Gly|Asn|Leu|Pro|Val|Ala|Lys|Ser|
| | | | |215| | | | |220| | | | |
|Leu|Leu|Glu|Arg|Gly|Thr|Pro|Val|Asp|Ile|Glu|Gly|Lys|Asn|
|225| | | | |230| | | |235| | | | |
|Gln|Val|Thr|Pro|Leu|His|Val|Ala|Ala|His|Tyr|Asn|Asn|Asp|
| |240| | | | |245| | | |250| | | |
|Lys|Val|Ala|Leu|Leu|Leu|Leu|Glu|Asn|Gly|Ala|Ser|Ala|His|
| | |255| | | | |260| | | |265| | |
|Ala|Ala|Ala|Lys|Asn|Gly|Tyr|Thr|Pro|Leu|His|Ile|Ala|Ala|
| | | |270| | | |275| | | | | |280|
|Lys|Lys|Asn|Gln|Met|Asp|Ile|Ala|Ser|Thr|Leu|Leu|His|Tyr|
| | | | |285| | | |290| | | | | |
|Lys|Ala|Asn|Ala|Asn|Ala|Glu|Ser|Lys| | | | | |
|295| | | |300| | | | | | | | | |

( 2 ) INFORMATION FOR SEQ ID NO:24:

( i ) SEQUENCE CHARACTERISTICS:
        ( A ) LENGTH: 911 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

| | | | | | |
|---|---|---|---|---|---|
|GCTTTGCTTT|CAGCATTCGC|ATTTGCCTTA|TAATGAAGGA|GAGTGCTAGC|50|
|AATATCCATC|TGATTCTTCT|TCGCGGCAAT|ATGTAAAGGA|GTGTACCCAT|100|
|TCTTGGCAGC|GGCATGTGCA|GAAGCACCAT|TTTCTAGAAG|TAACAATGCT|150|
|ACCTTGTCGT|TATTGTAATG|TGCCGCTACA|TGCAGAGGTG|TTACCTGATT|200|
|CTTGCCTTCA|ATGTCAACCG|GTGTTCCTCG|TTCTAGCAAT|GATTTCGCGA|250|

```
CCGGCAAATT   GCCATACTTA   GCAGCTAAAT   GCAACGGCGT   AAAACCCTTT          300

TTCGTGAGCA   GTGTCTTGTC   GGTTCCATGA   TCCATCAATA   TTGCTGCCAC          350

TTCCTCTTGC   CCCTCCTTGG   CAGCAATATG   AAGAGGAGTA   TAAAGATCTC          400

TTGTGGCAGC   ATTTGGTGAT   GCATTAGCCT   GCAGCAACAA   AATGACGATG          450

TCGGTATTAC   CAAGACGTGA   TGCAATGTGC   AGTGGAGTTT   GTAGTTCACG          500

AGCAGCAGCA   TCCACCTGTG   CTCCATTACG   CACCAAAACA   CGAACAATGT          550

CCGTTTGGTT   TGCTCGTGCA   GCTAAATGAA   GAGGCGTTTC   ACCGCGTACT          600

GTAGCCACAT   CTGCATTAGC   ACCTTGTTGT   AGTAAATAGA   TGACAATGTT          650

TATAGCACCC   ATAAAAGCAG   CGACATGCAG   CGGTGAGAGA   CCGGATTCAG          700

TAGTTGCTTC   GATTGCAGCG   TGGTATTTCA   GTAGCAGTTC   GACAATTTTA          750

ATGCGATTTT   TTTTGCAAGC   GATATGCAGC   GGTGTGAAGC   CATTGAGAGC          800

TCGAGCATTC   GGGTCAGCAT   TACGATCCAG   CAAAAGTTTA   GCGACACGGA          850

CATGTCCGCA   ATGAGCAGCC   ACATGAAGAG   GAGTGAGATA   GTCAACAGTA          900

ACATCATCCA   C                                                         911
```

( 2 ) INFORMATION FOR SEQ ID NO:25:

( i ) SEQUENCE CHARACTERISTICS:
        ( A ) LENGTH: 909 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

```
GTGGATGATG   TTACTGTTGA   CTATCTCACT   CCTCTTCATG   TGGCTGCTCA           50

TTGCGGACAT   GTCCGTGTCG   CTAAACTTTT   GCTGGATCGT   AATGCTGACC          100

CGAATGCTCG   AGCTCTCAAT   GGCTTCACAC   CGCTGCATAT   CGCTTGCAAA          150

AAAAATCGCA   TTAAAATTGT   CGAACTGCTA   CTGAAATACC   ACGCTGCAAT          200

CGAAGCAACT   ACTGAATCCG   GTCTCTCACC   GCTGCATGTC   GCTGCTTTTA          250

TGGGTGCTAT   AAACATTGTC   ATCTATTTAC   TACAACAAGG   TGCTAATGCA          300

GATGTGGCTA   CAGTACGCGG   TGAAACGCCT   CTTCATTTAG   CTGCACGAGC          350

AAACCAAACG   GACATTGTTC   GTGTTTTGGT   GCGTAATGGA   GCACAGGTGG          400

ATGCTGCTGC   TCGTGAACTA   CAAACTCCAC   TGCACATTGC   ATCACGTCTT          450

GGTAATACCG   ACATCGTCAT   TTGTTGCTG    CAGGCTAATG   CATCACCAAA          500

TGCTGCCACA   AGAGATCTTT   ATACTCCTCT   TCATATTGCT   GCCAAGGAGG          550

GGCAAGAGGA   AGTGGCAGCA   ATATTGATGG   ATCATGGAAC   CGACAAGACA          600

CTGCTCACGA   AAAAGGGTTT   TACGCCGTTG   CATTTAGCTG   CTAAGTATGG          650

CAATTTGCCG   GTCGCGAAAT   CATTGCTAGA   ACGAGGAACA   CCGGTTGACA          700

TTGAAGGCAA   GAATCAGGTA   ACACCTCTGC   ATGTAGCGGC   ACATTACAAT          750

AACGACAAGG   TAGCATTGTT   ACTTCTAGAA   AATGGTGCTT   CTGCACATGC          800

CGCTGCCAAG   AATGGGTACA   CTCCTTTACA   TATTGCCGCG   AAGAAGAATC          850

AGATGGATAT   TGCTAGCACT   CTCCTTCATT   ATAAGGCAAA   TGCGAATGCT          900

GAAAGCAAA                                                              909
```

( 2 ) INFORMATION FOR SEQ ID NO:26:

( i ) SEQUENCE CHARACTERISTICS:
　　　　　　　( A ) LENGTH: 909 nucleotides
　　　　　　　( B ) TYPE: nucleic acid
　　　　　　　( C ) STRANDEDNESS: single
　　　　　　　( D ) TOPOLOGY: linear ( i i ) MOLECULE TYPE: cDNA ( x i ) SEQUENCE DESCRIPTION: SEQ ID NO:26:

| | | | | | |
|---|---|---|---|---|---|
| TTTGCTTTCA | GCATTCGCAT | TTGCCTTATA | ATGAAGGAGA | GTGCTAGCAA | 50 |
| TATCCATCTG | ATTCTTCTTC | GCGGCAATAT | GTAAAGGAGT | GTACCCATTC | 100 |
| TTGGCAGCGG | CATGTGCAGA | AGCACCATTT | TCTAGAAGTA | ACAATGCTAC | 150 |
| CTTGTCGTTA | TTGTAATGTG | CCGCTACATG | CAGAGGTGTT | ACCTGATTCT | 200 |
| TGCCTTCAAT | GTCAACCGGT | GTTCCTCGTT | CTAGCAATGA | TTTCGCGACC | 250 |
| GGCAAATTGC | CATACTTAGC | AGCTAAATGC | AACGGCGTAA | AACCCTTTTT | 300 |
| CGTGAGCAGT | GTCTTGTCGG | TTCCATGATC | CATCAATATT | GCTGCCACTT | 350 |
| CCTCTTGCCC | CTCCTTGGCA | GCAATATGAA | GAGGAGTATA | AAGATCTCTT | 400 |
| GTGGCAGCAT | TTGGTGATGC | ATTAGCCTGC | AGCAACAAAA | TGACGATGTC | 450 |
| GGTATTACCA | AGACGTGATG | CAATGTGCAG | TGGAGTTTGT | AGTTCACGAG | 500 |
| CAGCAGCATC | CACCTGTGCT | CCATTACGCA | CCAAAACACG | AACAATGTCC | 550 |
| GTTTGGTTTG | CTCGTGCAGC | TAAATGAAGA | GGCGTTTCAC | CGCGTACTGT | 600 |
| AGCCACATCT | GCATTAGCAC | CTTGTTGTAG | TAAATAGATG | ACAATGTTTA | 650 |
| TAGCACCCAT | AAAAGCAGCG | ACATGCAGCG | GTGAGAGACC | GGATTCAGTA | 700 |
| GTTGCTTCGA | TTGCAGCGTG | GTATTTCAGT | AGCAGTTCGA | CAATTTTAAT | 750 |
| GCGATTTTTT | TTGCAAGCGA | TATGCAGCGG | TGTGAAGCCA | TTGAGAGCTC | 800 |
| GAGCATTCGG | GTCAGCATTA | CGATCCAGCA | AAAGTTTAGC | GACACGGACA | 850 |
| TGTCCGCAAT | GAGCAGCCAC | ATGAAGAGGA | GTGAGATAGT | CAACAGTAAC | 900 |
| ATCATCCAC | | | | | 909 |

( 2 ) INFORMATION FOR SEQ ID NO:27:

( i ) SEQUENCE CHARACTERISTICS:
　　　　　　　( A ) LENGTH: 1096 nucleotides
　　　　　　　( B ) TYPE: nucleic acid
　　　　　　　( C ) STRANDEDNESS: single
　　　　　　　( D ) TOPOLOGY: linear ( i i ) MOLECULE TYPE: cDNA ( i x ) FEATURE:
　　　　　　　( A ) NAME/KEY: CDS
　　　　　　　( B ) LOCATION: 51..1094

( x i ) SEQUENCE DESCRIPTION: SEQ ID NO:27:

```
GGTTTAATTA  CCCAAGTTTG  AGGCGGCTGA  CTGATATAAC  TCAACTATTG                 50

ATG  AGT  AAT  CCT  ATA  GTC  GAG  GGA  AGT  GGC  TGG  CCC  GCA  GAA       92
Met  Ser  Asn  Pro  Ile  Val  Glu  Gly  Ser  Gly  Trp  Pro  Ala  Glu
 1              5                        10

CCA  AAA  GAT  TCA  CAA  CAT  CAA  CAA  CAA  ATT  CCT  GAT  GAT  AAC      134
Pro  Lys  Asp  Ser  Gln  His  Gln  Gln  Gln  Ile  Pro  Asp  Asp  Asn
        15                  20                       25

AGT  CAA  CAT  TCC  AAC  AAA  GGT  GAG  AGC  AGT  GCA  AGT  TTT  TTA      176
Ser  Gln  His  Ser  Asn  Lys  Gly  Glu  Ser  Ser  Ala  Ser  Phe  Leu
    30                       35                      40
```

| | | | | | | | | | | | | | |
|---|---|---|---|---|---|---|---|---|---|---|---|---|---|
| CGA | GCA | GCA | AGA | GCT | GGA | AAT | TTG | GAT | CGT | GTA | CTT | GAA | CTA | 218 |
| Arg | Ala | Ala | Arg | Ala | Gly | Asn | Leu | Asp | Arg | Val | Leu | Glu | Leu | |
| | | 45 | | | | 50 | | | | | 55 | | | |
| CTT | CGT | TCG | GGC | ACC | GAT | ATC | AAC | ACA | TGC | AAT | GCG | AAT | GGC | 260 |
| Leu | Arg | Ser | Gly | Thr | Asp | Ile | Asn | Thr | Cys | Asn | Ala | Asn | Gly | |
| | | | 60 | | | | | 65 | | | | | 70 | |
| CTT | AAT | GCA | TTG | CAT | CTG | GCC | TCC | AAA | GAA | GGT | CAT | CAT | GAA | 302 |
| Leu | Asn | Ala | Leu | His | Leu | Ala | Ser | Lys | Glu | Gly | His | His | Glu | |
| | | | | 75 | | | | | 80 | | | | | |
| GTG | GTC | CGC | GAA | CTT | CTG | AAA | AGA | AAA | GCA | GAT | GTT | GAT | GCT | 344 |
| Val | Val | Arg | Glu | Leu | Leu | Lys | Arg | Lys | Ala | Asp | Val | Asp | Ala | |
| 85 | | | | | 90 | | | | | 95 | | | | |
| GCC | ACT | AGA | AAG | GGT | AAC | ACA | GCG | TTA | CAT | ATA | GCA | TCA | TTG | 386 |
| Ala | Thr | Arg | Lys | Gly | Asn | Thr | Ala | Leu | His | Ile | Ala | Ser | Leu | |
| | 100 | | | | | 105 | | | | | 110 | | | |
| GCA | GGA | CAA | GAA | CTA | ATC | GTC | ACA | GTA | CTT | GTT | GAA | AAT | GGT | 428 |
| Ala | Gly | Gln | Glu | Leu | Ile | Val | Thr | Val | Leu | Val | Glu | Asn | Gly | |
| | | | 115 | | | | | 120 | | | | | 125 | |
| GCT | AAT | GTT | AAC | GTA | CAA | TCA | CTA | AAC | GGT | TTT | ACA | CCA | CTT | 470 |
| Ala | Asn | Val | Asn | Val | Gln | Ser | Leu | Asn | Gly | Phe | Thr | Pro | Leu | |
| | | | 130 | | | | | 135 | | | | | 140 | |
| TAC | ATG | GCT | GCA | CAA | GAA | AAT | CAC | GAA | TCT | GTT | GTA | CGC | TAT | 512 |
| Tyr | Met | Ala | Ala | Gln | Glu | Asn | His | Glu | Ser | Val | Val | Arg | Tyr | |
| | | | | 145 | | | | | 150 | | | | | |
| CTT | CTT | GCC | CAC | AAT | GCC | AAT | CAA | GCT | TTA | AGT | ACA | GAA | GAC | 554 |
| Leu | Leu | Ala | His | Asn | Ala | Asn | Gln | Ala | Leu | Ser | Thr | Glu | Asp | |
| 155 | | | | | 160 | | | | | 165 | | | | |
| GGT | TTT | ACG | CCA | CTG | GCA | GTT | GCC | TTG | CAA | CAA | GGT | CAC | GAT | 596 |
| Gly | Phe | Thr | Pro | Leu | Ala | Val | Ala | Leu | Gln | Gln | Gly | His | Asp | |
| | 170 | | | | | 175 | | | | | 180 | | | |
| CGT | GTG | GTC | GCT | GTT | TTG | CTT | GAA | AAT | GAC | ACG | CGC | GGG | AAA | 638 |
| Arg | Val | Val | Ala | Val | Leu | Leu | Glu | Asn | Asp | Thr | Arg | Gly | Lys | |
| | | 185 | | | | | 190 | | | | | 195 | | |
| GTG | CGC | TTG | CCA | GCA | CTG | CAT | ATT | GCT | GCT | AAA | AAA | GAT | GAT | 680 |
| Val | Arg | Leu | Pro | Ala | Leu | His | Ile | Ala | Ala | Lys | Lys | Asp | Asp | |
| | | | 200 | | | | | 205 | | | | | 210 | |
| ACG | AAA | GCA | GCT | ACG | CTA | TTA | CTT | CAA | AAT | GAG | CAT | AAC | TCG | 722 |
| Thr | Lys | Ala | Ala | Thr | Leu | Leu | Leu | Gln | Asn | Glu | His | Asn | Ser | |
| | | | | 215 | | | | | 220 | | | | | |
| GAT | GTG | ACT | TCG | AAA | AGC | GGC | TTT | ACT | CCG | CTT | CAT | ATC | GCC | 764 |
| Asp | Val | Thr | Ser | Lys | Ser | Gly | Phe | Thr | Pro | Leu | His | Ile | Ala | |
| 225 | | | | | 230 | | | | | 235 | | | | |
| GCT | CAC | TAT | GGA | AAT | GAG | AAC | GTA | GCA | CAA | CTG | CTA | CTC | GAA | 806 |
| Ala | His | Tyr | Gly | Asn | Glu | Asn | Val | Ala | Gln | Leu | Leu | Leu | Glu | |
| | | 240 | | | | | 245 | | | | | 250 | | |
| AAG | GGA | GCC | AAT | GTG | AAT | TAC | CAA | GCG | AGA | CAT | AAC | ATA | AGT | 848 |
| Lys | Gly | Ala | Asn | Val | Asn | Tyr | Gln | Ala | Arg | His | Asn | Ile | Ser | |
| | | | 255 | | | | | 260 | | | | | 265 | |
| CCG | TTA | CAC | GTT | GCA | ACA | AAA | TGG | GGT | CGT | ACA | AAC | ATG | GTT | 890 |
| Pro | Leu | His | Val | Ala | Thr | Lys | Trp | Gly | Arg | Thr | Asn | Met | Val | |
| | | | | 270 | | | | | 275 | | | | | 280 |
| TCG | TTA | TTG | TTG | GCT | CAT | GGG | GCC | GTA | ATT | GAC | TGT | CGC | ACA | 932 |
| Ser | Leu | Leu | Leu | Ala | His | Gly | Ala | Val | Ile | Asp | Cys | Arg | Thr | |
| | | | | 285 | | | | | 290 | | | | | |
| CGT | GAT | TTA | CTA | ACA | CCA | TTA | CAC | TGT | GCT | TCT | CGT | TCA | GGT | 974 |
| Arg | Asp | Leu | Leu | Thr | Pro | Leu | His | Cys | Ala | Ser | Arg | Ser | Gly | |
| 295 | | | | | 300 | | | | | 305 | | | | |
| CAT | GAT | CAA | GTT | GTT | GAT | TTG | TTG | CTT | GAA | AAA | GGA | GCT | CCA | 1016 |
| His | Asp | Gln | Val | Val | Asp | Leu | Leu | Leu | Glu | Lys | Gly | Ala | Pro | |
| | | 310 | | | | | 315 | | | | | 320 | | |

```
ATC  AGT  GCT  AAG  ACA  AAA  AAT  GGT  TTG  GCT  CCC  TTA  CAT  ATG                1058
Ile  Ser  Ala  Lys  Thr  Lys  Asn  Gly  Leu  Ala  Pro  Leu  His  Met
          325                      330                      335

GCA  GCA  CAG  GTG  GAT  GAT  GTT  ACT  GTT  GAC  TAT  CTC  AC                       1096
Ala  Ala  Gln  Val  Asp  Asp  Val  Thr  Val  Asp  Tyr  Leu
               340                      345
```

( 2 ) INFORMATION FOR SEQ ID NO:28:

( i ) SEQUENCE CHARACTERISTICS:
        ( A ) LENGTH: 348 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Met  Ser  Asn  Pro  Ile  Val  Glu  Gly  Ser  Gly  Trp  Pro  Ala  Glu
1              5                        10
Pro  Lys  Asp  Ser  Gln  His  Gln  Gln  Ile  Pro  Asp  Asp  Asn
15                       20                  25
Ser  Gln  His  Ser  Asn  Lys  Gly  Glu  Ser  Ser  Ala  Ser  Phe  Leu
          30                  35                       40
Arg  Ala  Ala  Arg  Ala  Gly  Asn  Leu  Asp  Arg  Val  Leu  Glu  Leu
               45                  50                            55
Leu  Arg  Ser  Gly  Thr  Asp  Ile  Asn  Thr  Cys  Asn  Ala  Asn  Gly
                    60                  65                            70
Leu  Asn  Ala  Leu  His  Leu  Ala  Ser  Lys  Glu  Gly  His  His  Glu
                    75                       80
Val  Val  Arg  Glu  Leu  Leu  Lys  Arg  Lys  Ala  Asp  Val  Asp  Ala
85                       90                       95
Ala  Thr  Arg  Lys  Gly  Asn  Thr  Ala  Leu  His  Ile  Ala  Ser  Leu
     100                      105                      110
Ala  Gly  Gln  Glu  Leu  Ile  Val  Thr  Val  Leu  Val  Glu  Asn  Gly
          115                      120                      125
Ala  Asn  Val  Asn  Val  Gln  Ser  Leu  Asn  Gly  Phe  Thr  Pro  Leu
               130                      135                      140
Tyr  Met  Ala  Ala  Gln  Glu  Asn  His  Glu  Ser  Val  Val  Arg  Tyr
               145                      150
Leu  Leu  Ala  His  Asn  Ala  Asn  Gln  Ala  Leu  Ser  Thr  Glu  Asp
155                      160                      165
Gly  Phe  Thr  Pro  Leu  Ala  Val  Ala  Leu  Gln  Gln  Gly  His  Asp
     170                      175                      180
Arg  Val  Val  Ala  Val  Leu  Leu  Glu  Asn  Asp  Thr  Arg  Gly  Lys
          185                      190                      195
Val  Arg  Leu  Pro  Ala  Leu  His  Ile  Ala  Ala  Lys  Lys  Asp  Asp
               200                      205                      210
Thr  Lys  Ala  Ala  Thr  Leu  Leu  Leu  Gln  Asn  Glu  His  Asn  Ser
                    215                      220
Asp  Val  Thr  Ser  Lys  Ser  Gly  Phe  Thr  Pro  Leu  His  Ile  Ala
225                      230                      235
Ala  His  Tyr  Gly  Asn  Glu  Asn  Val  Ala  Gln  Leu  Leu  Leu  Glu
     240                      245                      250
Lys  Gly  Ala  Asn  Val  Asn  Tyr  Gln  Ala  Arg  His  Asn  Ile  Ser
          255                      260                      265
Pro  Leu  His  Val  Ala  Thr  Lys  Trp  Gly  Arg  Thr  Asn  Met  Val
               270                      275                      280
Ser  Leu  Leu  Leu  Ala  His  Gly  Ala  Val  Ile  Asp  Cys  Arg  Thr
                    285                      290
Arg  Asp  Leu  Leu  Thr  Pro  Leu  His  Cys  Ala  Ser  Arg  Ser  Gly
295                      300                      305
His  Asp  Gln  Val  Val  Asp  Leu  Leu  Leu  Glu  Lys  Gly  Ala  Pro
     310                      315                      320
Ile  Ser  Ala  Lys  Thr  Lys  Asn  Gly  Leu  Ala  Pro  Leu  His  Met
          325                      330                      335
Ala  Ala  Gln  Val  Asp  Asp  Val  Thr  Val  Asp  Tyr  Leu
               340                      345
```

( 2 ) INFORMATION FOR SEQ ID NO:29:

( i ) SEQUENCE CHARACTERISTICS:
        ( A ) LENGTH: 1096 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

| | | | | |  |
|---|---|---|---|---|---|
| GTGAGATAGT | CAACAGTAAC | ATCATCCACC | TGTGCTGCCA | TATGTAAGGG | 50 |
| AGCCAAACCA | TTTTTTGTCT | TAGCACTGAT | TGGAGCTCCT | TTTTCAAGCA | 100 |
| ACAAATCAAC | AACTTGATCA | TGACCTGAAC | GAGAAGCACA | GTGTAATGGT | 150 |
| GTTAGTAAAT | CACGTGTGCG | ACAGTCAATT | ACGGCCCCAT | GAGCCAACAA | 200 |
| TAACGAAACC | ATGTTTGTAC | GACCCCATTT | TGTTGCAACG | TGTAACGGAC | 250 |
| TTATGTTATG | TCTCGCTTGG | TAATTCACAT | TGGCTCCCTT | TTCGAGTAGC | 300 |
| AGTTGTGCTA | CGTTCTCATT | TCCATAGTGA | GCGGCGATAT | GAAGCGGAGT | 350 |
| AAAGCCGCTT | TTCGAAGTCA | CATCCGAGTT | ATGCTCATTT | TGAAGTAATA | 400 |
| GCGTAGCTGC | TTTCGTATCA | TCTTTTTTAG | CAGCAATATG | CAGTGCTGGC | 450 |
| AAGCGCACTT | TCCCGCGCGT | GTCATTTTCA | AGCAAAACAG | CGACCACACG | 500 |
| ATCGTGACCT | TGTTGCAAGG | CAACTGCCAG | TGGCGTAAAA | CCGTCTTCTG | 550 |
| TACTTAAAGC | TTGATTGGCA | TTGTGGGCAA | GAAGATAGCG | TACAACAGAT | 600 |
| TCGTGATTTT | CTTGTGCAGC | CATGTAAAGT | GGTGTAAAAC | CGTTTAGTGA | 650 |
| TTGTACGTTA | ACATTAGCAC | CATTTTCAAC | AAGTACTGTG | ACGATTAGTT | 700 |
| CTTGTCCTGC | CAATGATGCT | ATATGTAACG | CTGTGTTACC | CTTTCTAGTG | 750 |
| GCAGCATCAA | CATCTGCTTT | TCTTTTCAGA | AGTTCGCGGA | CCACTTCATG | 800 |
| ATGACCTTCT | TTGGAGGCCA | GATGCAATGC | ATTAAGGCCA | TTCGCATTGC | 850 |
| ATGTGTTGAT | ATCGGTGCCC | GAACGAAGTA | GTTCAAGTAC | ACGATCCAAA | 900 |
| TTTCCAGCTC | TTGCTGCTCG | TAAAAAACTT | GCACTGCTCT | CACCTTTGTT | 950 |
| GGAATGTTGA | CTGTTATCAT | CAGGAATTTG | TTGTTGATGT | TGTGAATCTT | 1000 |
| TTGGTTCTGC | GGGCCAGCCA | CTTCCCTCGA | CTATAGGATT | ACTCATCAAT | 1050 |
| AGTTGAGTTA | TATCAGTCAG | CCGCCTCAAA | CTTGGGTAAT | TAAACC | 1096 |

( 2 ) INFORMATION FOR SEQ ID NO:30:

( i ) SEQUENCE CHARACTERISTICS:
   ( A ) LENGTH: 1044 nucleotides
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:30:

| | | | | |  |
|---|---|---|---|---|---|
| ATGAGTAATC | CTATAGTCGA | GGGAAGTGGC | TGGCCCGCAG | AACCAAAAGA | 50 |
| TTCACAACAT | CAACAACAAA | TTCCTGATGA | TAACAGTCAA | CATTCCAACA | 100 |
| AAGGTGAGAG | CAGTGCAAGT | TTTTTACGAG | CAGCAAGAGC | TGGAAATTTG | 150 |
| GATCGTGTAC | TTGAACTACT | TCGTTCGGGC | ACCGATATCA | ACACATGCAA | 200 |
| TGCGAATGGC | CTTAATGCAT | TGCATCTGGC | CTCCAAAGAA | GGTCATCATG | 250 |
| AAGTGGTCCG | CGAACTTCTG | AAAAGAAAAG | CAGATGTTGA | TGCTGCCACT | 300 |
| AGAAAGGGTA | ACACAGCGTT | ACATATAGCA | TCATTGGCAG | GACAAGAACT | 350 |
| AATCGTCACA | GTACTTGTTG | AAAATGGTGC | TAATGTTAAC | GTACAATCAC | 400 |
| TAAACGGTTT | TACACCACTT | TACATGGCTG | CACAAGAAAA | TCACGAATCT | 450 |

| | | | | | |
|---|---|---|---|---|---|
| GTTGTACGCT | ATCTTCTTGC | CCACAATGCC | AATCAAGCTT | TAAGTACAGA | 500 |
| AGACGGTTTT | ACGCCACTGG | CAGTTGCCTT | GCAACAAGGT | CACGATCGTG | 550 |
| TGGTCGCTGT | TTTGCTTGAA | AATGACACGC | GCGGGAAAGT | GCGCTTGCCA | 600 |
| GCACTGCATA | TTGCTGCTAA | AAAAGATGAT | ACGAAAGCAG | CTACGCTATT | 650 |
| ACTTCAAAAT | GAGCATAACT | CGGATGTGAC | TTCGAAAAGC | GGCTTTACTC | 700 |
| CGCTTCATAT | CGCCGCTCAC | TATGGAAATG | AGAACGTAGC | ACAACTGCTA | 750 |
| CTCGAAAAGG | GAGCCAATGT | GAATTACCAA | GCGAGACATA | ACATAAGTCC | 800 |
| GTTACACGTT | GCAACAAAAT | GGGGTCGTAC | AAACATGGTT | TCGTTATTGT | 850 |
| TGGCTCATGG | GGCCGTAATT | GACTGTCGCA | CACGTGATTT | ACTAACACCA | 900 |
| TTACACTGTG | CTTCTCGTTC | AGGTCATGAT | CAAGTTGTTG | ATTTGTTGCT | 950 |
| TGAAAAAGGA | GCTCCAATCA | GTGCTAAGAC | AAAAAATGGT | TTGGCTCCCT | 1000 |
| TACATATGGC | AGCACAGGTG | GATGATGTTA | CTGTTGACTA | TCTC | 1044 |

(2) INFORMATION FOR SEQ ID NO:31:

(i) SEQUENCE CHARACTERISTICS:
        (A) LENGTH: 1044 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

| | | | | | |
|---|---|---|---|---|---|
| GAGATAGTCA | ACAGTAACAT | CATCCACCTG | TGCTGCCATA | TGTAAGGGAG | 50 |
| CCAAACCATT | TTTTGTCTTA | GCACTGATTG | GAGCTCCTTT | TTCAAGCAAC | 100 |
| AAATCAACAA | CTTGATCATG | ACCTGAACGA | GAAGCACAGT | GTAATGGTGT | 150 |
| TAGTAAATCA | CGTGTGCGAC | AGTCAATTAC | GGCCCCATGA | GCCAACAATA | 200 |
| ACGAAACCAT | GTTTGTACGA | CCCCATTTTG | TTGCAACGTG | TAACGGACTT | 250 |
| ATGTTATGTC | TCGCTTGGTA | ATTCACATTG | GCTCCCTTTT | CGAGTAGCAG | 300 |
| TTGTGCTACG | TTCTCATTTC | CATAGTGAGC | GGCGATATGA | AGCGGAGTAA | 350 |
| AGCCGCTTTT | CGAAGTCACA | TCCGAGTTAT | GCTCATTTTG | AAGTAATAGC | 400 |
| GTAGCTGCTT | TCGTATCATC | TTTTTTAGCA | GCAATATGCA | GTGCTGGCAA | 450 |
| GCGCACTTTC | CCGCGCGTGT | CATTTTCAAG | CAAAACAGCG | ACCACACGAT | 500 |
| CGTGACCTTG | TTGCAAGGCA | ACTGCCAGTG | GCGTAAAACC | GTCTTCTGTA | 550 |
| CTTAAAGCTT | GATTGGCATT | GTGGGCAAGA | AGATAGCGTA | CAACAGATTC | 600 |
| GTGATTTTCT | TGTGCAGCCA | TGTAAAGTGG | TGTAAAACCG | TTTAGTGATT | 650 |
| GTACGTTAAC | ATTAGCACCA | TTTTCAACAA | GTACTGTGAC | GATTAGTTCT | 700 |
| TGTCCTGCCA | ATGATGCTAT | ATGTAACGCT | GTGTTACCCT | TTCTAGTGGC | 750 |
| AGCATCAACA | TCTGCTTTTC | TTTTCAGAAG | TTCGCGGACC | ACTTCATGAT | 800 |
| GACCTTCTTT | GGAGGCCAGA | TGCAATGCAT | TAAGGCCATT | CGCATTGCAT | 850 |
| GTGTTGATAT | CGGTGCCCGA | ACGAAGTAGT | TCAAGTACAC | GATCCAAATT | 900 |
| TCCAGCTCTT | GCTGCTCGTA | AAAAACTTGC | ACTGCTCTCA | CCTTTGTTGG | 950 |
| AATGTTGACT | GTTATCATCA | GGAATTTGTT | GTTGATGTTG | TGAATCTTTT | 1000 |
| GGTTCTGCGG | GCCAGCCACT | TCCCTCGACT | ATAGGATTAC | TCAT | 1044 |

( 2 ) INFORMATION FOR SEQ ID NO:32:

( i ) SEQUENCE CHARACTERISTICS:
        ( A ) LENGTH: 5503 nucleotides
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 51..5285

( x i ) SEQUENCE DESCRIPTION: SEQ ID NO:32:

```
GGTTTAATTA  CCCAAGTTTG  AGGCGGCTGA  CTGATATAAC  TCAACTATTG                        50

ATG  AGT  AAT  CCT  ATA  GTC  GAG  GGA  AGT  GGC  TGG  CCC  GCA  GAA             92
Met  Ser  Asn  Pro  Ile  Val  Glu  Gly  Ser  Gly  Trp  Pro  Ala  Glu
 1              5                        10

CCA  AAA  GAT  TCA  CAA  CAT  CAA  CAA  CAA  ATT  CCT  GAT  GAT  AAC             134
Pro  Lys  Asp  Ser  Gln  His  Gln  Gln  Gln  Ile  Pro  Asp  Asp  Asn
15                       20                           25

AGT  CAA  CAT  TCC  AAC  AAA  GGT  GAG  AGC  AGT  GCA  AGT  TTT  TTA             176
Ser  Gln  His  Ser  Asn  Lys  Gly  Glu  Ser  Ser  Ala  Ser  Phe  Leu
          30                      35                          40

CGA  GCA  GCA  AGA  GCT  GGA  AAT  TTG  GAT  CGT  GTA  CTT  GAA  CTA             218
Arg  Ala  Ala  Arg  Ala  Gly  Asn  Leu  Asp  Arg  Val  Leu  Glu  Leu
               45                       50                     55

CTT  CGT  TCG  GGC  ACC  GAT  ATC  AAC  ACA  TGC  AAT  GCG  AAT  GGC             260
Leu  Arg  Ser  Gly  Thr  Asp  Ile  Asn  Thr  Cys  Asn  Ala  Asn  Gly
                     60                       65                     70

CTT  AAT  GCA  TTG  CAT  CTG  GCC  TCC  AAA  GAA  GGT  CAT  CAT  GAA             302
Leu  Asn  Ala  Leu  His  Leu  Ala  Ser  Lys  Glu  Gly  His  His  Glu
                         75                       80

GTG  GTC  CGC  GAA  CTT  CTG  AAA  AGA  AAA  GCA  GAT  GTT  GAT  GCT             344
Val  Val  Arg  Glu  Leu  Leu  Lys  Arg  Lys  Ala  Asp  Val  Asp  Ala
85                        90                           95

GCC  ACT  AGA  AAG  GGT  AAC  ACA  GCG  TTA  CAT  ATA  GCA  TCA  TTG             386
Ala  Thr  Arg  Lys  Gly  Asn  Thr  Ala  Leu  His  Ile  Ala  Ser  Leu
      100                      105                          110

GCA  GGA  CAA  GAA  CTA  ATC  GTC  ACA  GTA  CTT  GTT  GAA  AAT  GGT             428
Ala  Gly  Gln  Glu  Leu  Ile  Val  Thr  Val  Leu  Val  Glu  Asn  Gly
           115                      120                          125

GCT  AAT  GTT  AAC  GTA  CAA  TCA  CTA  AAC  GGT  TTT  ACA  CCA  CTT             470
Ala  Asn  Val  Asn  Val  Gln  Ser  Leu  Asn  Gly  Phe  Thr  Pro  Leu
                130                      135                         140

TAC  ATG  GCT  GCA  CAA  GAA  AAT  CAC  GAA  TCT  GTT  GTA  CGC  TAT             512
Tyr  Met  Ala  Ala  Gln  Glu  Asn  His  Glu  Ser  Val  Val  Arg  Tyr
                    145                      150

CTT  CTT  GCC  CAC  AAT  GCC  AAT  CAA  GCT  TTA  AGT  ACA  GAA  GAC             554
Leu  Leu  Ala  His  Asn  Ala  Asn  Gln  Ala  Leu  Ser  Thr  Glu  Asp
155                      160                          165

GGT  TTT  ACG  CCA  CTG  GCA  GTT  GCC  TTG  CAA  CAA  GGT  CAC  GAT             596
Gly  Phe  Thr  Pro  Leu  Ala  Val  Ala  Leu  Gln  Gln  Gly  His  Asp
          170                      175                          180

CGT  GTG  GTC  GCT  GTT  TTG  CTT  GAA  AAT  GAC  ACG  CGC  GGG  AAA             638
Arg  Val  Val  Ala  Val  Leu  Leu  Glu  Asn  Asp  Thr  Arg  Gly  Lys
               185                      190                          195

GTG  CGC  TTG  CCA  GCA  CTG  CAT  ATT  GCT  GCT  AAA  AAA  GAT  GAT             680
Val  Arg  Leu  Pro  Ala  Leu  His  Ile  Ala  Ala  Lys  Lys  Asp  Asp
                    200                      205                     210

ACG  AAA  GCA  GCT  ACG  CTA  TTA  CTT  CAA  AAT  GAG  CAT  AAC  TCG             722
Thr  Lys  Ala  Ala  Thr  Leu  Leu  Leu  Gln  Asn  Glu  His  Asn  Ser
```

```
                              215                           220
GAT GTG ACT TCG AAA AGC GGC TTT ACT CCG CTT CAT ATC GCC                    764
Asp Val Thr Ser Lys Ser Gly Phe Thr Pro Leu His Ile Ala
225             230                     235

GCT CAC TAT GGA AAT GAG AAC GTA GCA CAA CTG CTA CTC GAA                    806
Ala His Tyr Gly Asn Glu Asn Val Ala Gln Leu Leu Leu Glu
    240                 245                     250

AAG GGA GCC AAT GTG AAT TAC CAA GCG AGA CAT AAC ATA AGT                    848
Lys Gly Ala Asn Val Asn Tyr Gln Ala Arg His Asn Ile Ser
        255                 260                     265

CCG TTA CAC GTT GCA ACA AAA TGG GGT CGT ACA AAC ATG GTT                    890
Pro Leu His Val Ala Thr Lys Trp Gly Arg Thr Asn Met Val
            270                 275                     280

TCG TTA TTG TTG GCT CAT GGG GCC GTA ATT GAC TGT CGC ACA                    932
Ser Leu Leu Leu Ala His Gly Ala Val Ile Asp Cys Arg Thr
                285                 290

CGT GAT TTA CTA ACA CCA TTA CAC TGT GCT TCT CGT TCA GGT                    974
Arg Asp Leu Leu Thr Pro Leu His Cys Ala Ser Arg Ser Gly
295                 300                 305

CAT GAT CAA GTT GTT GAT TTG TTG CTT GAA AAA GGA GCT CCA                   1016
His Asp Gln Val Val Asp Leu Leu Leu Glu Lys Gly Ala Pro
    310                 315                     320

ATC AGT GCT AAG ACA AAA AAT GGT TTG GCT CCC TTA CAT ATG                   1058
Ile Ser Ala Lys Thr Lys Asn Gly Leu Ala Pro Leu His Met
        325                 330                     335

GCA GCA CAG GTG GAT GAT GTT ACT GTT GAC TAT CTC ACT CCT                   1100
Ala Ala Gln Val Asp Asp Val Thr Val Asp Tyr Leu Thr Pro
            340                 345                     350

CTT CAT GTG GCT GCT CAT TGC GGA CAT GTC CGT GTC GCT AAA                   1142
Leu His Val Ala Ala His Cys Gly His Val Arg Val Ala Lys
                355                 360

CTT TTG CTG GAT CGT AAT GCT GAC CCG AAT GCT CGA GCT CTC                   1184
Leu Leu Leu Asp Arg Asn Ala Asp Pro Asn Ala Arg Ala Leu
365                 370                 375

AAT GGC TTC ACA CCG CTG CAT ATC GCT TGC AAA AAA AAT CGC                   1226
Asn Gly Phe Thr Pro Leu His Ile Ala Cys Lys Lys Asn Arg
    380                 385                     390

ATT AAA ATT GTC GAA CTG CTA CTG AAA TAC CAC GCT GCA ATC                   1268
Ile Lys Ile Val Glu Leu Leu Leu Lys Tyr His Ala Ala Ile
        395                 400                     405

GAA GCA ACT ACT GAA TCC GGT CTC TCA CCG CTG CAT GTC GCT                   1310
Glu Ala Thr Thr Glu Ser Gly Leu Ser Pro Leu His Val Ala
            410                 415                     420

GCT TTT ATG GGT GCT ATA AAC ATT GTC ATC TAT TTA CTA CAA                   1352
Ala Phe Met Gly Ala Ile Asn Ile Val Ile Tyr Leu Leu Gln
                425                 430

CAA GGT GCT AAT GCA GAT GTG GCT ACA GTA CGC GGT GAA ACG                   1394
Gln Gly Ala Asn Ala Asp Val Ala Thr Val Arg Gly Glu Thr
435                 440                 445

CCT CTT CAT TTA GCT GCA CGA GCA AAC CAA ACG GAC ATT GTT                   1436
Pro Leu His Leu Ala Ala Arg Ala Asn Gln Thr Asp Ile Val
    450                 455                     460

CGT GTT TTG GTG CGT AAT GGA GCA CAG GTG GAT GCT GCT GCT                   1478
Arg Val Leu Val Arg Asn Gly Ala Gln Val Asp Ala Ala Ala
        465                 470                     475

CGT GAA CTA CAA ACT CCA CTG CAC ATT GCA TCA CGT CTT GGT                   1520
Arg Glu Leu Gln Thr Pro Leu His Ile Ala Ser Arg Leu Gly
            480                 485                     490

AAT ACC GAC ATC GTC ATT TTG TTG CTG CAG GCT AAT GCA TCA                   1562
Asn Thr Asp Ile Val Ile Leu Leu Leu Gln Ala Asn Ala Ser
```

```
                                   495                       500
CCA  AAT  GCT  GCC  ACA  AGA  GAT  CTT  TAT  ACT  CCT  CTT  CAT  ATT              1604
Pro  Asn  Ala  Ala  Thr  Arg  Asp  Leu  Tyr  Thr  Pro  Leu  His  Ile
505                 510                      515

GCT  GCC  AAG  GAG  GGG  CAA  GAG  GAA  GTG  GCA  GCA  ATA  TTG  ATG              1646
Ala  Ala  Lys  Glu  Gly  Gln  Glu  Glu  Val  Ala  Ala  Ile  Leu  Met
     520                 525                      530

GAT  CAT  GGA  ACC  GAC  AAG  ACA  CTG  CTC  ACG  AAA  AAG  GGT  TTT              1688
Asp  His  Gly  Thr  Asp  Lys  Thr  Leu  Leu  Thr  Lys  Lys  Gly  Phe
          535                      540                      545

ACG  CCG  TTG  CAT  TTA  GCT  GCT  AAG  TAT  GGC  AAT  TTG  CCG  GTC              1730
Thr  Pro  Leu  His  Leu  Ala  Ala  Lys  Tyr  Gly  Asn  Leu  Pro  Val
               550                      555                      560

GCG  AAA  TCA  TTG  CTA  GAA  CGA  GGA  ACA  CCG  GTT  GAC  ATT  GAA              1772
Ala  Lys  Ser  Leu  Leu  Glu  Arg  Gly  Thr  Pro  Val  Asp  Ile  Glu
                    565                      570

GGC  AAG  AAT  CAG  GTA  ACA  CCT  CTG  CAT  GTA  GCG  GCA  CAT  TAC              1814
Gly  Lys  Asn  Gln  Val  Thr  Pro  Leu  His  Val  Ala  Ala  His  Tyr
575                      580                      585

AAT  AAC  GAC  AAG  GTA  GCA  TTG  TTA  CTT  CTA  GAA  AAT  GGT  GCT              1856
Asn  Asn  Asp  Lys  Val  Ala  Leu  Leu  Leu  Leu  Glu  Asn  Gly  Ala
     590                      595                      600

TCT  GCA  CAT  GCC  GCT  GCC  AAG  AAT  GGG  TAC  ACT  CCT  TTA  CAT              1898
Ser  Ala  His  Ala  Ala  Ala  Lys  Asn  Gly  Tyr  Thr  Pro  Leu  His
          605                      610                      615

ATT  GCC  GCG  AAG  AAG  AAT  CAG  ATG  GAT  ATT  GCT  AGC  ACT  CTC              1940
Ile  Ala  Ala  Lys  Lys  Asn  Gln  Met  Asp  Ile  Ala  Ser  Thr  Leu
               620                      625                      630

CTT  CAT  TAT  AAG  GCA  AAT  GCG  AAT  GCT  GAA  AGC  AAA  GCT  GGC              1982
Leu  His  Tyr  Lys  Ala  Asn  Ala  Asn  Ala  Glu  Ser  Lys  Ala  Gly
                    635                      640

TTT  ACA  CCA  CTT  CAT  CTT  GCC  GCC  CAG  GAG  GGC  CAT  CGC  GAA              2024
Phe  Thr  Pro  Leu  His  Leu  Ala  Ala  Gln  Glu  Gly  His  Arg  Glu
645                      650                      655

ATG  GCT  GCG  TTA  TTA  ATT  GAA  AAT  GGA  GCA  AAA  GTT  GGA  GCT              2066
Met  Ala  Ala  Leu  Leu  Ile  Glu  Asn  Gly  Ala  Lys  Val  Gly  Ala
     660                      665                      670

CAG  GCA  AGG  AAT  GGC  TTG  ACA  CCA  ATG  CAT  TTA  TGT  GCA  CAG              2108
Gln  Ala  Arg  Asn  Gly  Leu  Thr  Pro  Met  His  Leu  Cys  Ala  Gln
          675                      680                      685

GAG  GAT  CGT  GTG  AGC  GTA  GCA  GAA  GAA  CTA  GTG  AAA  GAA  AAC              2150
Glu  Asp  Arg  Val  Ser  Val  Ala  Glu  Glu  Leu  Val  Lys  Glu  Asn
               690                      695                      700

GCA  GCC  ATT  GAT  CCC  AAA  ACG  AAA  GCA  GGA  TAT  ACG  CCG  TTA              2192
Ala  Ala  Ile  Asp  Pro  Lys  Thr  Lys  Ala  Gly  Tyr  Thr  Pro  Leu
                    705                      710

CAT  GTT  GCT  TGC  CAT  TTT  GGA  CAA  ATA  AAC  ATG  GTC  CGT  TTC              2234
His  Val  Ala  Cys  His  Phe  Gly  Gln  Ile  Asn  Met  Val  Arg  Phe
715                      720                      725

TTG  ATT  GAG  CAT  GGC  GCA  CGA  GTT  TCA  GTT  ATT  ACT  CGT  GCT              2276
Leu  Ile  Glu  His  Gly  Ala  Arg  Val  Ser  Val  Ile  Thr  Arg  Ala
     730                      735                      740

TCC  TAT  ACT  CCT  CTG  CAT  CAA  GCT  GCT  CAG  CAA  GGG  CAT  AAC              2318
Ser  Tyr  Thr  Pro  Leu  His  Gln  Ala  Ala  Gln  Gln  Gly  His  Asn
          745                      750                      755

AGT  GTT  GTA  CGT  TAC  TTG  TTG  GAA  CAT  GGT  GCA  AGT  CCA  AAT              2360
Ser  Val  Val  Arg  Tyr  Leu  Leu  Glu  His  Gly  Ala  Ser  Pro  Asn
               760                      765                      770

GTT  CAT  ACA  TCG  ACA  GGA  CAA  ACT  CCA  TTA  TCG  ATT  GCT  GAA              2402
Val  His  Thr  Ser  Thr  Gly  Gln  Thr  Pro  Leu  Ser  Ile  Ala  Glu
```

```
                                775                            780
CGT  CTA  GGG  TAT  GTA  TCC  GTG  GTT  GAA  GCG  CTT  AAA  ACA  ATT    2444
Arg  Leu  Gly  Tyr  Val  Ser  Val  Val  Glu  Ala  Leu  Lys  Thr  Ile
785            790                      795

ACC  GAG  ACT  ACT  GTG  ATA  ACG  GAG  ACC  ACA  ACC  GTT  ACT  GAA    2486
Thr  Glu  Thr  Thr  Val  Ile  Thr  Glu  Thr  Thr  Thr  Val  Thr  Glu
     800                 805                      810

GAA  AGA  TAT  AAA  CCT  CAG  AAT  CCC  GAA  GCA  ATG  AAT  GAA  ACC    2528
Glu  Arg  Tyr  Lys  Pro  Gln  Asn  Pro  Glu  Ala  Met  Asn  Glu  Thr
          815                 820                           825

ATG  TTT  TCC  GAT  TCC  GAA  GAT  GAA  GGT  GAA  GAT  AAT  CAG  ATC    2570
Met  Phe  Ser  Asp  Ser  Glu  Asp  Glu  Gly  Glu  Asp  Asn  Gln  Ile
               830                 835                          840

ACA  GCC  AAT  GCT  CAT  GCT  CAT  GAT  TTC  TCA  GAA  AGC  CTC  ACA    2612
Thr  Ala  Asn  Ala  His  Ala  His  Asp  Phe  Ser  Glu  Ser  Leu  Thr
                    845                      850

AAA  GGT  TTG  CAC  GAT  TCA  ACT  GGT  GTA  CAT  TTG  ATT  CAT  GCC    2654
Lys  Gly  Leu  His  Asp  Ser  Thr  Gly  Val  His  Leu  Ile  His  Ala
855                      860                      865

ACA  GAA  CCG  ACA  TTG  TCA  CGA  AGT  CCG  GAA  GTG  GAA  GGT  ACG    2696
Thr  Glu  Pro  Thr  Leu  Ser  Arg  Ser  Pro  Glu  Val  Glu  Gly  Thr
     870                      875                      880

GAT  GGC  GAT  TTG  GAT  GCC  TTA  ATT  CGT  AAA  GCA  CAA  CAT  GAA    2738
Asp  Gly  Asp  Leu  Asp  Ala  Leu  Ile  Arg  Lys  Ala  Gln  His  Glu
          885                      890                      895

CCA  ATT  ACT  ACA  GCG  ATG  GCC  GAT  CCT  TCC  TTA  GAT  GCA  TCG    2780
Pro  Ile  Thr  Thr  Ala  Met  Ala  Asp  Pro  Ser  Leu  Asp  Ala  Ser
               900                      905                      910

CTT  CCT  GAC  AAT  GTT  ACG  ATA  ATG  AGA  ACT  ACC  ATG  CAA  CCT    2822
Leu  Pro  Asp  Asn  Val  Thr  Ile  Met  Arg  Thr  Thr  Met  Gln  Pro
                    915                      920

AGT  TTT  TTA  ATT  TCG  TTT  ATG  GTG  GAT  GCA  CGT  GGA  GGA  GCA    2864
Ser  Phe  Leu  Ile  Ser  Phe  Met  Val  Asp  Ala  Arg  Gly  Gly  Ala
925                      930                      935

ATG  CGT  GGT  TGT  AGG  CAT  TCC  GGT  GTC  AGA  ATC  ATT  ATA  CCA    2906
Met  Arg  Gly  Cys  Arg  His  Ser  Gly  Val  Arg  Ile  Ile  Ile  Pro
     940                      945                      950

CCG  AGG  AAA  GCG  CCG  CAA  CCT  ACA  CGG  GTC  ACA  TGC  AGA  TAC    2948
Pro  Arg  Lys  Ala  Pro  Gln  Pro  Thr  Arg  Val  Thr  Cys  Arg  Tyr
          955                      960                      965

CTT  GGA  AAG  GAC  AAG  TTA  GCG  CAT  CCA  CCA  CCA  TTA  AGT  GAA    2990
Leu  Gly  Lys  Asp  Lys  Leu  Ala  His  Pro  Pro  Pro  Leu  Ser  Glu
               970                      975                      980

GGT  GAA  GCG  CTC  GCN  TCA  CGT  ATA  CTT  GAA  ATG  GCA  CCA  CAT    3032
Gly  Glu  Ala  Leu  Ala  Ser  Arg  Ile  Leu  Glu  Met  Ala  Pro  His
                    985                      990

GGA  GCA  AAA  TTC  TTA  GGC  CCT  GTT  ATA  TTG  GAA  GTA  CCA  CAT    3074
Gly  Ala  Lys  Phe  Leu  Gly  Pro  Val  Ile  Leu  Glu  Val  Pro  His
995                      1000                     1005

TTT  GCA  TCA  CTT  CGT  GGA  CGA  GAG  AGA  GAG  ATT  GTC  ATT  TTG    3116
Phe  Ala  Ser  Leu  Arg  Gly  Arg  Glu  Arg  Glu  Ile  Val  Ile  Leu
     1010                     1015                     1020

CGT  TCT  GAT  GAT  GGG  CAG  CAT  TGG  AAA  GAG  CAT  CAG  CTT  GAA    3158
Arg  Ser  Asp  Asp  Gly  Gln  His  Trp  Lys  Glu  His  Gln  Leu  Glu
          1025                     1030                     1035

GCA  ACA  GAA  GAT  GCT  GTA  CAA  GAG  GTG  CTC  AAT  GAA  TCG  TTT    3200
Ala  Thr  Glu  Asp  Ala  Val  Gln  Glu  Val  Leu  Asn  Glu  Ser  Phe
               1040                     1045                     1050

GAT  GCA  GAA  GAG  TTG  TCG  CAA  CTT  GAT  GAT  TTG  CAT  ACA  TCA    3242
Asp  Ala  Glu  Glu  Leu  Ser  Gln  Leu  Asp  Asp  Leu  His  Thr  Ser
```

-continued

```
                     1055                          1060
CGG ATT ACG CGT ATC CTG ACC AAT GAT TTC CCA ATG TAT TTC              3284
Arg Ile Thr Arg Ile Leu Thr Asn Asp Phe Pro Met Tyr Phe
1065                 1070                          1075

GCG GTC GTT ACT CGT GTG CGG CAA GAA GTG CAC TGT GTT GGT              3326
Ala Val Val Thr Arg Val Arg Gln Glu Val His Cys Val Gly
        1080                 1085                 1090

CCA GAA GGT GGT GTA ATA CTC TCT TCA GTT GTT CCT CAT GTG              3368
Pro Glu Gly Gly Val Ile Leu Ser Ser Val Val Pro His Val
            1095                 1100                 1105

CAG GCC ATA TTT CCG GAT GGT TCC TTG ACT AAG ACG ATC AAA              3410
Gln Ala Ile Phe Pro Asp Gly Ser Leu Thr Lys Thr Ile Lys
                 1110                 1115                 1120

GTA TCT GTG CAA GCC CAG CCA GTT CCA CAA GAG ATA GTC ACT              3452
Val Ser Val Gln Ala Gln Pro Val Pro Gln Glu Ile Val Thr
                     1125                 1130

CGT TTA CAT GGG AAT AGA GTC GCT GTT TCT CCA ATT GTA ACT              3494
Arg Leu His Gly Asn Arg Val Ala Val Ser Pro Ile Val Thr
1135                 1140                 1145

GTT GAA CCG CGT CGT CGC AAA TTC CAT AAG CCC ATA ACG CTG              3536
Val Glu Pro Arg Arg Arg Lys Phe His Lys Pro Ile Thr Leu
        1150                 1155                 1160

TGC ATA CCA TTG CCA CAA AGC TCA AAT AAA GGA ATG TTA ACA              3578
Cys Ile Pro Leu Pro Gln Ser Ser Asn Lys Gly Met Leu Thr
            1165                 1170                 1175

CAA TAT AGT GGC CAA CCA GGA CAG GAA CCA CCG ACG CTG CGT              3620
Gln Tyr Ser Gly Gln Pro Gly Gln Glu Pro Pro Thr Leu Arg
                 1180                 1185                 1190

TTA CTC TGC AGT AAA ACT GGA GGT TCT TCT CCT GCA CAG TGG              3662
Leu Leu Cys Ser Lys Thr Gly Gly Ser Ser Pro Ala Gln Trp
                     1195                 1200

GAA GAT ATT ACT GGA ACT ACC CAG TTA ACA TTT ACT GGT GAG              3704
Glu Asp Ile Thr Gly Thr Thr Gln Leu Thr Phe Thr Gly Glu
1205                 1210                 1215

GAC GTT TCA TTT ACA ACT ACG GTT TCT GCT CGA TTT TGG TTG              3746
Asp Val Ser Phe Thr Thr Thr Val Ser Ala Arg Phe Trp Leu
        1220                 1225                 1230

ATG GAT TGC CAA ACT CCG CGA GAT GCG GCA CGA ATG GCA CAA              3788
Met Asp Cys Gln Thr Pro Arg Asp Ala Ala Arg Met Ala Gln
            1235                 1240                 1245

GAA GTT TAC AAT GAA GCA ATT GCA GTT CCT TAT ATG GCT AAA              3830
Glu Val Tyr Asn Glu Ala Ile Ala Val Pro Tyr Met Ala Lys
                 1250                 1255                 1260

TTT CTT ATT TTT GCT CGA CGA ACT TTT CCT GCC GAA GGA CAG              3872
Phe Leu Ile Phe Ala Arg Arg Thr Phe Pro Ala Glu Gly Gln
                     1265                 1270

TTG AGA TTG TTT TGT ATG ACT GAT GAT CGG GAA GAT AAA ACC              3914
Leu Arg Leu Phe Cys Met Thr Asp Asp Arg Glu Asp Lys Thr
1275                 1280                 1285

CTG GAA AAA CAA GAA CGT TTC ATT GAA ATT GCG AAA TCG AAA              3956
Leu Glu Lys Gln Glu Arg Phe Ile Glu Ile Ala Lys Ser Lys
        1290                 1295                 1300

GAT GTA GAA GTC TTA AGT GGG CGA CAT CAG TTT TTG GAA TTT              3998
Asp Val Glu Val Leu Ser Gly Arg His Gln Phe Leu Glu Phe
            1305                 1310                 1315

TCT GGA AAT CTT CTT CCA ATA ACC AAG AGT GGT GAC CAA CTT              4040
Ser Gly Asn Leu Leu Pro Ile Thr Lys Ser Gly Asp Gln Leu
                 1320                 1325                 1330

TCT CTT TAT TTT CTA CCA TTC CAA GAA AAT CGT CTT GCT TTC              4082
Ser Leu Tyr Phe Leu Pro Phe Gln Glu Asn Arg Leu Ala Phe
```

|  |  |
|---|---|
| ATG GTA AAG ATA CGC ACT CAC ACG GAC AAC GAA ACT GCA GCT<br>Met Val Lys Ile Arg Thr His Thr Asp Asn Glu Thr Ala Ala<br>1345                                1350                               1355 | 4124 |
| GAT GGC CGG ATA GTA TTT ATG AAA GAA CCA AAA TTG AGA GCC<br>Asp Gly Arg Ile Val Phe Met Lys Glu Pro Lys Leu Arg Ala<br>1360                                1365                             1370 | 4166 |
| GAA AAT TTA CCT CCG CAG ACG CCA GTG TGT ACT CTT GCA ATC<br>Glu Asn Leu Pro Pro Gln Thr Pro Val Cys Thr Leu Ala Ile<br>1375                                1380                             1385 | 4208 |
| ACT CTT CCG GAA TAC ACT GGG CCG GAG CCG ATG GTT TCC AAA<br>Thr Leu Pro Glu Tyr Thr Gly Pro Glu Pro Met Val Ser Lys<br>                 1390                             1395                       1400 | 4250 |
| AAA CTC TTC TAT TCG GAA GCT TCT TTG ACT GAG AAA TAC GTT<br>Lys Leu Phe Tyr Ser Glu Ala Ser Leu Thr Glu Lys Tyr Val<br>                            1405                             1410 | 4292 |
| GGA GCT TTC CAT GAA ACT GCT GAA CCT GAT AAC TTG CCA CTA<br>Gly Ala Phe His Glu Thr Ala Glu Pro Asp Asn Leu Pro Leu<br>1415                                1420                             1425 | 4334 |
| GCA CAT GTT GCA CTA TTA ATT GGC GCT GAT TGG CAT CGG TTA<br>Ala His Val Ala Leu Leu Ile Gly Ala Asp Trp His Arg Leu<br>                 1430                             1435                       1440 | 4376 |
| GCT CGA GCG CTT GAA GTA CCT GAT ATT GAT ATA CGA CAA GTT<br>Ala Arg Ala Leu Glu Val Pro Asp Ile Asp Ile Arg Gln Val<br>                            1445                             1450                       1455 | 4418 |
| CGA CAT CAA CTA GTT GGT CTT GAA GCA GTC ACT ATT CTA CGT<br>Arg His Gln Leu Val Gly Leu Glu Ala Val Thr Ile Leu Arg<br>                 1460                             1465                       1470 | 4460 |
| ATT TGG ATA TTT TTG AAG AAA GAA CAA GCT ACG CCC GTT GCT<br>Ile Trp Ile Phe Leu Lys Lys Glu Gln Ala Thr Pro Val Ala<br>                            1475                             1480 | 4502 |
| TTG CGA TCA GCA TTG CAG CGA ATA GGA CGT GAT GAT GTT GTA<br>Leu Arg Ser Ala Leu Gln Arg Ile Gly Arg Asp Asp Val Val<br>1485                                1490 | 4544 |
| CGA GAA ATG GAT CGA GCT GAA AAG CTA GAT GGT TTA GAA GGA<br>Arg Glu Met Asp Arg Ala Glu Lys Leu Asp Gly Leu Glu Gly<br>                 1500                             1505                       1510 | 4586 |
| ACA CCT GTA TCG CAT ATT TCT GGA CCC TCA ATA ACT CTG TCA<br>Thr Pro Val Ser His Ile Ser Gly Pro Ser Ile Thr Leu Ser<br>                            1515                             1520                       1525 | 4628 |
| TCT ACT TTG CTA GAG GTA GCA GGC GAC AGA CGT CGT CAC GCC<br>Ser Thr Leu Leu Glu Val Ala Gly Asp Arg Arg Arg His Ala<br>                            1530                             1535                       1540 | 4670 |
| GAG GTA ACA ATG GCG CAA CAG CGA TTG GCA CAA GAA CCG TTT<br>Glu Val Thr Met Ala Gln Gln Arg Leu Ala Gln Glu Pro Phe<br>                 1545                             1550 | 4712 |
| TTT CAG CAA GTA GGG TAT AAT GGG ACA CCT GGA GAT CCA GAA<br>Phe Gln Gln Val Gly Tyr Asn Gly Thr Pro Gly Asp Pro Glu<br>1555                                1560                             1565 | 4754 |
| GAA CCC AAA GAA CAG TCA TTC CAC GAA GAG GAA GAG GAA GTT<br>Glu Pro Lys Glu Gln Ser Phe His Glu Glu Glu Glu Glu Val<br>                 1570                             1575                       1580 | 4796 |
| GCA GTT TCA GAA ATT CGA ACA GTT GTG CGC ACT GAA CGA CAT<br>Ala Val Ser Glu Ile Arg Thr Val Val Arg Thr Glu Arg His<br>                            1585                             1590                       1595 | 4838 |
| GTG CAT GAT TCG GAA AAT GGT CCT ATT GTG GAA GAG CGT ACA<br>Val His Asp Ser Glu Asn Gly Pro Ile Val Glu Glu Arg Thr<br>                 1600                             1605                       1610 | 4880 |
| ATA ACA ACT ACG TAT GAG GAT GAT GTT GCT GTA AAC GAA GAA<br>Ile Thr Thr Thr Tyr Glu Asp Asp Val Ala Val Asn Glu Glu | 4922 |

|     |     |     |     |     |     |     |     |     |     |     |     |     |     | |
|---|---|---|---|---|---|---|---|---|---|---|---|---|---|---|
| | | | | 1615 | | | | | 1620 | | | | | |
| GAA | ATT | GTT | GAC | AAA | ATA | GTG | CCT | CTC | AAC | GAA | GAG | GAG | CAA | 4964 |
| Glu | Ile | Val | Asp | Lys | Ile | Val | Pro | Leu | Asn | Glu | Glu | Glu | Gln | |
| 1625 | | | | 1630 | | | | | 1635 | | | | | |
| GAA | AAA | TGG | GAT | CGA | ATG | GTT | CGA | GAA | GTG | GAA | ATG | AAT | TTT | 5006 |
| Glu | Lys | Trp | Asp | Arg | Met | Val | Arg | Glu | Val | Glu | Met | Asn | Phe | |
| | 1640 | | | | 1645 | | | | | 1650 | | | | |
| GAG | CAA | CAA | GAA | ACA | TCA | AAA | GAA | GGA | ACG | TTT | GGT | TGT | CAG | 5048 |
| Glu | Gln | Gln | Glu | Thr | Ser | Lys | Glu | Gly | Thr | Phe | Gly | Cys | Gln | |
| | 1655 | | | | | 1660 | | | | | | 1665 | | |
| ACA | ACA | CAT | GAG | AAA | GAA | AAA | GAT | GAT | GAT | GGT | GGC | AGT | CTG | 5090 |
| Thr | Thr | His | Glu | Lys | Glu | Lys | Asp | Asp | Asp | Gly | Gly | Ser | Leu | |
| | | | 1670 | | | | 1675 | | | | | | 1680 | |
| AAG | ACG | ACA | ATG | AAA | GAT | AGT | CAC | GTA | AGG | CAG | ATT | TTC | TTC | 5132 |
| Lys | Thr | Thr | Met | Lys | Asp | Ser | His | Val | Arg | Gln | Ile | Phe | Phe | |
| | | | | 1685 | | | | | 1690 | | | | | |
| GAT | GGA | GGT | GAG | ACA | TCC | GCT | AAT | GAA | ACA | GGA | TTA | AGT | AGC | 5174 |
| Asp | Gly | Gly | Glu | Thr | Ser | Ala | Asn | Glu | Thr | Gly | Leu | Ser | Ser | |
| 1695 | | | | | 1700 | | | | | | 1705 | | | |
| GGG | GAT | GCA | GAC | ACT | ATT | ATG | ACT | CCA | ACG | ACA | AAG | GAG | GAT | 5216 |
| Gly | Asp | Ala | Asp | Thr | Ile | Met | Thr | Pro | Thr | Thr | Lys | Glu | Asp | |
| | 1710 | | | | | 1715 | | | | | | 1720 | | |
| AAT | CAT | GTT | ATA | GAC | GTA | ATG | GAG | GAA | AGG | CGA | ACT | GAT | GAA | 5258 |
| Asn | His | Val | Ile | Asp | Val | Met | Glu | Glu | Arg | Arg | Thr | Asp | Glu | |
| | | 1725 | | | | | 1730 | | | | | | 1735 | |
| GAG | GCC | AAA | GGG | CAA | AGC | GTT | CAT | GAA | TAA | TCTGGATCCA | | | | 5298 |
| Glu | Ala | Lys | Gly | Gln | Ser | Val | His | Glu | | | | | | |
| | | | 1740 | | | | | 1745 | | | | | | |

| | | | | | |
|---|---|---|---|---|---|
| CAAATTGATT | TAAATCGCAA | TCTCGCACAT | GCCTATGTTG | CTAATATTTA | 5348 |
| ATGAAATTTT | TCAAAGCAAT | AATTTGAATG | CTGTTTGGGC | TTCCCATATT | 5398 |
| GTTAAAGCGT | TTTCCATCGT | CCATTCACTT | TTTGTTTTTG | CTGTAGTCTG | 5448 |
| TAACTGCTAC | TCTTGATAAA | TTTGCTCCAG | TAAAAAAAAA | AAAAAAAAA | 5498 |
| AAAAA | | | | | 5503 |

( 2 ) INFORMATION FOR SEQ ID NO:33:

( i ) SEQUENCE CHARACTERISTICS:
        ( A ) LENGTH: 1745 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

| | | | | | | | | | | | |
|---|---|---|---|---|---|---|---|---|---|---|---|
| Met | Ser | Asn | Pro | Ile | Val | Glu | Gly | Ser | Gly | Trp | Pro | Ala | Glu |
| 1 | | | | 5 | | | | | 10 | | | | |
| Pro | Lys | Asp | Ser | Gln | His | Gln | Gln | Gln | Ile | Pro | Asp | Asp | Asn |
| 15 | | | | | 20 | | | | | 25 | | | |
| Ser | Gln | His | Ser | Asn | Lys | Gly | Glu | Ser | Ser | Ala | Ser | Phe | Leu |
| | 30 | | | | | 35 | | | | | 40 | | |
| Arg | Ala | Ala | Arg | Ala | Gly | Asn | Leu | Asp | Arg | Val | Leu | Glu | Leu |
| | | 45 | | | | | 50 | | | | | 55 | |
| Leu | Arg | Ser | Gly | Thr | Asp | Ile | Asn | Thr | Cys | Asn | Ala | Asn | Gly |
| | | | 60 | | | | | 65 | | | | | 70 |
| Leu | Asn | Ala | Leu | His | Leu | Ala | Ser | Lys | Glu | Gly | His | His | Glu |
| | | | | 75 | | | | | 80 | | | | |
| Val | Val | Arg | Glu | Leu | Leu | Lys | Arg | Lys | Ala | Asp | Val | Asp | Ala |
| 85 | | | | | 90 | | | | | 95 | | | |

```
Ala  Thr  Arg  Lys  Gly  Asn  Thr  Ala  Leu  His  Ile  Ala  Ser  Leu
     100                 105                      110

Ala  Gly  Gln  Glu  Leu  Ile  Val  Thr  Val  Leu  Val  Glu  Asn  Gly
          115                 120                      125

Ala  Asn  Val  Asn  Val  Gln  Ser  Leu  Asn  Gly  Phe  Thr  Pro  Leu
               130                 135                           140

Tyr  Met  Ala  Ala  Gln  Glu  Asn  His  Glu  Ser  Val  Val  Arg  Tyr
                    145                      150

Leu  Leu  Ala  His  Asn  Ala  Asn  Gln  Ala  Leu  Ser  Thr  Glu  Asp
155                      160                      165

Gly  Phe  Thr  Pro  Leu  Ala  Val  Ala  Leu  Gln  Gln  Gly  His  Asp
     170                 175                           180

Arg  Val  Val  Ala  Val  Leu  Leu  Glu  Asn  Asp  Thr  Arg  Gly  Lys
          185                 190                           195

Val  Arg  Leu  Pro  Ala  Leu  His  Ile  Ala  Ala  Lys  Lys  Asp  Asp
               200                      205                      210

Thr  Lys  Ala  Ala  Thr  Leu  Leu  Leu  Gln  Asn  Glu  His  Asn  Ser
                    215                 220

Asp  Val  Thr  Ser  Lys  Ser  Gly  Phe  Thr  Pro  Leu  His  Ile  Ala
225                      230                 235

Ala  His  Tyr  Gly  Asn  Glu  Asn  Val  Ala  Gln  Leu  Leu  Leu  Glu
     240                 245                      250

Lys  Gly  Ala  Asn  Val  Asn  Tyr  Gln  Ala  Arg  His  Asn  Ile  Ser
          255                 260                      265

Pro  Leu  His  Val  Ala  Thr  Lys  Trp  Gly  Arg  Thr  Asn  Met  Val
               270                 275                           280

Ser  Leu  Leu  Leu  Ala  His  Gly  Ala  Val  Ile  Asp  Cys  Arg  Thr
                    285                      290

Arg  Asp  Leu  Leu  Thr  Pro  Leu  His  Cys  Ala  Ser  Arg  Ser  Gly
295                      300                      305

His  Asp  Gln  Val  Val  Asp  Leu  Leu  Leu  Glu  Lys  Gly  Ala  Pro
     310                 315                      320

Ile  Ser  Ala  Lys  Thr  Lys  Asn  Gly  Leu  Ala  Pro  Leu  His  Met
          325                 330                      335

Ala  Ala  Gln  Val  Asp  Asp  Val  Thr  Val  Asp  Tyr  Leu  Thr  Pro
               340                 345                           350

Leu  His  Val  Ala  Ala  His  Cys  Gly  His  Val  Arg  Val  Ala  Lys
                    355                      360

Leu  Leu  Leu  Asp  Arg  Asn  Ala  Asp  Pro  Asn  Ala  Arg  Ala  Leu
365                      370                      375

Asn  Gly  Phe  Thr  Pro  Leu  His  Ile  Ala  Cys  Lys  Lys  Asn  Arg
     380                 385                      390

Ile  Lys  Ile  Val  Glu  Leu  Leu  Leu  Lys  Tyr  His  Ala  Ala  Ile
          395                 400                      405

Glu  Ala  Thr  Thr  Glu  Ser  Gly  Leu  Ser  Pro  Leu  His  Val  Ala
               410                 415                           420

Ala  Phe  Met  Gly  Ala  Ile  Asn  Ile  Val  Ile  Tyr  Leu  Leu  Gln
                    425                      430

Gln  Gly  Ala  Asn  Ala  Asp  Val  Ala  Thr  Val  Arg  Gly  Glu  Thr
435                      440                      445

Pro  Leu  His  Leu  Ala  Ala  Arg  Ala  Asn  Gln  Thr  Asp  Ile  Val
     450                 455                      460

Arg  Val  Leu  Val  Arg  Asn  Gly  Ala  Gln  Val  Asp  Ala  Ala  Ala
```

-continued

```
                          465                          470                          475
Arg  Glu  Leu  Gln  Thr  Pro  Leu  His  Ile  Ala  Ser  Arg  Leu  Gly
               480                      485                          490

Asn  Thr  Asp  Ile  Val  Ile  Leu  Leu  Gln  Ala  Asn  Ala  Ser
               495                      500

Pro  Asn  Ala  Ala  Thr  Arg  Asp  Leu  Tyr  Thr  Pro  Leu  His  Ile
505                 510                      515

Ala  Ala  Lys  Glu  Gly  Gln  Glu  Val  Ala  Ala  Ile  Leu  Met
     520                 525                      530

Asp  His  Gly  Thr  Asp  Lys  Thr  Leu  Leu  Thr  Lys  Lys  Gly  Phe
               535                 540                          545

Thr  Pro  Leu  His  Leu  Ala  Ala  Lys  Tyr  Gly  Asn  Leu  Pro  Val
               550                 555                               560

Ala  Lys  Ser  Leu  Leu  Glu  Arg  Gly  Thr  Pro  Val  Asp  Ile  Glu
                    565                      570

Gly  Lys  Asn  Gln  Val  Thr  Pro  Leu  His  Val  Ala  Ala  His  Tyr
575                      580                      585

Asn  Asn  Asp  Lys  Val  Ala  Leu  Leu  Leu  Glu  Asn  Gly  Ala
     590                      595                      600

Ser  Ala  His  Ala  Ala  Ala  Lys  Asn  Gly  Tyr  Thr  Pro  Leu  His
               605                      610                      615

Ile  Ala  Ala  Lys  Lys  Asn  Gln  Met  Asp  Ile  Ala  Ser  Thr  Leu
                    620                      625                          630

Leu  His  Tyr  Lys  Ala  Asn  Ala  Asn  Ala  Glu  Ser  Lys  Ala  Gly
                    635                           640

Phe  Thr  Pro  Leu  His  Leu  Ala  Ala  Gln  Glu  Gly  His  Arg  Glu
645                      650                           655

Met  Ala  Ala  Leu  Leu  Ile  Glu  Asn  Gly  Ala  Lys  Val  Gly  Ala
     660                      665                      670

Gln  Ala  Arg  Asn  Gly  Leu  Thr  Pro  Met  His  Leu  Cys  Ala  Gln
               675                      680                          685

Glu  Asp  Arg  Val  Ser  Val  Ala  Glu  Glu  Leu  Val  Lys  Glu  Asn
                    690                      695                          700

Ala  Ala  Ile  Asp  Pro  Lys  Thr  Lys  Ala  Gly  Tyr  Thr  Pro  Leu
                    705                      710

His  Val  Ala  Cys  His  Phe  Gly  Gln  Ile  Asn  Met  Val  Arg  Phe
715                      720                      725

Leu  Ile  Glu  His  Gly  Ala  Arg  Val  Ser  Val  Ile  Thr  Arg  Ala
     730                      735                      740

Ser  Tyr  Thr  Pro  Leu  His  Gln  Ala  Ala  Gln  Gly  His  Asn
          745                      750                      755

Ser  Val  Val  Arg  Tyr  Leu  Leu  Glu  His  Gly  Ala  Ser  Pro  Asn
               760                      765                          770

Val  His  Thr  Ser  Thr  Gly  Gln  Thr  Pro  Leu  Ser  Ile  Ala  Glu
                    775                      780

Arg  Leu  Gly  Tyr  Val  Ser  Val  Val  Glu  Ala  Leu  Lys  Thr  Ile
785                      790                      795

Thr  Glu  Thr  Thr  Val  Ile  Thr  Glu  Thr  Thr  Val  Thr  Glu
     800                      805                      810

Glu  Arg  Tyr  Lys  Pro  Gln  Asn  Pro  Glu  Ala  Met  Asn  Glu  Thr
               815                      820                          825

Met  Phe  Ser  Asp  Ser  Glu  Asp  Glu  Gly  Glu  Asp  Asn  Gln  Ile
                    830                      835                          840
```

```
Thr Ala Asn Ala His Ala His Asp Phe Ser Glu Ser Leu Thr
                845                 850

Lys Gly Leu His Asp Ser Thr Gly Val His Leu Ile His Ala
855                 860                 865

Thr Glu Pro Thr Leu Ser Arg Ser Pro Glu Val Glu Gly Thr
    870                 875                 880

Asp Gly Asp Leu Asp Ala Leu Ile Arg Lys Ala Gln His Glu
                885                 890                 895

Pro Ile Thr Thr Ala Met Ala Asp Pro Ser Leu Asp Ala Ser
                900                 905                 910

Leu Pro Asp Asn Val Thr Ile Met Arg Thr Thr Met Gln Pro
                    915                 920

Ser Phe Leu Ile Ser Phe Met Val Asp Ala Arg Gly Gly Ala
925                 930                 935

Met Arg Gly Cys Arg His Ser Gly Val Arg Ile Ile Ile Pro
    940                 945                 950

Pro Arg Lys Ala Pro Gln Pro Thr Arg Val Thr Cys Arg Tyr
        955                 960                 965

Leu Gly Lys Asp Lys Leu Ala His Pro Pro Leu Ser Glu
                970                 975                 980

Gly Glu Ala Leu Ala Ser Arg Ile Leu Glu Met Ala Pro His
                985                 990

Gly Ala Lys Phe Leu Gly Pro Val Ile Leu Glu Val Pro His
995                 1000                1005

Phe Ala Ser Leu Arg Gly Arg Glu Arg Glu Ile Val Ile Leu
    1010                1015                1020

Arg Ser Asp Asp Gly Gln His Trp Lys Glu His Gln Leu Glu
    1025                1030                1035

Ala Thr Glu Asp Ala Val Gln Glu Val Leu Asn Glu Ser Phe
                1040                1045                1050

Asp Ala Glu Glu Leu Ser Gln Leu Asp Asp Leu His Thr Ser
                1055                1060

Arg Ile Thr Arg Ile Leu Thr Asn Asp Phe Pro Met Tyr Phe
1065                1070                1075

Ala Val Val Thr Arg Val Arg Gln Glu Val His Cys Val Gly
    1080                1085                1090

Pro Glu Gly Gly Val Ile Leu Ser Ser Val Val Pro His Val
            1095                1100                1105

Gln Ala Ile Phe Pro Asp Gly Ser Leu Thr Lys Thr Ile Lys
            1110                1115                1120

Val Ser Val Gln Ala Gln Pro Val Pro Gln Glu Ile Val Thr
                1125                1130

Arg Leu His Gly Asn Arg Val Ala Val Ser Pro Ile Val Thr
1135                1140                1145

Val Glu Pro Arg Arg Arg Lys Phe His Lys Pro Ile Thr Leu
1150                1155                1160

Cys Ile Pro Leu Pro Gln Ser Ser Asn Lys Gly Met Leu Thr
        1165                1170                1175

Gln Tyr Ser Gly Gln Pro Gly Gln Glu Pro Pro Thr Leu Arg
                1180                1185                1190

Leu Leu Cys Ser Lys Thr Gly Gly Ser Ser Pro Ala Gln Trp
                1195                1200

Glu Asp Ile Thr Gly Thr Thr Gln Leu Thr Phe Thr Gly Glu
1205                1210                1215
```

```
Asp Val Ser Phe Thr Thr Thr Val Ser Ala Arg Phe Trp Leu
    1220                1225                1230

Met Asp Cys Gln Thr Pro Arg Asp Ala Ala Arg Met Ala Gln
        1235                1240                1245

Glu Val Tyr Asn Glu Ala Ile Ala Val Pro Tyr Met Ala Lys
            1250                1255                1260

Phe Leu Ile Phe Ala Arg Arg Thr Phe Pro Ala Glu Gly Gln
                1265                1270

Leu Arg Leu Phe Cys Met Thr Asp Asp Arg Glu Asp Lys Thr
1275                1280                1285

Leu Glu Lys Gln Glu Arg Phe Ile Glu Ile Ala Lys Ser Lys
    1290                1295                1300

Asp Val Glu Val Leu Ser Gly Arg His Gln Phe Leu Glu Phe
        1305                1310                1315

Ser Gly Asn Leu Leu Pro Ile Thr Lys Ser Gly Asp Gln Leu
            1320                1325                1330

Ser Leu Tyr Phe Leu Pro Phe Gln Glu Asn Arg Leu Ala Phe
                1335                1340

Met Val Lys Ile Arg Thr His Thr Asp Asn Glu Thr Ala Ala
1345                1350                1355

Asp Gly Arg Ile Val Phe Met Lys Glu Pro Lys Leu Arg Ala
    1360                1365                1370

Glu Asn Leu Pro Pro Gln Thr Pro Val Cys Thr Leu Ala Ile
        1375                1380                1385

Thr Leu Pro Glu Tyr Thr Gly Pro Glu Pro Met Val Ser Lys
            1390                1395                1400

Lys Leu Phe Tyr Ser Glu Ala Ser Leu Thr Glu Lys Tyr Val
                1405                1410

Gly Ala Phe His Glu Thr Ala Glu Pro Asp Asn Leu Pro Leu
1415                1420                1425

Ala His Val Ala Leu Leu Ile Gly Ala Asp Trp His Arg Leu
    1430                1435                1440

Ala Arg Ala Leu Glu Val Pro Asp Ile Asp Ile Arg Gln Val
        1445                1450                1455

Arg His Gln Leu Val Gly Leu Glu Ala Val Thr Ile Leu Arg
            1460                1465                1470

Ile Trp Ile Phe Leu Lys Lys Glu Gln Ala Thr Pro Val Ala
                1475                1480

Leu Arg Ser Ala Leu Gln Arg Ile Gly Arg Asp Asp Val Val
1485                1490                1495

Arg Glu Met Asp Arg Ala Glu Lys Leu Asp Gly Leu Glu Gly
    1500                1505                1510

Thr Pro Val Ser His Ile Ser Gly Pro Ser Ile Thr Leu Ser
        1515                1520                1525

Ser Thr Leu Leu Glu Val Ala Gly Asp Arg Arg Arg His Ala
            1530                1535                1540

Glu Val Thr Met Ala Gln Gln Arg Leu Ala Gln Glu Pro Phe
                1545                1550

Phe Gln Gln Val Gly Tyr Asn Gly Thr Pro Gly Asp Pro Glu
1555                1560                1565

Glu Pro Lys Glu Gln Ser Phe His Glu Glu Glu Glu Glu Val
    1570                1575                1580

Ala Val Ser Glu Ile Arg Thr Val Val Arg Thr Glu Arg His
```

```
                              1585                        1590                        1595
Val  His  Asp  Ser  Glu  Asn  Gly  Pro  Ile  Val  Glu  Glu  Arg  Thr
                    1600                      1605                      1610

Ile  Thr  Thr  Thr  Tyr  Glu  Asp  Asp  Val  Ala  Val  Asn  Glu  Glu
                    1615                      1620

Glu  Ile  Val  Asp  Lys  Ile  Val  Pro  Leu  Asn  Glu  Glu  Glu  Gln
1625                     1630                      1635

Glu  Lys  Trp  Asp  Arg  Met  Val  Arg  Glu  Val  Glu  Met  Asn  Phe
     1640                     1645                      1650

Glu  Gln  Gln  Glu  Thr  Ser  Lys  Glu  Gly  Thr  Phe  Gly  Cys  Gln
          1655                     1660                      1665

Thr  Thr  His  Glu  Lys  Glu  Lys  Asp  Asp  Asp  Gly  Gly  Ser  Leu
               1670                     1675                      1680

Lys  Thr  Thr  Met  Lys  Asp  Ser  His  Val  Arg  Gln  Ile  Phe  Phe
                    1685                     1690

Asp  Gly  Gly  Glu  Thr  Ser  Ala  Asn  Glu  Thr  Gly  Leu  Ser  Ser
1695                     1700                     1705

Gly  Asp  Ala  Asp  Thr  Ile  Met  Thr  Pro  Thr  Thr  Lys  Glu  Asp
     1710                     1715                     1720

Asn  His  Val  Ile  Asp  Val  Met  Glu  Glu  Arg  Arg  Thr  Asp  Glu
               1725                     1730                     1735

Glu  Ala  Lys  Gly  Gln  Ser  Val  His  Glu
```

( 2 ) INFORMATION FOR SEQ ID NO:34:

( i ) SEQUENCE CHARACTERISTICS:
        ( A ) LENGTH: 5503 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

```
TTTTTTTTT   TTTTTTTTT   TTTTACTGGA   GCAAATTTAT   CAAGAGTAGC          50

AGTTACAGAC  TACAGCAAAA  ACAAAAGTG   AATGGACGAT   GGAAAACGCT         100

TTAACAATAT  GGGAAGCCCA  AACAGCATTC  AAATTATTGC   TTTGAAAAAT         150

TTCATTAAAT  ATTAGCAACA  TAGGCATGTG  CGAGATTGCG   ATTTAAATCA         200

ATTTGTGGAT  CCAGATTATT  CATGAACGCT  TTGCCCTTTG   GCCTCTTCAT         250

CAGTTCGCCT  TTCCTCCATT  ACGTCTATAA  CATGATTATC   CTCCTTTGTC         300

GTTGGAGTCA  TAATAGTGTC  TGCATCCCCG  CTACTTAATC   CTGTTTCATT         350

AGCGGATGTC  TCACCTCCAT  CGAAGAAAAT  CTGCCTTACG   TGACTATCTT         400

TCATTGTCGT  CTTCAGACTG  CCACCATCAT  CATCTTTTTC   TTTCTCATGT         450

GTTGTCTGAC  AACCAAACGT  TCCTTCTTTT  GATGTTTCTT   GTTGCTCAAA         500

ATTCATTTCC  ACTTCTCGAA  CCATTCGATC  CCATTTTTCT   TGCTCCTCTT         550

CGTTGAGAGG  CACTATTTTG  TCAACAATTT  CTTCTTCGTT   TACAGCAACA         600

TCATCCTCAT  ACGTAGTTGT  TATTGTACGC  TCTTCCACAA   TAGGACCATT         650

TTCCGAATCA  TGCACATGTC  GTTCAGTGCG  CACAACTGTT   CGAATTTCTG         700

AAACTGCAAC  TTCCTCTTCC  TCTTCGTGGA  ATGACTGTTC   TTTGGGTTCT         750

TCTGGATCTC  CAGGTGTCCC  ATTATACCCT  ACTTGCTGAA   AAAACGGTTC         800

TTGTGCCAAT  CGCTGTTGCG  CCATTGTTAC  CTCGGCGTGA   CGACGTCTGT         850
```

| | | | | | |
|---|---|---|---|---|---|
| CGCCTGCTAC | CTCTAGCAAA | GTAGATGACA | GAGTTATTGA | GGGTCCAGAA | 900 |
| ATATGCGATA | CAGGTGTTCC | TTCTAAACCA | TCTAGCTTTT | CAGCTCGATC | 950 |
| CATTTCTCGT | ACAACATCAT | CACGTCCTAT | TCGCTGCAAT | GCTGATCGCA | 1000 |
| AAGCAACGGG | CGTAGCTTGT | TCTTTCTTCA | AAAATATCCA | AATACGTAGA | 1050 |
| ATAGTGACTG | CTTCAAGACC | AACTAGTTGA | TGTCGAACTT | GTCGTATATC | 1100 |
| AATATCAGGT | ACTTCAAGCG | CTCGAGCTAA | CCGATGCCAA | TCAGCGCCAA | 1150 |
| TTAATAGTGC | AACATGTGCT | AGTGGCAAGT | TATCAGGTTC | AGCAGTTTCA | 1200 |
| TGGAAAGCTC | CAACGTATTT | CTCAGTCAAA | GAAGCTTCCG | AATAGAAGAG | 1250 |
| TTTTTTGGAA | ACCATCGGCT | CCGGCCCAGT | GTATTCCGGA | AGAGTGATTG | 1300 |
| CAAGAGTACA | CACTGGCGTC | TGCGGAGGTA | AATTTTCGGC | TCTCAATTTT | 1350 |
| GGTTCTTTCA | TAAATACTAT | CCGGCCATCA | GCTGCAGTTT | CGTTGTCCGT | 1400 |
| GTGAGTGCGT | ATCTTTACCA | TGAAAGCAAG | ACGATTTTCT | TGGAATGGTA | 1450 |
| GAAAATAAAG | AGAAAGTTGG | TCACCACTCT | TGGTTATTGG | AAGAAGATTT | 1500 |
| CCAGAAAATT | CCAAAAACTG | ATGTCGCCCA | CTTAAGACTT | CTACATCTTT | 1550 |
| CGATTTCGCA | ATTTCAATGA | AACGTTCTTG | TTTTTCCAGG | GTTTTATCTT | 1600 |
| CCCGATCATC | AGTCATACAA | AACAATCTCA | ACTGTCCTTC | GGCAGGAAAA | 1650 |
| GTTCGTCGAG | CAAAAATAAG | AAATTTAGCC | ATATAAGGAA | CTGCAATTGC | 1700 |
| TTCATTGTAA | ACTTCTTGTG | CCATTCGTGC | CGCATCTCGC | GGAGTTTGGC | 1750 |
| AATCCATCAA | CCAAAATCGA | GCAGAAACCG | TAGTTGTAAA | TGAAACGTCC | 1800 |
| TCACCAGTAA | ATGTTAACTG | GGTAGTTCCA | GTAATATCTT | CCCACTGTGC | 1850 |
| AGGAGAAGAA | CCTCCAGTTT | TACTGCAGAG | TAAACGCAGC | GTCGGTGGTT | 1900 |
| CCTGTCCTGG | TTGGCCACTA | TATTGTGTTA | ACATTCCTTT | ATTTGAGCTT | 1950 |
| TGTGGCAATG | GTATGCACAG | CGTTATGGGC | TTATGGAATT | TGCGACGACG | 2000 |
| CGGTTCAACA | GTTACAATTG | GAGAAACAGC | GACTCTATTC | CCATGTAAAC | 2050 |
| GAGTGACTAT | CTCTTGTGGA | ACTGGCTGGG | CTTGCACAGA | TACTTTGATC | 2100 |
| GTCTTAGTCA | AGGAACCATC | CGGAAATATG | GCCTGCACAT | GAGGAACAAC | 2150 |
| TGAAGAGAGT | ATTACACCAC | CTTCTGGACC | AACACAGTGC | ACTTCTTGCC | 2200 |
| GCACACGAGT | AACGACCGCG | AAATACATTG | GGAAATCATT | GGTCAGGATA | 2250 |
| CGCGTAATCC | GTGATGTATG | CAAATCATCA | AGTTGCGACA | ACTCTTCTGC | 2300 |
| ATCAAACGAT | TCATTGAGCA | CCTCTTGTAC | AGCATCTTCT | GTTGCTTCAA | 2350 |
| GCTGATGCTC | TTTCCAATGC | TGCCCATCAT | CAGAACGCAA | AATGACAATC | 2400 |
| TCTCTCTCTC | GTCCACGAAG | TGATGCAAAA | TGTGGTACTT | CCAATATAAC | 2450 |
| AGGGCCTAAG | AATTTTGCTC | CATGTGGTGC | CATTTCAAGT | ATACGTGANG | 2500 |
| CGAGCGCTTC | ACCTTCACTT | AATGGTGGTG | GATGCGCTAA | CTTGTCCTTT | 2550 |
| CCAAGGTATC | TGCATGTGAC | CCGTGTAGGT | TGCGGCGCTT | CCTCGGTGG | 2600 |
| TATAATGATT | CTGACACCGG | AATGCCTACA | ACCACGCATT | GCTCCTCCAC | 2650 |
| GTGCATCCAC | CATAAACGAA | ATTAAAAAAC | TAGGTTGCAT | GGTAGTTCTC | 2700 |
| ATTATCGTAA | CATTGTCAGG | AAGCGATGCA | TCTAAGGAAG | GATCGGCCAT | 2750 |
| CGCTGTAGTA | ATTGGTTCAT | GTTGTGCTTT | ACGAATTAAG | GCATCCAAAT | 2800 |
| CGCCATCCGT | ACCTTCCACT | TCCGGACTTC | GTGACAATGT | CGGTTCTGTG | 2850 |

```
GCATGAATCA  AATGTACACC  AGTTGAATCG  TGCAAACCTT  TTGTGAGGCT    2900
TTCTGAGAAA  TCATGAGCAT  GAGCATTGGC  TGTGATCTGA  TTATCTTCAC    2950
CTTCATCTTC  GGAATCGGAA  AACATGGTTT  CATTCATTGC  TTCGGGATTC    3000
TGAGGTTTAT  ATCTTTCTTC  AGTAACGGTT  GTGGTCTCCG  TTATCACAGT    3050
AGTCTCGGTA  ATTGTTTTAA  GCGCTTCAAC  CACGGATACA  TACCCTAGAC    3100
GTTCAGCAAT  CGATAATGGA  GTTTGTCCTG  TCGATGTATG  AACATTTGGA    3150
CTTGCACCAT  GTTCCAACAA  GTAACGTACA  ACACTGTTAT  GCCCTTGCTG    3200
AGCAGCTTGA  TGCAGAGGAG  TATAGGAAGC  ACGAGTAATA  ACTGAAACTC    3250
GTGCGCCATG  CTCAATCAAG  AAACGGACCA  TGTTTATTTG  TCCAAAATGG    3300
CAAGCAACAT  GTAACGGCGT  ATATCCTGCT  TTCGTTTTGG  GATCAATGGC    3350
TGCGTTTTCT  TTCACTAGTT  CTTCTGCTAC  GCTCACACGA  TCCTCCTGTG    3400
CACATAAATG  CATTGGTGTC  AAGCCATTCC  TTGCCTGAGC  TCCAACTTTT    3450
GCTCCATTTT  CAATTAATAA  CGCAGCCATT  TCGCGATGGC  CCTCCTGGGC    3500
GGCAAGATGA  AGTGGTGTAA  AGCCAGCTTT  GCTTTCAGCA  TTCGCATTTG    3550
CCTTATAATG  AAGGAGAGTG  CTAGCAATAT  CCATCTGATT  CTTCTTCGCG    3600
GCAATATGTA  AAGGAGTGTA  CCCATTCTTG  GCAGCGGCAT  GTGCAGAAGC    3650
ACCATTTTCT  AGAAGTAACA  ATGCTACCTT  GTCGTTATTG  TAATGTGCCG    3700
CTACATGCAG  AGGTGTTACC  TGATTCTTGC  CTTCAATGTC  AACCGGTGTT    3750
CCTCGTTCTA  GCAATGATTT  CGCGACCGGC  AAATTGCCAT  ACTTAGCAGC    3800
TAAATGCAAC  GGCGTAAAAC  CCTTTTTCGT  GAGCAGTGTC  TTGTCGGTTC    3850
CATGATCCAT  CAATATTGCT  GCCACTTCCT  CTTGCCCCTC  CTTGGCAGCA    3900
ATATGAAGAG  GAGTATAAAG  ATCTCTTGTG  GCAGCATTTG  GTGATGCATT    3950
AGCCTGCAGC  AACAAAATGA  CGATGTCGGT  ATTACCAAGA  CGTGATGCAA    4000
TGTGCAGTGG  AGTTTGTAGT  TCACGAGCAG  CAGCATCCAC  CTGTGCTCCA    4050
TTACGCACCA  AAACACGAAC  AATGTCCGTT  TGGTTTGCTC  GTGCAGCTAA    4100
ATGAAGAGGC  GTTTCACCGC  GTACTGTAGC  CACATCTGCA  TTAGCACCTT    4150
GTTGTAGTAA  ATAGATGACA  ATGTTTATAG  CACCCATAAA  AGCAGCGACA    4200
TGCAGCGGTG  AGAGACCGGA  TTCAGTAGTT  GCTTCGATTG  CAGCGTGGTA    4250
TTTCAGTAGC  AGTTCGACAA  TTTTAATGCG  ATTTTTTTTG  CAAGCGATAT    4300
GCAGCGGTGT  GAAGCCATTG  AGAGCTCGAG  CATTCGGGTC  AGCATTACGA    4350
TCCAGCAAAA  GTTTAGCGAC  ACGGACATGT  CCGCAATGAG  CAGCCACATG    4400
AAGAGGAGTG  AGATAGTCAA  CAGTAACATC  ATCCACCTGT  GCTGCCATAT    4450
GTAAGGGAGC  CAAACCATTT  TTTGTCTTAG  CACTGATTGG  AGCTCCTTTT    4500
TCAAGCAACA  AATCAACAAC  TTGATCATGA  CCTGAACGAG  AAGCACAGTG    4550
TAATGGTGTT  AGTAAATCAC  GTGTGCGACA  GTCAATTACG  GCCCCATGAG    4600
CCAACAATAA  CGAAACCATG  TTTGTACGAC  CCCATTTTGT  TGCAACGTGT    4650
AACGGACTTA  TGTTATGTCT  CGCTTGGTAA  TTCACATTGG  CTCCCTTTTC    4700
GAGTAGCAGT  TGTGCTACGT  TCTCATTTCC  ATAGTGAGCG  GCGATATGAA    4750
GCGGAGTAAA  GCCGCTTTTC  GAAGTCACAT  CCGAGTTATG  CTCATTTTGA    4800
AGTAATAGCG  TAGCTGCTTT  CGTATCATCT  TTTTTAGCAG  CAATATGCAG    4850
```

-continued

| | | | | | |
|---|---|---|---|---|---|
| TGCTGGCAAG | CGCACTTTCC | CGCGCGTGTC | ATTTTCAAGC | AAAACAGCGA | 4900 |
| CCACACGATC | GTGACCTTGT | TGCAAGGCAA | CTGCCAGTGG | CGTAAAACCG | 4950 |
| TCTTCTGTAC | TTAAAGCTTG | ATTGGCATTG | TGGGCAAGAA | GATAGCGTAC | 5000 |
| AACAGATTCG | TGATTTTCTT | GTGCAGCCAT | GTAAAGTGGT | GTAAAACCGT | 5050 |
| TTAGTGATTG | TACGTTAACA | TTAGCACCAT | TTTCAACAAG | TACTGTGACG | 5100 |
| ATTAGTTCTT | GTCCTGCCAA | TGATGCTATA | TGTAACGCTG | TGTTACCCTT | 5150 |
| TCTAGTGGCA | GCATAACAT | CTGCTTTCT | TTTCAGAAGT | TCGCGGACCA | 5200 |
| CTTCATGATG | ACCTTCTTTG | GAGGCCAGAT | GCAATGCATT | AAGGCCATTC | 5250 |
| GCATTGCATG | TGTTGATATC | GGTGCCCGAA | CGAAGTAGTT | CAAGTACACG | 5300 |
| ATCCAAATTT | CCAGCTCTTG | CTGCTCGTAA | AAAACTTGCA | CTGCTCTCAC | 5350 |
| CTTTGTTGGA | ATGTTGACTG | TTATCATCAG | GAATTTGTTG | TTGATGTTGT | 5400 |
| GAATCTTTTG | GTTCTGCGGG | CCAGCCACTT | CCCTCGACTA | TAGGATTACT | 5450 |
| CATCAATAGT | TGAGTTATAT | CAGTCAGCCG | CCTCAAACTT | GGGTAATTAA | 5500 |
| ACC | | | | | 5503 |

( 2 ) INFORMATION FOR SEQ ID NO:35:

( i ) SEQUENCE CHARACTERISTICS:
        ( A ) LENGTH: 5235 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

| | | | | | |
|---|---|---|---|---|---|
| ATGAGTAATC | CTATAGTCGA | GGGAAGTGGC | TGGCCCGCAG | AACCAAAAGA | 50 |
| TTCACAACAT | CAACAACAAA | TTCCTGATGA | TAACAGTCAA | CATTCCAACA | 100 |
| AAGGTGAGAG | CAGTGCAAGT | TTTTTACGAG | CAGCAAGAGC | TGGAAATTTG | 150 |
| GATCGTGTAC | TTGAACTACT | TCGTTCGGGC | ACCGATATCA | ACACATGCAA | 200 |
| TGCGAATGGC | CTTAATGCAT | TGCATCTGGC | CTCCAAAGAA | GGTCATCATG | 250 |
| AAGTGGTCCG | CGAACTTCTG | AAAAGAAAAG | CAGATGTTGA | TGCTGCCACT | 300 |
| AGAAAGGGTA | ACACAGCGTT | ACATATAGCA | TCATTGGCAG | GACAAGAACT | 350 |
| AATCGTCACA | GTACTTGTTG | AAAATGGTGC | TAATGTTAAC | GTACAATCAC | 400 |
| TAAACGGTTT | TACACCACTT | TACATGGCTG | CACAAGAAAA | TCACGAATCT | 450 |
| GTTGTACGCT | ATCTTCTTGC | CCACAATGCC | AATCAAGCTT | TAAGTACAGA | 500 |
| AGACGGTTTT | ACGCCACTGG | CAGTTGCCTT | GCAACAAGGT | CACGATCGTG | 550 |
| TGGTCGCTGT | TTTGCTTGAA | AATGACACGC | GCGGGAAAGT | GCGCTTGCCA | 600 |
| GCACTGCATA | TTGCTGCTAA | AAAAGATGAT | ACGAAAGCAG | CTACGCTATT | 650 |
| ACTTCAAAAT | GAGCATAACT | CGGATGTGAC | TTCGAAAGC | GGCTTTACTC | 700 |
| CGCTTCATAT | CGCCGCTCAC | TATGGAAATG | AGAACGTAGC | ACAACTGCTA | 750 |
| CTCGAAAAGG | GAGCCAATGT | GAATTACCAA | GCGAGACATA | ACATAAGTCC | 800 |
| GTTACACGTT | GCAACAAAAT | GGGGTCGTAC | AAACATGGTT | TCGTTATTGT | 850 |
| TGGCTCATGG | GGCCGTAATT | GACTGTCGCA | CACGTGATTT | ACTAACACCA | 900 |
| TTACACTGTG | CTTCTCGTTC | AGGTCATGAT | CAAGTTGTTG | ATTTGTTGCT | 950 |
| TGAAAAAGGA | GCTCCAATCA | GTGCTAAGAC | AAAAAATGGT | TTGGCTCCCT | 1000 |

```
TACATATGGC  AGCACAGGTG  GATGATGTTA  CTGTTGACTA  TCTCACTCCT      1050
CTTCATGTGG  CTGCTCATTG  CGGACATGTC  CGTGTCGCTA  AACTTTTGCT      1100
GGATCGTAAT  GCTGACCCGA  ATGCTCGAGC  TCTCAATGGC  TTCACACCGC      1150
TGCATATCGC  TTGCAAAAAA  AATCGCATTA  AAATTGTCGA  ACTGCTACTG      1200
AAATACCACG  CTGCAATCGA  AGCAACTACT  GAATCCGGTC  TCTCACCGCT      1250
GCATGTCGCT  GCTTTTATGG  GTGCTATAAA  CATTGTCATC  TATTTACTAC      1300
AACAAGGTGC  TAATGCAGAT  GTGGCTACAG  TACGCGGTGA  AACGCCTCTT      1350
CATTTAGCTG  CACGAGCAAA  CCAAACGGAC  ATTGTTCGTG  TTTTGGTGCG      1400
TAATGGAGCA  CAGGTGGATG  CTGCTGCTCG  TGAACTACAA  ACTCCACTGC      1450
ACATTGCATC  ACGTCTTGGT  AATACCGACA  TCGTCATTTT  GTTGCTGCAG      1500
GCTAATGCAT  CACCAAATGC  TGCCACAAGA  GATCTTTATA  CTCCTCTTCA      1550
TATTGCTGCC  AAGGAGGGGC  AAGAGGAAGT  GGCAGCAATA  TTGATGGATC      1600
ATGGAACCGA  CAAGACACTG  CTCACGAAAA  AGGGTTTTAC  GCCGTTGCAT      1650
TTAGCTGCTA  AGTATGGCAA  TTTGCCGGTC  GCGAAATCAT  TGCTAGAACG      1700
AGGAACACCG  GTTGACATTG  AAGGCAAGAA  TCAGGTAACA  CCTCTGCATG      1750
TAGCGGCACA  TTACAATAAC  GACAAGGTAG  CATTGTTACT  TCTAGAAAAT      1800
GGTGCTTCTG  CACATGCCGC  TGCCAAGAAT  GGGTACACTC  CTTTACATAT      1850
TGCCGCGAAG  AAGAATCAGA  TGGATATTGC  TAGCACTCTC  CTTCATTATA      1900
AGGCAAATGC  GAATGCTGAA  AGCAAAGCTG  GCTTTACACC  ACTTCATCTT      1950
GCCGCCCAGG  AGGGCCATCG  CGAAATGGCT  GCGTTATTAA  TTGAAAATGG      2000
AGCAAAAGTT  GGAGCTCAGG  CAAGGAATGG  CTTGACACCA  ATGCATTTAT      2050
GTGCACAGGA  GGATCGTGTG  AGCGTAGCAG  AAGAACTAGT  GAAAGAAAAC      2100
GCAGCCATTG  ATCCCAAAAC  GAAAGCAGGA  TATACGCCGT  TACATGTTGC      2150
TTGCCATTTT  GGACAAATAA  ACATGGTCCG  TTTCTTGATT  GAGCATGGCG      2200
CACGAGTTTC  AGTTATTACT  CGTGCTTCCT  ATACTCCTCT  GCATCAAGCT      2250
GCTCAGCAAG  GGCATAACAG  TGTTGTACGT  TACTTGTTGG  AACATGGTGC      2300
AAGTCCAAAT  GTTCATACAT  CGACAGGACA  AACTCCATTA  TCGATTGCTG      2350
AACGTCTAGG  GTATGTATCC  GTGGTTGAAG  CGCTTAAAAC  AATTACCGAG      2400
ACTACTGTGA  TAACGGAGAC  CACAACCGTT  ACTGAAGAAA  GATATAAACC      2450
TCAGAATCCC  GAAGCAATGA  ATGAAACCAT  GTTTTCCGAT  TCCGAAGATG      2500
AAGGTGAAGA  TAATCAGATC  ACAGCCAATG  CTCATGCTCA  TGATTTCTCA      2550
GAAAGCCTCA  CAAAAGGTTT  GCACGATTCA  ACTGGTGTAC  ATTTGATTCA      2600
TGCCACAGAA  CCGACATTGT  CACGAAGTCC  GGAAGTGGAA  GGTACGGATG      2650
GCGATTTGGA  TGCCTTAATT  CGTAAAGCAC  AACATGAACC  AATTACTACA      2700
GCGATGGCCG  ATCCTTCCTT  AGATGCATCG  CTTCCTGACA  ATGTTACGAT      2750
AATGAGAACT  ACCATGCAAC  CTAGTTTTTT  AATTTCGTTT  ATGGTGGATG      2800
CACGTGGAGG  AGCAATGCGT  GGTTGTAGGC  ATTCCGGTGT  CAGAATCATT      2850
ATACCACCGA  GGAAAGCGCC  GCAACCTACA  CGGGTCACAT  GCAGATACCT      2900
TGGAAAGGAC  AAGTTAGCGC  ATCCACCACC  ATTAAGTGAA  GGTGAAGCGC      2950
TCGCNTCACG  TATACTTGAA  ATGGCACCAC  ATGGAGCAAA  ATTCTTAGGC      3000
```

| | | | | | |
|---|---|---|---|---|---|
| CCTGTTATAT | TGGAAGTACC | ACATTTTGCA | TCACTTCGTG | GACGAGAGAG | 3050 |
| AGAGATTGTC | ATTTTGCGTT | CTGATGATGG | GCAGCATTGG | AAAGAGCATC | 3100 |
| AGCTTGAAGC | AACAGAAGAT | GCTGTACAAG | AGGTGCTCAA | TGAATCGTTT | 3150 |
| GATGCAGAAG | AGTTGTCGCA | ACTTGATGAT | TTGCATACAT | CACGGATTAC | 3200 |
| GCGTATCCTG | ACCAATGATT | TCCCAATGTA | TTTCGCGGTC | GTTACTCGTG | 3250 |
| TGCGGCAAGA | AGTGCACTGT | GTTGGTCCAG | AAGGTGGTGT | AATACTCTCT | 3300 |
| TCAGTTGTTC | CTCATGTGCA | GGCCATATTT | CCGGATGGTT | CCTTGACTAA | 3350 |
| GACGATCAAA | GTATCTGTGC | AAGCCCAGCC | AGTTCCACAA | GAGATAGTCA | 3400 |
| CTCGTTTACA | TGGGAATAGA | GTCGCTGTTT | CTCCAATTGT | AACTGTTGAA | 3450 |
| CCGCGTCGTC | GCAAATTCCA | TAAGCCCATA | ACGCTGTGCA | TACCATTGCC | 3500 |
| ACAAAGCTCA | AATAAGGAA | TGTTAACACA | ATATAGTGGC | CAACCAGGAC | 3550 |
| AGGAACCACC | GACGCTGCGT | TTACTCTGCA | GTAAAACTGG | AGGTTCTTCT | 3600 |
| CCTGCACAGT | GGGAAGATAT | TACTGGAACT | ACCCAGTTAA | CATTTACTGG | 3650 |
| TGAGGACGTT | TCATTTACAA | CTACGGTTTC | TGCTCGATTT | TGGTTGATGG | 3700 |
| ATTGCCAAAC | TCCGCGAGAT | GCGGCACGAA | TGGCACAAGA | AGTTTACAAT | 3750 |
| GAAGCAATTG | CAGTTCCTTA | TATGGCTAAA | TTTCTTATTT | TTGCTCGACG | 3800 |
| AACTTTTCCT | GCCGAAGGAC | AGTTGAGATT | GTTTTGTATG | ACTGATGATC | 3850 |
| GGGAAGATAA | AACCCTGGAA | AAACAAGAAC | GTTTCATTGA | AATTGCGAAA | 3900 |
| TCGAAAGATG | TAGAAGTCTT | AAGTGGGCGA | CATCAGTTTT | TGGAATTTTC | 3950 |
| TGGAAATCTT | CTTCCAATAA | CCAAGAGTGG | TGACCAACTT | TCTCTTTATT | 4000 |
| TTCTACCATT | CCAAGAAAAT | CGTCTTGCTT | TCATGGTAAA | GATACGCACT | 4050 |
| CACACGGACA | ACGAAACTGC | AGCTGATGGC | CGGATAGTAT | TTATGAAAGA | 4100 |
| ACCAAAATTG | AGAGCCGAAA | ATTTACCTCC | GCAGACGCCA | GTGTGTACTC | 4150 |
| TTGCAATCAC | TCTTCCGGAA | TACACTGGGC | CGGAGCCGAT | GGTTTCCAAA | 4200 |
| AAACTCTTCT | ATTCGGAAGC | TTCTTTGACT | GAGAAATACG | TTGGAGCTTT | 4250 |
| CCATGAAACT | GCTGAACCTG | ATAACTTGCC | ACTAGCACAT | GTTGCACTAT | 4300 |
| TAATTGGCGC | TGATTGGCAT | CGGTTAGCTC | GAGCGCTTGA | AGTACCTGAT | 4350 |
| ATTGATATAC | GACAAGTTCG | ACATCAACTA | GTTGGTCTTG | AAGCAGTCAC | 4400 |
| TATTCTACGT | ATTTGGATAT | TTTTGAAGAA | AGAACAAGCT | ACGCCCGTTG | 4450 |
| CTTTGCGATC | AGCATTGCAG | CGAATAGGAC | GTGATGATGT | TGTACGAGAA | 4500 |
| ATGGATCGAG | CTGAAAAGCT | AGATGGTTTA | GAAGGAACAC | CTGTATCGCA | 4550 |
| TATTTCTGGA | CCCTCAATAA | CTCTGTCATC | TACTTTGCTA | GAGGTAGCAG | 4600 |
| GCGACAGACG | TCGTCACGCC | GAGGTAACAA | TGGCGCAACA | GCGATTGGCA | 4650 |
| CAAGAACCGT | TTTTTCAGCA | AGTAGGGTAT | AATGGGACAC | CTGGAGATCC | 4700 |
| AGAAGAACCC | AAAGAACAGT | CATTCCACGA | AGAGGAAGAG | GAAGTTGCAG | 4750 |
| TTTCAGAAAT | TCGAACAGTT | GTGCGCACTG | AACGACATGT | GCATGATTCG | 4800 |
| GAAAATGGTC | CTATTGTGGA | AGAGCGTACA | ATAACAACTA | CGTATGAGGA | 4850 |
| TGATGTTGCT | GTAAACGAAG | AAGAAATTGT | TGACAAAATA | GTGCCTCTCA | 4900 |
| ACGAAGAGGA | GCAAGAAAAA | TGGGATCGAA | TGGTTCGAGA | AGTGGAAATG | 4950 |
| AATTTTGAGC | AACAAGAAAC | ATCAAAAGAA | GGAACGTTTG | GTTGTCAGAC | 5000 |

| | | | | | |
|---|---|---|---|---|---|
| AACACATGAG | AAAGAAAAAG | ATGATGATGG | TGGCAGTCTG | AAGACGACAA | 5050 |
| TGAAAGATAG | TCACGTAAGG | CAGATTTTCT | TCGATGGAGG | TGAGACATCC | 5100 |
| GCTAATGAAA | CAGGATTAAG | TAGCGGGGAT | GCAGACACTA | TTATGACTCC | 5150 |
| AACGACAAAG | GAGGATAATC | ATGTTATAGA | CGTAATGGAG | GAAAGGCGAA | 5200 |
| CTGATGAAGA | GGCCAAAGGG | CAAAGCGTTC | ATGAA | | 5235 |

( 2 ) INFORMATION FOR SEQ ID NO:36:

( i ) SEQUENCE CHARACTERISTICS:
        ( A ) LENGTH: 5235 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

| | | | | | |
|---|---|---|---|---|---|
| TTCATGAACG | CTTTGCCCTT | TGGCCTCTTC | ATCAGTTCGC | CTTTCCTCCA | 50 |
| TTACGTCTAT | AACATGATTA | TCCTCCTTTG | TCGTTGGAGT | CATAATAGTG | 100 |
| TCTGCATCCC | CGCTACTTAA | TCCTGTTTCA | TTAGCGGATG | TCTCACCTCC | 150 |
| ATCGAAGAAA | ATCTGCCTTA | CGTGACTATC | TTTCATTGTC | GTCTTCAGAC | 200 |
| TGCCACCATC | ATCATCTTTT | TCTTTCTCAT | GTGTTGTCTG | ACAACCAAAC | 250 |
| GTTCCTTCTT | TTGATGTTTC | TTGTTGCTCA | AAATTCATTT | CCACTTCTCG | 300 |
| AACCATTCGA | TCCCATTTTT | CTTGCTCCTC | TTCGTTGAGA | GGCACTATTT | 350 |
| TGTCAACAAT | TTCTTCTTCG | TTTACAGCAA | CATCATCCTC | ATACGTAGTT | 400 |
| GTTATTGTAC | GCTCTTCCAC | AATAGGACCA | TTTTCCGAAT | CATGCACATG | 450 |
| TCGTTCAGTG | CGCACAACTG | TTCGAATTTC | TGAAACTGCA | ACTTCCTCTT | 500 |
| CCTCTTCGTG | GAATGACTGT | TCTTTGGGTT | CTTCTGGATC | TCCAGGTGTC | 550 |
| CCATTATACC | CTACTTGCTG | AAAAAACGGT | TCTTGTGCCA | ATCGCTGTTG | 600 |
| CGCCATTGTT | ACCTCGGCGT | GACGACGTCT | GTCGCCTGCT | ACCTCTAGCA | 650 |
| AAGTAGATGA | CAGAGTTATT | GAGGGTCCAG | AAATATGCGA | TACAGGTGTT | 700 |
| CCTTCTAAAC | CATCTAGCTT | TTCAGCTCGA | TCCATTTCTC | GTACAACATC | 750 |
| ATCACGTCCT | ATTCGCTGCA | ATGCTGATCG | CAAAGCAACG | GGCGTAGCTT | 800 |
| GTTCTTTCTT | CAAAAATATC | CAAATACGTA | GAATAGTGAC | TGCTTCAAGA | 850 |
| CCAACTAGTT | GATGTCGAAC | TTGTCGTATA | TCAATATCAG | GTACTTCAAG | 900 |
| CGCTCGAGCT | AACCGATGCC | AATCAGCGCC | AATTAATAGT | GCAACATGTG | 950 |
| CTAGTGGCAA | GTTATCAGGT | TCAGCAGTTT | CATGGAAAGC | TCCAACGTAT | 1000 |
| TTCTCAGTCA | AAGAAGCTTC | CGAATAGAAG | AGTTTTTTGG | AAACCATCGG | 1050 |
| CTCCGGCCCA | GTGTATTCCG | GAAGAGTGAT | TGCAAGAGTA | CACACTGGCG | 1100 |
| TCTGCGGAGG | TAAATTTTCG | GCTCTCAATT | TTGGTTCTTT | CATAAATACT | 1150 |
| ATCCGGCCAT | CAGCTGCAGT | TTCGTTGTCC | GTGTGAGTGC | GTATCTTTAC | 1200 |
| CATGAAAGCA | AGACGATTTT | CTTGGAATGG | TAGAAAATAA | AGAGAAAGTT | 1250 |
| GGTCACCACT | CTTGGTTATT | GGAAGAAGAT | TTCCAGAAAA | TTCCAAAAAC | 1300 |
| TGATGTCGCC | CACTTAAGAC | TTCTACATCT | TTCGATTTCG | CAATTTCAAT | 1350 |
| GAAACGTTCT | TGTTTTTCCA | GGGTTTTATC | TTCCCGATCA | TCAGTCATAC | 1400 |

| | | | | |
|---|---|---|---|---|
| AAAACAATCT | CAACTGTCCT | TCGGCAGGAA | AAGTTCGTCG | AGCAAAAATA | 1450 |
| AGAAATTTAG | CCATATAAGG | AACTGCAATT | GCTTCATTGT | AAACTTCTTG | 1500 |
| TGCCATTCGT | GCCGCATCTC | GCGGAGTTTG | GCAATCCATC | AACCAAAATC | 1550 |
| GAGCAGAAAC | CGTAGTTGTA | AATGAAACGT | CCTCACCAGT | AAATGTTAAC | 1600 |
| TGGGTAGTTC | CAGTAATATC | TTCCCACTGT | GCAGGAGAAG | AACCTCCAGT | 1650 |
| TTTACTGCAG | AGTAAACGCA | GCGTCGGTGG | TTCCTGTCCT | GGTTGGCCAC | 1700 |
| TATATTGTGT | TAACATTCCT | TTATTTGAGC | TTTGTGGCAA | TGGTATGCAC | 1750 |
| AGCGTTATGG | GCTTATGGAA | TTTGCGACGA | CGCGGTTCAA | CAGTTACAAT | 1800 |
| TGGAGAAACA | GCGACTCTAT | TCCCATGTAA | ACGAGTGACT | ATCTCTTGTG | 1850 |
| GAACTGGCTG | GGCTTGCACA | GATACTTTGA | TCGTCTTAGT | CAAGGAACCA | 1900 |
| TCCGGAAATA | TGGCCTGCAC | ATGAGGAACA | ACTGAAGAGA | GTATTACACC | 1950 |
| ACCTTCTGGA | CCAACACAGT | GCACTTCTTG | CCGCACACGA | GTAACGACCG | 2000 |
| CGAAATACAT | TGGGAAATCA | TTGGTCAGGA | TACGCGTAAT | CCGTGATGTA | 2050 |
| TGCAAATCAT | CAAGTTGCGA | CAACTCTTCT | GCATCAAACG | ATTCATTGAG | 2100 |
| CACCTCTTGT | ACAGCATCTT | CTGTTGCTTC | AAGCTGATGC | TCTTTCCAAT | 2150 |
| GCTGCCCATC | ATCAGAACGC | AAAATGACAA | TCTCTCTCTC | TCGTCCACGA | 2200 |
| AGTGATGCAA | AATGTGGTAC | TTCCAATATA | ACAGGGCCTA | AGAATTTTGC | 2250 |
| TCCATGTGGT | GCCATTTCAA | GTATACGTGA | NGCGAGCGCT | TCACCTTCAC | 2300 |
| TTAATGGTGG | TGGATGCGCT | AACTTGTCCT | TTCCAAGGTA | TCTGCATGTG | 2350 |
| ACCCGTGTAG | GTTGCGGCGC | TTTCCTCGGT | GGTATAATGA | TTCTGACACC | 2400 |
| GGAATGCCTA | CAACCACGCA | TTGCTCCTCC | ACGTGCATCC | ACCATAAACG | 2450 |
| AAATTAAAAA | ACTAGGTTGC | ATGGTAGTTC | TCATTATCGT | AACATTGTCA | 2500 |
| GGAAGCGATG | CATCTAAGGA | AGGATCGGCC | ATCGCTGTAG | TAATTGGTTC | 2550 |
| ATGTTGTGCT | TTACGAATTA | AGGCATCCAA | ATCGCCATCC | GTACCTTCCA | 2600 |
| CTTCCGGACT | TCGTGACAAT | GTCGGTTCTG | TGGCATGAAT | CAAATGTACA | 2650 |
| CCAGTTGAAT | CGTGCAAACC | TTTTGTGAGG | CTTTCTGAGA | AATCATGAGC | 2700 |
| ATGAGCATTG | GCTGTGATCT | GATTATCTTC | ACCTTCATCT | TCGGAATCGG | 2750 |
| AAAACATGGT | TTCATTCATT | GCTTCGGGAT | TCTGAGGTTT | ATATCTTTCT | 2800 |
| TCAGTAACGG | TTGTGGTCTC | CGTTATCACA | GTAGTCTCGG | TAATTGTTTT | 2850 |
| AAGCGCTTCA | ACCACGGATA | CATACCCTAG | ACGTTCAGCA | ATCGATAATG | 2900 |
| GAGTTTGTCC | TGTCGATGTA | TGAACATTTG | GACTTGCACC | ATGTTCCAAC | 2950 |
| AAGTAACGTA | CAACACTGTT | ATGCCCTTGC | TGAGCAGCTT | GATGCAGAGG | 3000 |
| AGTATAGGAA | GCACGAGTAA | TAACTGAAAC | TCGTGCGCCA | TGCTCAATCA | 3050 |
| AGAAACGGAC | CATGTTTATT | TGTCCAAAAT | GGCAAGCAAC | ATGTAACGGC | 3100 |
| GTATATCCTG | CTTTCGTTTT | GGGATCAATG | GCTGCGTTTT | CTTTCACTAG | 3150 |
| TTCTTCTGCT | ACGCTCACAC | GATCCTCCTG | TGCACATAAA | TGCATTGGTG | 3200 |
| TCAAGCCATT | CCTTGCCTGA | GCTCCAACTT | TTGCTCCATT | TTCAATTAAT | 3250 |
| AACGCAGCCA | TTTCGCGATG | GCCCTCCTGG | GCGGCAAGAT | GAAGTGGTGT | 3300 |
| AAAGCCAGCT | TTGCTTTCAG | CATTCGCATT | TGCCTTATAA | TGAAGGAGAG | 3350 |
| TGCTAGCAAT | ATCCATCTGA | TTCTTCTTCG | CGGCAATATG | TAAAGGAGTG | 3400 |

| | | | | |
|---|---|---|---|---|
| TACCCATTCT | TGGCAGCGGC | ATGTGCAGAA | GCACCATTTT | CTAGAAGTAA | 3450 |
| CAATGCTACC | TTGTCGTTAT | TGTAATGTGC | CGCTACATGC | AGAGGTGTTA | 3500 |
| CCTGATTCTT | GCCTTCAATG | TCAACCGGTG | TTCCTCGTTC | TAGCAATGAT | 3550 |
| TTCGCGACCG | GCAAATTGCC | ATACTTAGCA | GCTAAATGCA | ACGGCGTAAA | 3600 |
| ACCCTTTTTC | GTGAGCAGTG | TCTTGTCGGT | TCCATGATCC | ATCAATATTG | 3650 |
| CTGCCACTTC | CTCTTGCCCC | TCCTTGGCAG | CAATATGAAG | AGGAGTATAA | 3700 |
| AGATCTCTTG | TGGCAGCATT | TGGTGATGCA | TTAGCCTGCA | GCAACAAAAT | 3750 |
| GACGATGTCG | GTATTACCAA | GACGTGATGC | AATGTGCAGT | GGAGTTTGTA | 3800 |
| GTTCACGAGC | AGCAGCATCC | ACCTGTGCTC | CATTACGCAC | CAAAACACGA | 3850 |
| ACAATGTCCG | TTTGGTTTGC | TCGTGCAGCT | AAATGAAGAG | GCGTTTCACC | 3900 |
| GCGTACTGTA | GCCACATCTG | CATTAGCACC | TTGTTGTAGT | AAATAGATGA | 3950 |
| CAATGTTTAT | AGCACCCATA | AAAGCAGCGA | CATGCAGCGG | TGAGAGACCG | 4000 |
| GATTCAGTAG | TTGCTTCGAT | TGCAGCGTGG | TATTTCAGTA | GCAGTTCGAC | 4050 |
| AATTTTAATG | CGATTTTTTT | TGCAAGCGAT | ATGCAGCGGT | GTGAAGCCAT | 4100 |
| TGAGAGCTCG | AGCATTCGGG | TCAGCATTAC | GATCCAGCAA | AAGTTTAGCG | 4150 |
| ACACGGACAT | GTCCGCAATG | AGCAGCCACA | TGAAGAGGAG | TGAGATAGTC | 4200 |
| AACAGTAACA | TCATCCACCT | GTGCTGCCAT | ATGTAAGGGA | GCCAAACCAT | 4250 |
| TTTTTGTCTT | AGCACTGATT | GGAGCTCCTT | TTTCAAGCAA | CAAATCAACA | 4300 |
| ACTTGATCAT | GACCTGAACG | AGAAGCACAG | TGTAATGGTG | TTAGTAAATC | 4350 |
| ACGTGTGCGA | CAGTCAATTA | CGGCCCCATG | AGCCAACAAT | AACGAAACCA | 4400 |
| TGTTTGTACG | ACCCCATTTT | GTTGCAACGT | GTAACGGACT | TATGTTATGT | 4450 |
| CTCGCTTGGT | AATTCACATT | GGCTCCCTTT | TCGAGTAGCA | GTTGTGCTAC | 4500 |
| GTTCTCATTT | CCATAGTGAG | CGGCGATATG | AAGCGGAGTA | AAGCCGCTTT | 4550 |
| TCGAAGTCAC | ATCCGAGTTA | TGCTCATTTT | GAAGTAATAG | CGTAGCTGCT | 4600 |
| TTCGTATCAT | CTTTTTTAGC | AGCAATATGC | AGTGCTGGCA | AGCGCACTTT | 4650 |
| CCCGCGCGTG | TCATTTTCAA | GCAAACAGC | GACCACACGA | TCGTGACCTT | 4700 |
| GTTGCAAGGC | AACTGCCAGT | GGCGTAAAAC | CGTCTTCTGT | ACTTAAAGCT | 4750 |
| TGATTGGCAT | TGTGGGCAAG | AAGATAGCGT | ACAACAGATT | CGTGATTTTC | 4800 |
| TTGTGCAGCC | ATGTAAAGTG | GTGTAAAACC | GTTAGTGAT | TGTACGTTAA | 4850 |
| CATTAGCACC | ATTTTCAACA | AGTACTGTGA | CGATTAGTTC | TTGTCCTGCC | 4900 |
| AATGATGCTA | TATGTAACGC | TGTGTTACCC | TTTCTAGTGG | CAGCATCAAC | 4950 |
| ATCTGCTTTT | CTTTTCAGAA | GTTCGCGGAC | CACTTCATGA | TGACCTTCTT | 5000 |
| TGGAGGCCAG | ATGCAATGCA | TTAAGGCCAT | TCGCATTGCA | TGTGTTGATA | 5050 |
| TCGGTGCCCG | AACGAAGTAG | TTCAAGTACA | CGATCCAAAT | TTCCAGCTCT | 5100 |
| TGCTGCTCGT | AAAAAACTTG | CACTGCTCTC | ACCTTTGTTG | GAATGTTGAC | 5150 |
| TGTTATCATC | AGGAATTTGT | TGTTGATGTT | GTGAATCTTT | TGGTTCTGCG | 5200 |
| GGCCAGCCAC | TTCCCTCGAC | TATAGGATTA | CTCAT | | 5235 |

( 2 ) INFORMATION FOR SEQ ID NO:37:

( i ) SEQUENCE CHARACTERISTICS:
        ( A ) LENGTH: 908 nucleotides
        ( B ) TYPE: nucleic acid ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..906

( x i ) SEQUENCE DESCRIPTION: SEQ ID NO:37:

```
GAT  AAT  GTT  ACT  GTT  GAC  TAT  CTC  ACT  CCT  CTT  CAT  GTG  GCC                  42
Asp  Asn  Val  Thr  Val  Asp  Tyr  Leu  Thr  Pro  Leu  His  Val  Ala
 1              5                             10

GCC  CAC  TGC  GGA  CAT  GTC  CGT  GTC  GCT  AAG  CTT  CTG  CTG  GAT                  84
Ala  His  Cys  Gly  His  Val  Arg  Val  Ala  Lys  Leu  Leu  Leu  Asp
 15                       20                       25

CGT  AAT  GCC  GAT  TCA  AAT  GCT  CGG  GCT  CTC  AAT  GGC  TTC  ACA                 126
Arg  Asn  Ala  Asp  Ser  Asn  Ala  Arg  Ala  Leu  Asn  Gly  Phe  Thr
         30                       35                       40

CCG  TTG  CAC  ATA  GCT  TGC  AAA  AAA  AAT  CGC  ATT  AAG  GTT  GTC                 168
Pro  Leu  His  Ile  Ala  Cys  Lys  Lys  Asn  Arg  Ile  Lys  Val  Val
              45                       50                       55

GAA  CTG  TTG  CTG  AAA  TAT  CAT  GCT  GCC  ATC  GAG  GCA  ACT  ACA                 210
Glu  Leu  Leu  Leu  Lys  Tyr  His  Ala  Ala  Ile  Glu  Ala  Thr  Thr
                   60                       65                       70

GAA  TCC  GGT  CTG  TCG  CCG  CTT  CAC  GTC  GCT  GCT  TTC  ATG  GGT                 252
Glu  Ser  Gly  Leu  Ser  Pro  Leu  His  Val  Ala  Ala  Phe  Met  Gly
                        75                       80

GCT  ATA  AAC  ATC  GTT  ATC  TAC  TTA  CTG  CAG  CAG  GGT  GCT  AAT                 294
Ala  Ile  Asn  Ile  Val  Ile  Tyr  Leu  Leu  Gln  Gln  Gly  Ala  Asn
 85                       90                       95

GCG  AAT  GTG  GCT  ACT  GTA  CGC  GGT  GAA  ACA  CCT  CTT  CAT  TTA                 336
Ala  Asn  Val  Ala  Thr  Val  Arg  Gly  Glu  Thr  Pro  Leu  His  Leu
         100                      105                      110

GCT  GCA  CGA  GCG  AAC  CAA  ACC  GAT  ATT  GTC  CGT  GTT  TTG  GTA                 378
Ala  Ala  Arg  Ala  Asn  Gln  Thr  Asp  Ile  Val  Arg  Val  Leu  Val
              115                      120                      125

CGT  AAT  GGA  GCC  CAG  GTG  GAT  GCC  GCG  GCA  CGT  GAG  CTA  CAA                 420
Arg  Asn  Gly  Ala  Gln  Val  Asp  Ala  Ala  Ala  Arg  Glu  Leu  Gln
                   130                      135                      140

ACA  CCA  TTA  CAT  ATT  GCA  TCA  CGT  CTT  GGC  AAT  ACT  GAT  ATC                 462
Thr  Pro  Leu  His  Ile  Ala  Ser  Arg  Leu  Gly  Asn  Thr  Asp  Ile
                        145                      150

GTT  ATC  TTG  TTG  CTG  CAG  GCA  GAC  GCA  TCA  CCA  AAT  GCT  GCT                 504
Val  Ile  Leu  Leu  Leu  Gln  Ala  Asp  Ala  Ser  Pro  Asn  Ala  Ala
 155                      160                      165

ACA  CGG  GAT  CTC  TAC  ACT  CTT  CTT  CAT  ATT  GCT  GCC  AAA  GAG                 546
Thr  Arg  Asp  Leu  Tyr  Thr  Leu  Leu  His  Ile  Ala  Ala  Lys  Glu
         170                      175                      180

GGA  CAA  GAG  GAG  GTG  GCA  GCA  ATA  TTG  ATA  GAT  CAT  GGT  TCC                 588
Gly  Gln  Glu  Glu  Val  Ala  Ala  Ile  Leu  Ile  Asp  His  Gly  Ser
              185                      190                      195

GAT  AAG  ACA  TTG  CTT  ACC  AAG  AAA  GGT  TTT  ACA  CCG  TTG  CAT                 630
Asp  Lys  Thr  Leu  Leu  Thr  Lys  Lys  Gly  Phe  Thr  Pro  Leu  His
                   200                      205                      210

TTA  GCT  GCT  AAA  TAC  GGC  AAT  TTA  CCG  GTA  GCG  AAA  TTA  TTG                 672
Leu  Ala  Ala  Lys  Tyr  Gly  Asn  Leu  Pro  Val  Ala  Lys  Leu  Leu
                        215                      220

CTG  GAA  CGA  GGA  ACT  TTG  GTT  GAC  ATT  GAA  GGC  AAG  AAC  CAG                 714
Leu  Glu  Arg  Gly  Thr  Leu  Val  Asp  Ile  Glu  Gly  Lys  Asn  Gln
 225                      230                      235

GTG  ACA  CCT  TTG  CAT  GTA  GCA  GCA  CAT  TAT  AAT  AAC  GAC  AAG                 756
```

|  |  |  |  |  |  |  |  |  |  |  |  |  |
|---|---|---|---|---|---|---|---|---|---|---|---|---|
| Val | Thr<br>240 | Pro | Leu | His | Val<br>245 | Ala | Ala | His | Tyr | Asn<br>250 | Asn | Asp | Lys |

```
GTA  GCG  CTG  CTG  CTT  CTA  GAA  AGT  GGT  GCT  TCC  GCA  CAT  GCC                798
Val  Ala  Leu  Leu  Leu  Leu  Glu  Ser  Gly  Ala  Ser  Ala  His  Ala
          255                      260                      265

GTT  GCC  AAG  AAT  GGA  TAT  ACT  CCT  TTG  CAT  ATT  GCT  GCA  AAG                840
Val  Ala  Lys  Asn  Gly  Tyr  Thr  Pro  Leu  His  Ile  Ala  Ala  Lys
               270                      275                      280

AAA  AAT  CAG  ATG  GAT  ATT  GCT  AGC  ACT  CTT  CTT  CAT  TAT  AGG                882
Lys  Asn  Gln  Met  Asp  Ile  Ala  Ser  Thr  Leu  Leu  His  Tyr  Arg
                    285                      290

GCA  AAT  GCG  AAT  GCT  GAA  AGC  AAA  GC                                          908
Ala  Asn  Ala  Asn  Ala  Glu  Ser  Lys
295                      300
```

( 2 ) INFORMATION FOR SEQ ID NO:38:

( i ) SEQUENCE CHARACTERISTICS:
        ( A ) LENGTH: 302 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

```
Asp  Asn  Val  Thr  Val  Asp  Tyr  Leu  Thr  Pro  Leu  His  Val  Ala
 1              5                      10

Ala  His  Cys  Gly  His  Val  Arg  Val  Ala  Lys  Leu  Leu  Leu  Asp
15                       20                      25

Arg  Asn  Ala  Asp  Ser  Asn  Ala  Arg  Ala  Leu  Asn  Gly  Phe  Thr
          30                      35                      40

Pro  Leu  His  Ile  Ala  Cys  Lys  Lys  Asn  Arg  Ile  Lys  Val  Val
               45                      50                      55

Glu  Leu  Leu  Leu  Lys  Tyr  His  Ala  Ala  Ile  Glu  Ala  Thr  Thr
                    60                      65                      70

Glu  Ser  Gly  Leu  Ser  Pro  Leu  His  Val  Ala  Ala  Phe  Met  Gly
                         75                      80

Ala  Ile  Asn  Ile  Val  Ile  Tyr  Leu  Leu  Gln  Gln  Gly  Ala  Asn
85                            90                      95

Ala  Asn  Val  Ala  Thr  Val  Arg  Gly  Glu  Thr  Pro  Leu  His  Leu
     100                      105                     110

Ala  Ala  Arg  Ala  Asn  Gln  Thr  Asp  Ile  Val  Arg  Val  Leu  Val
               115                     120                     125

Arg  Asn  Gly  Ala  Gln  Val  Asp  Ala  Ala  Ala  Arg  Glu  Leu  Gln
                    130                     135                     140

Thr  Pro  Leu  His  Ile  Ala  Ser  Arg  Leu  Gly  Asn  Thr  Asp  Ile
                         145                     150

Val  Ile  Leu  Leu  Leu  Gln  Ala  Asp  Ala  Ser  Pro  Asn  Ala  Ala
155                           160                     165

Thr  Arg  Asp  Leu  Tyr  Thr  Leu  Leu  His  Ile  Ala  Ala  Lys  Glu
     170                      175                     180

Gly  Gln  Glu  Glu  Val  Ala  Ala  Ile  Leu  Ile  Asp  His  Gly  Ser
               185                     190                     195

Asp  Lys  Thr  Leu  Leu  Thr  Lys  Lys  Gly  Phe  Thr  Pro  Leu  His
                    200                     205                     210

Leu  Ala  Ala  Lys  Tyr  Gly  Asn  Leu  Pro  Val  Ala  Lys  Leu  Leu
                         215                     220

Leu  Glu  Arg  Gly  Thr  Leu  Val  Asp  Ile  Glu  Gly  Lys  Asn  Gln
225                           230                     235
```

| Val | Thr | Pro | Leu | His | Val | Ala | Ala | His | Tyr | Asn | Asn | Asp | Lys |
|-----|-----|-----|-----|-----|-----|-----|-----|-----|-----|-----|-----|-----|-----|
| 240 |     |     |     |     |     | 245 |     |     |     |     | 250 |     |     |

| Val | Ala | Leu | Leu | Leu | Leu | Glu | Ser | Gly | Ala | Ser | Ala | His | Ala |
|-----|-----|-----|-----|-----|-----|-----|-----|-----|-----|-----|-----|-----|-----|
|     |     | 255 |     |     |     |     | 260 |     |     |     |     | 265 |     |

| Val | Ala | Lys | Asn | Gly | Tyr | Thr | Pro | Leu | His | Ile | Ala | Ala | Lys |
|-----|-----|-----|-----|-----|-----|-----|-----|-----|-----|-----|-----|-----|-----|
|     |     |     | 270 |     |     |     |     | 275 |     |     |     |     | 280 |

| Lys | Asn | Gln | Met | Asp | Ile | Ala | Ser | Thr | Leu | Leu | His | Tyr | Arg |
|-----|-----|-----|-----|-----|-----|-----|-----|-----|-----|-----|-----|-----|-----|
|     |     |     |     | 285 |     |     |     |     | 290 |     |     |     |     |

| Ala | Asn | Ala | Asn | Ala | Glu | Ser | Lys |
|-----|-----|-----|-----|-----|-----|-----|-----|
| 295 |     |     |     |     | 300 |     |     |

( 2 ) INFORMATION FOR SEQ ID NO:39:

( i ) SEQUENCE CHARACTERISTICS:
        ( A ) LENGTH: 908 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

| | | | | | |
|---|---|---|---|---|---|
| GCTTTGCTTT | CAGCATTCGC | ATTTGCCCTA | TAATGAAGAA | GAGTGCTAGC | 50 |
| AATATCCATC | TGATTTTTCT | TTGCAGCAAT | ATGCAAAGGA | GTATATCCAT | 100 |
| TCTTGGCAAC | GGCATGTGCG | GAAGCACCAC | TTTCTAGAAG | CAGCAGCGCT | 150 |
| ACCTTGTCGT | TATTATAATG | TGCTGCTACA | TGCAAAGGTG | TCACCTGGTT | 200 |
| CTTGCCTTCA | ATGTCAACCA | AAGTTCCTCG | TTCCAGCAAT | AATTTCGCTA | 250 |
| CCGGTAAATT | GCCGTATTTA | GCAGCTAAAT | GCAACGGTGT | AAAACCTTTC | 300 |
| TTGGTAAGCA | ATGTCTTATC | GGAACCATGA | TCTATCAATA | TTGCTGCCAC | 350 |
| CTCCTCTTGT | CCCTCTTTGG | CAGCAATATG | AAGAAGAGTG | TAGAGATCCC | 400 |
| GTGTAGCAGC | ATTTGGTGAT | GCGTCTGCCT | GCAGCAACAA | GATAACGATA | 450 |
| TCAGTATTGC | CAAGACGTGA | TGCAATATGT | AATGGTGTTT | GTAGCTCACG | 500 |
| TGCCGCGGCA | TCCACCTGGG | CTCCATTACG | TACCAAAACA | CGGACAATAT | 550 |
| CGGTTTGGTT | CGCTCGTGCA | GCTAAATGAA | GAGGTGTTTC | ACCGCGTACA | 600 |
| GTAGCCACAT | TCGCATTAGC | ACCCTGCTGC | AGTAAGTAGA | TAACGATGTT | 650 |
| TATAGCACCC | ATGAAAGCAG | CGACGTGAAG | CGGCGACAGA | CCGGATTCTG | 700 |
| TAGTTGCCTC | GATGGCAGCA | TGATATTTCA | GCAACAGTTC | GACAACCTTA | 750 |
| ATGCGATTTT | TTTTGCAAGC | TATGTGCAAC | GGTGTGAAGC | CATTGAGAGC | 800 |
| CCGAGCATTT | GAATCGGCAT | TACGATCCAG | CAGAAGCTTA | GCGACACGGA | 850 |
| CATGTCCGCA | GTGGGCGGCC | ACATGAAGAG | GAGTGAGATA | GTCAACAGTA | 900 |
| ACATTATC | | | | | 908 |

( 2 ) INFORMATION FOR SEQ ID NO:40:

( i ) SEQUENCE CHARACTERISTICS:
        ( A ) LENGTH: 906 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

-continued

| | | | | | |
|---|---|---|---|---|---|
| GATAATGTTA | CTGTTGACTA | TCTCACTCCT | CTTCATGTGG | CCGCCCACTG | 50 |
| CGGACATGTC | CGTGTCGCTA | AGCTTCTGCT | GGATCGTAAT | GCCGATTCAA | 100 |
| ATGCTCGGGC | TCTCAATGGC | TTCACACCGT | TGCACATAGC | TTGCAAAAAA | 150 |
| AATCGCATTA | AGGTTGTCGA | ACTGTTGCTG | AAATATCATG | CTGCCATCGA | 200 |
| GGCAACTACA | GAATCCGGTC | TGTCGCCGCT | TCACGTCGCT | GCTTTCATGG | 250 |
| GTGCTATAAA | CATCGTTATC | TACTTACTGC | AGCAGGGTGC | TAATGCGAAT | 300 |
| GTGGCTACTG | TACGCGGTGA | AACACCTCTT | CATTTAGCTG | CACGAGCGAA | 350 |
| CCAAACCGAT | ATTGTCCGTG | TTTTGGTACG | TAATGGAGCC | CAGGTGGATG | 400 |
| CCGCGGCACG | TGAGCTACAA | ACACCATTAC | ATATTGCATC | ACGTCTTGGC | 450 |
| AATACTGATA | TCGTTATCTT | GTTGCTGCAG | GCAGACGCAT | CACCAAATGC | 500 |
| TGCTACACGG | GATCTCTACA | CTCTTCTTCA | TATTGCTGCC | AAAGAGGGAC | 550 |
| AAGAGGAGGT | GGCAGCAATA | TTGATAGATC | ATGGTTCCGA | TAAGACATTG | 600 |
| CTTACCAAGA | AAGGTTTTAC | ACCGTTGCAT | TTAGCTGCTA | AATACGGCAA | 650 |
| TTTACCGGTA | GCGAAATTAT | TGCTGGAACG | AGGAACTTTG | GTTGACATTG | 700 |
| AAGGCAAGAA | CCAGGTGACA | CCTTTGCATG | TAGCAGCACA | TTATAATAAC | 750 |
| GACAAGGTAG | CGCTGCTGCT | TCTAGAAAGT | GGTGCTTCCG | CACATGCCGT | 800 |
| TGCCAAGAAT | GGATATACTC | CTTTGCATAT | TGCTGCAAAG | AAAAATCAGA | 850 |
| TGGATATTGC | TAGCACTCTT | CTTCATTATA | GGGCAAATGC | GAATGCTGAA | 900 |
| AGCAAA | | | | | 906 |

( 2 ) INFORMATION FOR SEQ ID NO:41:

( i ) SEQUENCE CHARACTERISTICS:
        ( A ) LENGTH: 906 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:41:

| | | | | | |
|---|---|---|---|---|---|
| TTTGCTTTCA | GCATTCGCAT | TTGCCCTATA | ATGAAGAAGA | GTGCTAGCAA | 50 |
| TATCCATCTG | ATTTTTCTTT | GCAGCAATAT | GCAAGGAGT | ATATCCATTC | 100 |
| TTGGCAACGG | CATGTGCGGA | AGCACCACTT | TCTAGAAGCA | GCAGCGCTAC | 150 |
| CTTGTCGTTA | TTATAATGTG | CTGCTACATG | CAAAGGTGTC | ACCTGGTTCT | 200 |
| TGCCTTCAAT | GTCAACCAAA | GTTCCTCGTT | CCAGCAATAA | TTTCGCTACC | 250 |
| GGTAAATTGC | CGTATTTAGC | AGCTAAATGC | AACGGTGTAA | AACCTTTCTT | 300 |
| GGTAAGCAAT | GTCTTATCGG | AACCATGATC | TATCAATATT | GCTGCCACCT | 350 |
| CCTCTTGTCC | CTCTTTGGCA | GCAATATGAA | GAAGAGTGTA | GAGATCCCGT | 400 |
| GTAGCAGCAT | TTGGTGATGC | GTCTGCCTGC | AGCAACAAGA | TAACGATATC | 450 |
| AGTATTGCCA | AGACGTGATG | CAATATGTAA | TGGTGTTTGT | AGCTCACGTG | 500 |
| CCGCGGCATC | CACCTGGGCT | CCATTACGTA | CCAAACACG | GACAATATCG | 550 |
| GTTTGGTTCG | CTCGTGCAGC | TAAATGAAGA | GGTGTTTCAC | CGCGTACAGT | 600 |
| AGCCACATTC | GCATTAGCAC | CCTGCTGCAG | TAAGTAGATA | ACGATGTTTA | 650 |
| TAGCACCCAT | GAAAGCAGCG | ACGTGAAGCG | GCGACAGACC | GGATTCTGTA | 700 |
| GTTGCCTCGA | TGGCAGCATG | ATATTTCAGC | AACAGTTCGA | CAACCTTAAT | 750 |

```
GCGATTTTTT TTGCAAGCTA TGTGCAACGG TGTGAAGCCA TTGAGAGCCC         800

GAGCATTTGA ATCGGCATTA CGATCCAGCA GAAGCTTAGC GACACGGACA         850

TGTCCGCAGT GGGCGGCCAC ATGAAGAGGA GTGAGATAGT CAACAGTAAC         900

ATTATC                                                        906
```

( 2 ) INFORMATION FOR SEQ ID NO:42:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:42:

```
CATCAATTTT TGGAATTTTC TGG                                      23
```

( 2 ) INFORMATION FOR SEQ ID NO:43:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:43:

```
CGTTTACAGC AACATCATCC TC                                       22
```

( 2 ) INFORMATION FOR SEQ ID NO:44:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:44:

```
GCACAACCAG TTCCGCAAGA AA                                       22
```

( 2 ) INFORMATION FOR SEQ ID NO:45:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:45:

```
GGTTATTGGA AGAAGATTTC C                                        21
```

( 2 ) INFORMATION FOR SEQ ID NO:46:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: primer (ix) FEATURE:
            (A) NAME/KEY: N = any nucleotide
            (B) LOCATION: 9, 13

(xi) SEQUENCE DESCRIPTION: SEQ ID NO:46:

CAYCARGCNG CNCARCARGG NCA                    23

(2) INFORMATION FOR SEQ ID NO:47:

(i) SEQUENCE CHARACTERISTICS:
            (A) LENGTH: 23 nucleotides
            (B) TYPE: nucleic acid
            (C) STRANDEDNESS: single
            (D) TOPOLOGY: linear (ii) MOLECULE TYPE: primer (ix) FEATURE:
            (A) NAME/KEY: N = any nucleotide
            (B) LOCATION: 3, 13, 16, 19

(xi) SEQUENCE DESCRIPTION: SEQ ID NO:47:

GTNGAYGAYG TNACNGTNGA YTA                    23

(2) INFORMATION FOR SEQ ID NO:48:

(i) SEQUENCE CHARACTERISTICS:
            (A) LENGTH: 22 nucleotides
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:48:

GGAATTTGCG ACGACGCGGT TC                     22

(2) INFORMATION FOR SEQ ID NO:49:

(i) SEQUENCE CHARACTERISTICS:
            (A) LENGTH: 17 nucleotides
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:49:

CAGGAAACAG CTATGAC                           17

(2) INFORMATION FOR SEQ ID NO:50:

(i) SEQUENCE CHARACTERISTICS:
            (A) LENGTH: 24 nucleotides
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:50:

TGGAGTTTGT CCTGTCGATG TATG                   24

(2) INFORMATION FOR SEQ ID NO:51:

(i) SEQUENCE CHARACTERISTICS:
            (A) LENGTH: 27 nucleotides
            (B) TYPE: nucleic acid
            (C) STRANDEDNESS: single
            (D) TOPOLOGY: linear ( i i ) MOLECULE TYPE: primer ( x i ) SEQUENCE DESCRIPTION: SEQ ID NO:51:

GCTTTGCTTT CAGCATTCGC ATTTGCC                27

( 2 ) INFORMATION FOR SEQ ID NO:52:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:52:

GGTTTAATTA CCCAAGTTTG AG                22

( 2 ) INFORMATION FOR SEQ ID NO:53:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:53:

GTGAGATAGT CAACAGTAAC ATCATCC                27

( 2 ) INFORMATION FOR SEQ ID NO:54:

( i ) SEQUENCE CHARACTERISTICS:
        ( A ) LENGTH: 31 nucleotides
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:54:

CGCGGATCCG GCACAACCAG TTCCGCAAGA A                31

( 2 ) INFORMATION FOR SEQ ID NO:55:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:55:

CCGGAATTCT TATTCATGAA CGCTTTGCCC                30

( 2 ) INFORMATION FOR SEQ ID NO:56:

( i ) SEQUENCE CHARACTERISTICS:
        ( A ) LENGTH: 33 nucleotides
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:56:

CGCGGATCCG ATGAGTAATC CTATAGTCGA GGG                    33

( 2 ) INFORMATION FOR SEQ ID NO:57:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:57:

CCGGAATTCC GGTTACCCTA GACGTTCAGC AATCG                  35

( 2 ) INFORMATION FOR SEQ ID NO:58:

( i ) SEQUENCE CHARACTERISTICS:
        ( A ) LENGTH: 34 nucleotides
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:58:

CGCGGATCCG CGCGCACGTG GAGGAGCAAT GCGT                   34

( 2 ) INFORMATION FOR SEQ ID NO:59:

( i ) SEQUENCE CHARACTERISTICS:
        ( A ) LENGTH: 36 nucleotides
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:59:

CCGGAATTCC GGTTATTCGT TGTCCGTGTG AGTGCG                 36

( 2 ) INFORMATION FOR SEQ ID NO:60:

( i ) SEQUENCE CHARACTERISTICS:
        ( A ) LENGTH: 37 nucleotides
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:60:

CGCGGATCCG CGCCAACTAG TTGGTCTTGA AGCAGTC                37

( 2 ) INFORMATION FOR SEQ ID NO:61:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:61:

Glu Ser Ser Ala Ser Phe Leu Arg Ala Ala Arg Ala Gly Asn
1               5                   10

Leu Asp Arg Val Leu Glu Leu Leu Arg Ser Gly Thr Asp Ile
15                  20                  25

-continued

Asn Thr Cys Asn Ala
          30

( 2 ) INFORMATION FOR SEQ ID NO:62:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:62:

Asn Gly Leu Asn Ala Leu His Leu Ala Ser Lys Glu Gly His
 1               5                  10
His Glu Val Val Arg Glu Leu Leu Lys Arg Lys Ala Asp Val
15                  20                  25
Asp Ala Ala Thr Arg
          30

( 2 ) INFORMATION FOR SEQ ID NO:63:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:63:

Lys Gly Asn Thr Ala Leu His Ile Ala Ser Leu Ala Gly Gln
 1               5                  10
Glu Leu Ile Val Thr Val Leu Val Glu Asn Gly Ala Asn Val
15                  20                  25
Asn Val Gln Ser Leu
          30

( 2 ) INFORMATION FOR SEQ ID NO:64:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:64:

Asn Gly Phe Thr Pro Leu Tyr Met Ala Ala Gln Glu Asn His
 1               5                  10
Glu Ser Val Val Arg Tyr Leu Leu Ala His Asn Ala Asn Gln
15                  20                  25
Ala Leu Ser Thr Glu
          30

( 2 ) INFORMATION FOR SEQ ID NO:65:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: protein ( x i ) SEQUENCE DESCRIPTION: SEQ ID NO:65:

Asp Gly Phe Thr Pro Leu Ala Val Ala Leu Gln Gln Gly His
 1               5                          20

Asp Arg Val Val Ala Val Leu Leu Glu Asn Asp Thr Arg Gly
15                  20                  25

Lys ( 2 ) INFORMATION FOR SEQ ID NO:66:

( i ) SEQUENCE CHARACTERISTICS:
                ( A ) LENGTH: 33 amino acids
                ( B ) TYPE: amino acid
                ( D ) TOPOLOGY: linear ( i i ) MOLECULE TYPE: protein ( x i ) SEQUENCE DESCRIPTION: SEQ ID NO:66:

Val Arg Leu Pro Ala Leu His Ile Ala Ala Lys Lys Asp Asp
1                5                   10

Thr Lys Ala Ala Thr Leu Leu Leu Gln Asn Glu His Asn Ser
15                  20                  25

Asp Val Thr Ser Lys
        30

( 2 ) INFORMATION FOR SEQ ID NO:67:

( i ) SEQUENCE CHARACTERISTICS:
                ( A ) LENGTH: 33 amino acids
                ( B ) TYPE: amino acid
                ( D ) TOPOLOGY: linear ( i i ) MOLECULE TYPE: protein ( x i ) SEQUENCE DESCRIPTION: SEQ ID NO:67:

Ser Gly Phe Thr Pro Leu His Ile Ala Ala His Tyr Gly Asn
1                5                   10

Glu Asn Val Ala Gln Leu Leu Leu Glu Lys Gly Ala Asn Val
15                  20                  25

Asn Tyr Gln Ala Arg
        30

( 2 ) INFORMATION FOR SEQ ID NO:68:

( i ) SEQUENCE CHARACTERISTICS:
                ( A ) LENGTH: 33 amino acids
                ( B ) TYPE: amino acid
                ( D ) TOPOLOGY: linear ( i i ) MOLECULE TYPE: protein ( x i ) SEQUENCE DESCRIPTION: SEQ ID NO:68:

His Asn Ile Ser Pro Leu His Val Ala Thr Lys Trp Gly Arg
1                5                   10

Thr Asn Met Val Ser Leu Leu Leu Ala His Gly Ala Val Ile
15                  20                  25

Asp Cys Arg Thr Arg
        30

( 2 ) INFORMATION FOR SEQ ID NO:69:

( i ) SEQUENCE CHARACTERISTICS:
                ( A ) LENGTH: 33 amino acids
                ( B ) TYPE: amino acid
                ( D ) TOPOLOGY: linear ( i i ) MOLECULE TYPE: protein ( x i ) SEQUENCE DESCRIPTION: SEQ ID NO:69:

```
Asp  Leu  Leu  Thr  Pro  Leu  His  Cys  Ala  Ser  Arg  Ser  Gly  His
 1              5                        10
Asp  Gln  Val  Val  Asp  Leu  Leu  Glu  Lys  Gly  Ala  Pro  Ile
15                  20                       25
Ser  Ala  Lys  Thr  Lys
          30
```

(2) INFORMATION FOR SEQ ID NO:70:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:70:

```
Asn  Gly  Leu  Ala  Pro  Leu  His  Met  Ala  Ala  Gln  Val  Asp  Asp
 1              5                        10
Val  Thr  Val
15
```

(2) INFORMATION FOR SEQ ID NO:71:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:71:

```
Asp  Tyr  Leu  Thr  Pro  Leu  His  Val  Ala  Ala  His  Cys  Gly  His
 1              5                        10
Val  Arg  Val  Ala  Lys  Leu  Leu  Leu  Asp  Arg  Asn  Ala  Asp  Pro
15                  20                       25
Asn  Ala  Arg  Ala  Leu
          30
```

(2) INFORMATION FOR SEQ ID NO:72:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:72:

```
Asn  Gly  Phe  Thr  Pro  Leu  His  Ile  Ala  Cys  Lys  Lys  Asn  Arg
 1              5                        10
Ile  Lys  Ile  Val  Glu  Leu  Leu  Leu  Lys  Tyr  His  Ala  Ala  Ile
15                  20                       25
Glu  Ala  Thr  Thr  Glu
          30
```

(2) INFORMATION FOR SEQ ID NO:73:

(i) SEQUENCE CHARACTERISTICS:
        (A) LENGTH: 33 amino acids
        (B) TYPE: amino acid
        (D) TOPOLOGY: linear (ii) MOLECULE TYPE: protein ( x i ) SEQUENCE DESCRIPTION: SEQ ID NO:73:

Ser Gly Leu Ser Pro Leu His Val Ala Ala Phe Met Gly Ala
 1               5                      10
Ile Asn Ile Val Ile Tyr Leu Leu Gln Gln Gly Ala Asn Ala
15                   20                  25
Asp Val Ala Thr Val
         30

( 2 ) INFORMATION FOR SEQ ID NO:74:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:74:

Arg Gly Glu Thr Pro Leu His Leu Ala Ala Arg Ala Asn Gln
 1               5                      10
Thr Asp Ile Val Arg Val Leu Val Arg Asn Gly Ala Gln Val
15                   20                  25
Asp Ala Ala Ala Arg
         30

( 2 ) INFORMATION FOR SEQ ID NO:75:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:75:

Glu Leu Gln Thr Pro Leu His Ile Ala Ser Arg Leu Gly Asn
 1               5                      10
Thr Asp Ile Val Ile Leu Leu Leu Gln Ala Asn Ala Ser Pro
15                   20                  25
Asn Ala Ala Thr Arg
         30

( 2 ) INFORMATION FOR SEQ ID NO:76:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:76:

Asp Leu Tyr Thr Pro Leu His Ile Ala Ala Lys Glu Gly Gln
 1               5                      10
Glu Glu Val Ala Ala Ile Leu Met Asp His Gly Thr Asp Lys
15                   20                  25
Thr Leu Leu Thr Lys
         30

( 2 ) INFORMATION FOR SEQ ID NO:77:

( i ) SEQUENCE CHARACTERISTICS:
        ( A ) LENGTH: 33 amino acids
        ( B ) TYPE: amino acid (D) TOPOLOGY: linear (ii) MOLECULE TYPE: protein (xi) SEQUENCE DESCRIPTION: SEQ ID NO:77:

```
Lys Gly Phe Thr Pro Leu His Leu Ala Ala Lys Tyr Gly Asn
1               5                   10
Leu Pro Val Ala Lys Ser Leu Leu Glu Arg Gly Thr Pro Val
15                  20                  25
Asp Ile Glu Gly Lys
        30
```

(2) INFORMATION FOR SEQ ID NO:78:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:78:

```
Asn Gln Val Thr Pro Leu His Val Ala Ala His Tyr Asn Asn
1               5                   10
Asp Lys Val Ala Leu Leu Leu Leu Glu Asn Gly Ala Ser Ala
15                  20                  25
His Ala Ala Ala Lys
        30
```

(2) INFORMATION FOR SEQ ID NO:79:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:79:

```
Asn Gly Tyr Thr Pro Leu His Ile Ala Ala Lys Lys Asn Gln
1               5                   10
Met Asp Ile Ala Ser Thr Leu Leu His Tyr Lys Ala Asn Ala
15                  20                  25
Asn Ala Glu Ser Lys
        30
```

(2) INFORMATION FOR SEQ ID NO:80:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:80:

```
Ala Gly Phe Thr Pro Leu His Leu Ala Ala Gln Glu Gly His
1               5                   10
Arg Glu Met Ala Ala Leu Leu Ile Glu Asn Gly Ala Lys Val
15                  20                  25
Gly Ala Gln Ala Arg
        30
```

(2) INFORMATION FOR SEQ ID NO:81:

( i ) SEQUENCE CHARACTERISTICS:
  ( A ) LENGTH: 33 amino acids
  ( B ) TYPE: amino acid
  ( D ) TOPOLOGY: linear ( i i ) MOLECULE TYPE: protein ( x i ) SEQUENCE DESCRIPTION: SEQ ID NO:81:

Asn Gly Leu Thr Pro Met His Leu Cys Ala Gln Glu Asp Arg
 1               5                  10
Val Ser Val Ala Glu Glu Leu Val Lys Glu Asn Ala Ala Ile
15                  20                  25
Asp Pro Lys Thr Lys
        30

( 2 ) INFORMATION FOR SEQ ID NO:82:

( i ) SEQUENCE CHARACTERISTICS:
    ( A ) LENGTH: 33 amino acids
    ( B ) TYPE: amino acid
    ( D ) TOPOLOGY: linear ( i i ) MOLECULE TYPE: protein ( x i ) SEQUENCE DESCRIPTION: SEQ ID NO:82:

Ala Gly Tyr Thr Pro Leu His Val Ala Cys His Phe Gly Gln
 1               5                  10
Ile Asn Met Val Arg Phe Leu Ile Glu His Gly Ala Arg Val
15                  20                  25
Ser Val Ile Thr Arg
        30

( 2 ) INFORMATION FOR SEQ ID NO:83:

( i ) SEQUENCE CHARACTERISTICS:
    ( A ) LENGTH: 33 amino acids
    ( B ) TYPE: amino acid
    ( D ) TOPOLOGY: linear ( i i ) MOLECULE TYPE: protein ( x i ) SEQUENCE DESCRIPTION: SEQ ID NO:83:

Ala Ser Tyr Thr Pro Leu His Gln Ala Ala Gln Gln Gly His
 1               5                  10
Asn Ser Val Val Arg Tyr Leu Leu Glu His Gly Ala Ser Pro
15                  20                  25
Asn Val His Thr Ser
        30

( 2 ) INFORMATION FOR SEQ ID NO:84:

( i ) SEQUENCE CHARACTERISTICS:
    ( A ) LENGTH: 33 amino acids
    ( B ) TYPE: amino acid
    ( D ) TOPOLOGY: linear ( i i ) MOLECULE TYPE: protein ( x i ) SEQUENCE DESCRIPTION: SEQ ID NO:84:

Thr Gly Gln Thr Pro Leu Ser Ile Ala Glu Arg Leu Gly Tyr
 1               5                  10
Val Ser Val Val Glu Ala Leu Lys Thr Ile Thr Glu Thr Thr
15                  20                  25
Val Ile Thr Glu Thr

-continued

30

(2) INFORMATION FOR SEQ ID NO:85:

(i) SEQUENCE CHARACTERISTICS:
        (A) LENGTH: 33 amino acids
        (B) TYPE: amino acid
        (D) TOPOLOGY: linear (ii) MOLECULE TYPE: protein (ix) FEATURE:
        (A) NAME/KEY: Xaa = any amino acid
        (B) LOCATION: 1, 3, 8, 11, 12, 15, 16,
            17, 19, 20, 23, 24, 27, 28,
            30, 31, 32, 33

(ix) FEATURE:
        (A) NAME/KEY: Xaa = Val or Ala
        (B) LOCATION: 18

(ix) FEATURE:
        (A) NAME/KEY: Xaa = Asn or Asp
        (B) LOCATION: 29

(xi) SEQUENCE DESCRIPTION: SEQ ID NO:85:

```
Xaa  Gly  Xaa  Thr  Pro  Leu  His  Xaa  Ala  Ala  Xaa  Xaa  Gly  His
 1                    5                         10

Xaa  Xaa  Xaa  Xaa  Xaa  Xaa  Leu  Leu  Xaa  Xaa  Gly  Ala  Xaa  Xaa
 15                  20                         25

Xaa  Xaa  Xaa  Xaa  Xaa
 30
```